US012630817B1

(12) United States Patent
Waldo et al.

(10) Patent No.: US 12,630,817 B1
(45) Date of Patent: May 19, 2026

(54) FLUORESCENT PROTEINS AND SPLIT FLUORESCENT PROTEINS FROM CORYNACTIS CALIFORNICA AND METHODS OF USE

(71) Applicant: Triad National Security, LLC, Los Alamos, NM (US)

(72) Inventors: Geoffrey S. Waldo, Santa Fe, NM (US); Hau Thi Bich Nguyen, Los Alamos, NM (US)

(73) Assignee: Triad National Security, LLC, Los Alamos, NM (US)

( * ) Notice: Subject to any disclaimer, the term of this patent is extended or adjusted under 35 U.S.C. 154(b) by 1057 days.

(21) Appl. No.: 17/731,676

(22) Filed: Apr. 28, 2022

Related U.S. Application Data

(60) Provisional application No. 63/181,449, filed on Apr. 29, 2021.

(51) Int. Cl.
*C12N 15/10* (2006.01)
*C12Q 1/6897* (2018.01)

(52) U.S. Cl.
CPC ..... *C12N 15/1058* (2013.01); *C12N 15/1065* (2013.01); *C12Q 1/6897* (2013.01)

(58) Field of Classification Search
CPC ............ C12N 15/1058; C12N 15/1065; C12Q 1/6897
See application file for complete search history.

(56) References Cited

U.S. PATENT DOCUMENTS

| | | | |
|---|---|---|---|
| 8,168,411 | B2 | 5/2012 | Bradbury et al. |
| 8,420,390 | B2 | 4/2013 | Waldo et al. |
| 8,685,667 | B2 | 4/2014 | Waldo et al. |
| 9,637,528 | B2 | 5/2017 | Bradbury et al. |
| 2012/0282643 | A1 | 11/2012 | Lockard et al. |
| 2015/0099271 | A1 | 4/2015 | Waldo et al. |

FOREIGN PATENT DOCUMENTS

WO    WO 2012/135535    10/2012

OTHER PUBLICATIONS

Nguyen et al., "Engineering an efficient and bright split *Corynactis californica* green fluorescent protein," *Scientific Reports*, vol. 11, No. 18440, 2021 (15 pages).

*Primary Examiner* — Paul J Holland
(74) *Attorney, Agent, or Firm* — Klarquist Sparkman, LLP

(57) ABSTRACT

Fluorescent proteins and split-fluorescent proteins (SFPs) including split-green fluorescent proteins from *Corynactis californica* are provided. Nucleic acid molecules encoding the fluorescent proteins and SFPs, vectors, and kits are also provided. Methods of using the fluorescent proteins and SFPs, such as detecting a protein of interest or protein-protein interactions are also provided.

13 Claims, 23 Drawing Sheets

Specification includes a Sequence Listing.

FIG. 19A
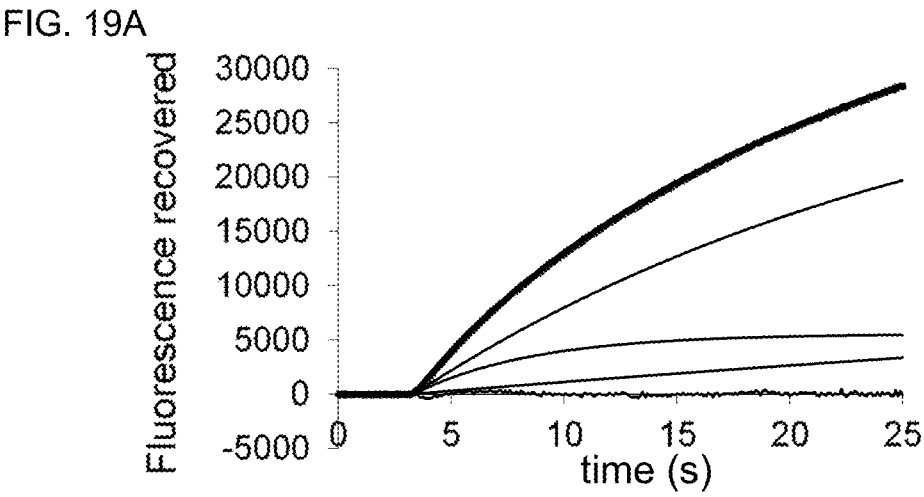
FIG. 19B
FIG. 19C
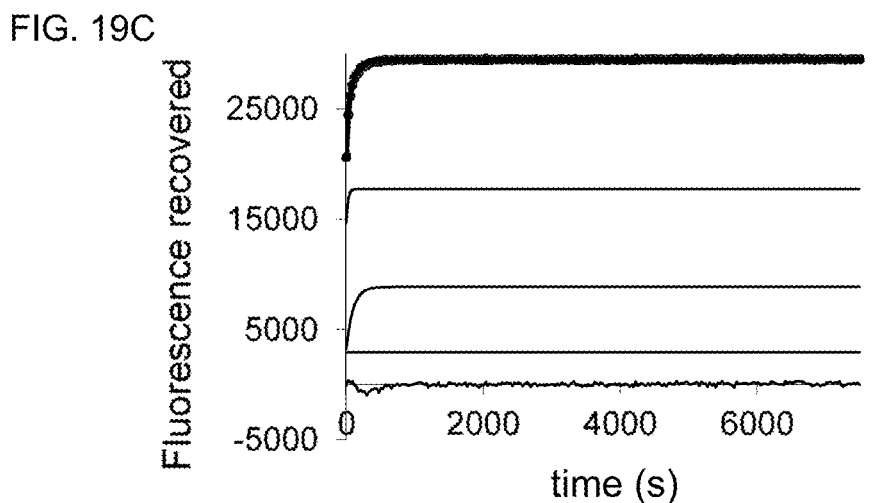

SEQUENCE LISTING

<160> NUMBER OF SEQ ID NOS: 18

<210> SEQ ID NO 1
<211> LENGTH: 202
<212> TYPE: PRT
<213> ORGANISM: Artificial Sequence
<220> FEATURE:
<223> OTHER INFORMATION: Split ccGFP 1-10 polypeptide version 1

<400> SEQUENCE: 1

Met Ser Met Ser Lys Gln Val Leu Lys Glu Asn Met Lys Thr Thr Tyr
1               5                   10                  15

His Met Asp Gly Ser Val Asn Gly His Tyr Phe Thr Ile Glu Gly Glu
            20                  25                  30

Gly Thr Gly Asn Pro Phe Lys Gly Gln Gln Ser Leu Lys Leu Arg Val
        35                  40                  45

Thr Lys Gly Gly Pro Leu Pro Phe Ala Phe Asp Ile Leu Ser Pro Thr
    50                  55                  60

Phe Thr Tyr Gly Asn Arg Val Phe Thr Asp Tyr Pro Glu Asp Met Pro
65                  70                  75                  80

-continued

Asp Tyr Phe Lys Gln Ser Leu Pro Glu Gly Tyr Ser Trp Glu Arg Thr
                85              90              95

Met Met Tyr Glu Asp Gly Ala Thr Ala Thr Ala Ser Ala Arg Ile Ser
            100             105             110

Leu Asp Lys Asn Gly Phe Val His Lys Ser Thr Phe His Gly Glu Asn
            115             120             125

Phe Pro Ala Asn Gly Pro Val Met Lys Lys Lys Gly Val Asn Trp Glu
        130             135             140

Pro Ser Ser Glu Thr Ile Thr Pro Ser Asp Gly Ile Leu Lys Gly Asp
145             150             155             160

Val Thr Met Phe Leu Val Leu Glu Gly Gly Gln Arg Leu Lys Ala Leu
            165             170             175

Phe Gln Thr Thr Tyr Lys Ala Asn Lys Val Val Lys Met Pro Pro Arg
            180             185             190

His Lys Ile Glu His Arg Leu Val Arg Ser
        195             200

<210> SEQ ID NO 2
<211> LENGTH: 202
<212> TYPE: PRT
<213> ORGANISM: Artificial Sequence
<220> FEATURE:
<223> OTHER INFORMATION: split ccGFP 1-10 polypeptide, version 2

<400> SEQUENCE: 2

Met Ser Met Ser Lys Gln Val Leu Lys Glu Asn Met Lys Thr Thr Tyr
1               5               10              15

His Met Asp Gly Ser Val Asn Gly His Tyr Phe Thr Ile Glu Gly Glu
            20              25              30

Gly Thr Gly Asn Pro Phe Lys Gly Gln Gln Ser Leu Lys Leu Arg Val
            35              40              45

Thr Lys Gly Gly Pro Leu Pro Phe Ala Phe Asp Ile Leu Ser Pro Thr
        50              55              60

Phe Thr Tyr Gly Asn Arg Val Phe Thr Asp Tyr Pro Glu Tyr Met Pro
65              70              75              80

Asp Tyr Phe Lys Arg Ser Leu Pro Glu Gly Tyr Ser Trp Glu Arg Thr
                85              90              95

Met Met Tyr Glu Asp Gly Ala Thr Ala Thr Ala Ser Val Arg Ile Ser
            100             105             110

Leu Asp Lys Asn Gly Phe Val His Lys Ser Thr Phe His Gly Glu Asn
            115             120             125

Phe Pro Ala Asn Gly Pro Val Met Lys Lys Lys Gly Val Asn Trp Glu
        130             135             140

Pro Ser Ser Glu Thr Ile Thr Pro Ser Asp Gly Ile Leu Lys Gly Asp
145             150             155             160

Val Thr Met Phe Leu Val Leu Glu Gly Gly Gln Arg Leu Lys Ala Leu
            165             170             175

Phe Gln Thr Thr Tyr Lys Ala Asn Lys Val Val Lys Met Pro Pro Arg
            180             185             190

His Lys Ile Glu His Arg Leu Val Arg Ser
        195             200

<210> SEQ ID NO 3
<211> LENGTH: 202
<212> TYPE: PRT
<213> ORGANISM: Artificial Sequence
<220> FEATURE:

-continued

<223> OTHER INFORMATION: split ccGFP 1-10 polypeptide, version 3

<400> SEQUENCE: 3

```
Met Ser Met Glu Lys Gln Val Leu Lys Glu Asn Met Lys Thr Thr Tyr
1               5                   10                  15

His Met Asp Gly Ser Val Asp Gly His Tyr Phe Glu Ile Glu Gly Glu
            20                  25                  30

Gly Thr Gly Asn Pro Phe Lys Gly Glu Gln Glu Leu Lys Leu Arg Val
        35                  40                  45

Thr Lys Gly Gly Pro Leu Pro Phe Ala Phe Asp Ile Leu Ser Pro Thr
    50                  55                  60

Phe Thr Tyr Gly Asn Arg Val Phe Thr Asp Tyr Pro Glu Asp Met Pro
65                  70                  75                  80

Asp Tyr Phe Lys Gln Ser Leu Pro Glu Gly Tyr Ser Trp Glu Arg Thr
                85                  90                  95

Met Met Tyr Glu Asp Gly Ala Thr Ala Thr Ala Ser Ala Arg Ile Ser
            100                 105                 110

Leu Asp Lys Asn Gly Phe Val His Lys Ser Thr Phe His Gly Glu Asn
        115                 120                 125

Phe Pro Ala Asn Gly Pro Val Met Lys Lys Lys Gly Val Asp Trp Glu
    130                 135                 140

Pro Ser Ser Glu Thr Ile Thr Pro Glu Asp Gly Ile Leu Lys Gly Asp
145                 150                 155                 160

Val Glu Met Phe Leu Val Leu Glu Gly Gly Gln Arg Leu Lys Ala Leu
                165                 170                 175

Phe Gln Thr Thr Tyr Lys Ala Asn Lys Val Val Lys Met Pro Pro Arg
            180                 185                 190

His Lys Ile Glu His Arg Leu Val Arg Ser
        195                 200
```

<210> SEQ ID NO 4
<211> LENGTH: 17
<212> TYPE: PRT
<213> ORGANISM: Artificial Sequence
<220> FEATURE:
<223> OTHER INFORMATION: split ccGFP S11 polypeptide

<400> SEQUENCE: 4

```
Gly Glu Thr Ile Gln Leu Gln Glu His Ala Val Ala Lys Tyr Phe Thr
1               5                   10                  15

Glu
```

<210> SEQ ID NO 5
<211> LENGTH: 221
<212> TYPE: PRT
<213> ORGANISM: Artificial Sequence
<220> FEATURE:
<223> OTHER INFORMATION: modified ccGFP E6 polypeptide

<400> SEQUENCE: 5

```
Met Ser Met Ser Lys Gln Val Leu Lys Glu Asp Met Lys Met Thr Tyr
1               5                   10                  15

His Met Asp Gly Ser Val Asn Gly His Tyr Phe Thr Ile Glu Gly Glu
            20                  25                  30

Gly Thr Gly Asn Pro Phe Lys Gly Gln Gln Thr Leu Lys Leu Arg Val
        35                  40                  45

Thr Lys Gly Gly Pro Leu Pro Phe Ala Phe Asp Ile Leu Ser Pro Thr
    50                  55                  60
```

```
Phe Thr Tyr Gly Asn Arg Val Phe Thr Asp Tyr Pro Glu Asp Met Pro
65                  70                  75                  80

Asp Tyr Phe Lys Gln Ser Leu Pro Glu Gly Tyr Ser Trp Glu Arg Thr
                85                  90                  95

Met Met Tyr Asp Asp Gly Ala Ser Ala Thr Ala Ser Ala Arg Ile Ser
                100                 105                 110

Leu Asp Lys Asn Gly Phe Val His Lys Ser Thr Phe His Gly Glu Asn
                115                 120                 125

Phe Pro Ala Asn Gly Pro Val Met Lys Lys Lys Gly Val Asn Trp Glu
        130                 135                 140

Pro Ser Ser Glu Thr Ile Thr Ala Ser Asp Gly Ile Leu Lys Gly Asp
145                 150                 155                 160

Val Thr Met Phe Leu Val Leu Glu Gly Gly Gln Arg Leu Lys Ala Leu
                165                 170                 175

Phe Gln Thr Thr Tyr Lys Ala Asn Lys Val Val Lys Met Pro Pro Arg
                180                 185                 190

His Lys Ile Glu His Arg Leu Val Arg Ser Glu Asp Gly Asp Thr Val
                195                 200                 205

Gln Leu Gln Glu His Ala Val Ala Lys Tyr Phe Thr Val
        210                 215                 220
```

```
<210> SEQ ID NO 6
<211> LENGTH: 221
<212> TYPE: PRT
<213> ORGANISM: Artificial Sequence
<220> FEATURE:
<223> OTHER INFORMATION: modified ccGFP polypeptide

<400> SEQUENCE: 6
```

```
Met Ser Met Ser Lys Gln Val Leu Lys Glu Asn Met Lys Thr Thr Tyr
1               5                   10                  15

His Met Asp Gly Ser Val Asn Gly His Tyr Phe Thr Ile Glu Gly Glu
                20                  25                  30

Gly Thr Gly Asn Pro Phe Lys Gly Gln Gln Ser Leu Lys Leu Arg Val
            35                  40                  45

Thr Lys Gly Gly Pro Leu Pro Phe Ala Phe Asp Ile Leu Ser Pro Thr
        50                  55                  60

Phe Thr Tyr Gly Asn Arg Val Phe Thr Asp Tyr Pro Glu Asp Met Pro
65                  70                  75                  80

Asp Tyr Phe Lys Gln Ser Leu Pro Glu Gly Tyr Ser Trp Glu Arg Thr
                85                  90                  95

Met Met Tyr Glu Asp Gly Ala Thr Ala Thr Ala Ser Ala Arg Ile Ser
                100                 105                 110

Leu Asp Lys Asn Gly Phe Val His Lys Ser Thr Phe His Gly Glu Asn
                115                 120                 125

Phe Pro Ala Asn Gly Pro Val Met Lys Lys Lys Gly Val Asn Trp Glu
        130                 135                 140

Pro Ser Ser Glu Thr Ile Thr Pro Ser Asp Gly Ile Leu Lys Gly Asp
145                 150                 155                 160

Val Thr Met Phe Leu Val Leu Glu Gly Gly Gln Arg Leu Lys Ala Leu
                165                 170                 175

Phe Gln Thr Thr Tyr Lys Ala Asn Lys Val Val Lys Met Pro Pro Arg
                180                 185                 190

His Lys Ile Glu His Arg Leu Val Arg Ser Glu Asp Gly Glu Thr Ile
                195                 200                 205
```

-continued

```
Gln Leu Gln Glu His Ala Val Ala Lys Tyr Phe Thr Glu
    210                 215                 220

<210> SEQ ID NO 7
<211> LENGTH: 221
<212> TYPE: PRT
<213> ORGANISM: Artificial Sequence
<220> FEATURE:
<223> OTHER INFORMATION: modified ccGFP polypeptide #9

<400> SEQUENCE: 7

Met Ser Met Glu Lys Gln Val Leu Lys Glu Asn Met Lys Thr Thr Tyr
1               5                   10                  15

His Met Asp Gly Ser Val Asp Gly His Tyr Phe Glu Ile Glu Gly Glu
            20                  25                  30

Gly Thr Gly Asn Pro Phe Lys Gly Glu Gln Glu Leu Lys Leu Arg Val
            35                  40                  45

Thr Lys Gly Gly Pro Leu Pro Phe Ala Phe Asp Ile Leu Ser Pro Thr
    50                  55                  60

Phe Thr Tyr Gly Asn Arg Val Phe Thr Asp Tyr Pro Glu Asp Met Pro
65                  70                  75                  80

Asp Tyr Phe Lys Gln Ser Leu Pro Glu Gly Tyr Ser Trp Glu Arg Thr
                85                  90                  95

Met Met Tyr Glu Asp Gly Ala Thr Ala Thr Ala Ser Ala Arg Ile Ser
                100                 105                 110

Leu Asp Lys Asn Gly Phe Val His Lys Ser Thr Phe His Gly Glu Asn
        115                 120                 125

Phe Pro Ala Asn Gly Pro Val Met Lys Lys Lys Gly Val Asp Trp Glu
    130                 135                 140

Pro Ser Ser Glu Thr Ile Thr Pro Glu Asp Gly Ile Leu Lys Gly Asp
145                 150                 155                 160

Val Glu Met Phe Leu Val Leu Glu Gly Gly Gln Arg Leu Lys Ala Leu
                165                 170                 175

Phe Gln Thr Thr Tyr Lys Ala Asn Lys Val Val Lys Met Pro Pro Arg
                180                 185                 190

His Lys Ile Glu His Arg Leu Val Arg Ser Glu Asp Gly Glu Thr Ile
        195                 200                 205

Gln Leu Gln Glu His Ala Val Ala Lys Tyr Phe Thr Glu
    210                 215                 220

<210> SEQ ID NO 8
<211> LENGTH: 221
<212> TYPE: PRT
<213> ORGANISM: Artificial Sequence
<220> FEATURE:
<223> OTHER INFORMATION: modified ccGFP polypeptide (#5)

<400> SEQUENCE: 8

Met Ser Met Ser Lys Gln Val Leu Lys Glu Asp Met Lys Met Thr Tyr
1               5                   10                  15

His Met Asp Gly Ser Val Asn Gly His Tyr Phe Thr Ile Glu Gly Glu
            20                  25                  30

Gly Thr Gly Asn Pro Phe Lys Gly Gln Gln Thr Leu Lys Leu Arg Val
            35                  40                  45

Thr Lys Gly Gly Pro Leu Pro Phe Ala Phe Asp Ile Leu Ser Pro Thr
    50                  55                  60

Phe Thr Tyr Gly Asn Arg Val Phe Thr Asp Tyr Pro Glu Asp Met Pro
```

```
65                  70                  75                  80

Asp Tyr Phe Lys Gln Ser Leu Pro Glu Gly Tyr Ser Trp Glu Arg Thr
                85                  90                  95

Met Met Tyr Asp Asp Gly Ala Ser Ala Thr Ala Ser Ala Arg Ile Ser
                100                 105                 110

Leu Asp Lys Asn Gly Phe Val His Lys Ser Thr Phe His Gly Glu Asn
            115                 120                 125

Phe Pro Ala Asn Gly Pro Val Met Lys Lys Gly Val Asn Trp Glu
    130                 135                 140

Pro Ser Ser Glu Thr Ile Thr Ala Ser Asp Gly Ile Leu Lys Gly Asp
145                 150                 155                 160

Val Thr Met Phe Leu Val Leu Glu Gly Gly Gln Arg Leu Lys Ala Leu
                165                 170                 175

Phe Gln Thr Thr Tyr Lys Ala Asn Lys Val Val Lys Met Pro Pro Arg
                180                 185                 190

His Lys Ile Glu His Arg Leu Val Arg Ser Glu Asp Gly Glu Thr Ile
            195                 200                 205

Gln Leu Gln Glu His Ala Val Ala Lys Tyr Phe Thr Glu
    210                 215                 220

<210> SEQ ID NO 9
<211> LENGTH: 221
<212> TYPE: PRT
<213> ORGANISM: Artificial Sequence
<220> FEATURE:
<223> OTHER INFORMATION: modified ccGFP polypeptide (#7)

<400> SEQUENCE: 9

Met Ser Met Ser Lys Gln Val Leu Lys Glu Asn Met Lys Thr Thr Tyr
1               5                   10                  15

His Met Asp Gly Ser Val Asn Gly His Tyr Phe Thr Ile Glu Gly Glu
                20                  25                  30

Gly Thr Gly Asn Pro Phe Lys Gly Gln Gln Ser Leu Lys Leu Arg Val
            35                  40                  45

Thr Lys Gly Gly Pro Leu Pro Phe Ala Phe Asp Ile Leu Ser Pro Thr
    50                  55                  60

Phe Thr Tyr Gly Asn Arg Val Phe Thr Asp Tyr Pro Glu Tyr Met Pro
65                  70                  75                  80

Asp Tyr Phe Lys Arg Ser Leu Pro Glu Gly Tyr Ser Trp Glu Arg Thr
                85                  90                  95

Met Met Tyr Glu Asp Gly Ala Thr Ala Thr Ala Ser Val Arg Ile Ser
                100                 105                 110

Leu Asp Lys Asn Gly Phe Val His Lys Ser Thr Phe His Gly Glu Asn
            115                 120                 125

Phe Pro Ala Asn Gly Pro Val Met Lys Lys Lys Gly Val Asn Trp Glu
    130                 135                 140

Pro Ser Ser Glu Thr Ile Thr Pro Ser Asp Gly Ile Leu Lys Gly Asp
145                 150                 155                 160

Val Thr Met Phe Leu Val Leu Glu Gly Gly Gln Arg Leu Lys Ala Leu
                165                 170                 175

Phe Gln Thr Thr Tyr Lys Ala Asn Lys Val Val Lys Met Pro Pro Arg
                180                 185                 190

His Lys Ile Glu His Arg Leu Val Arg Ser Glu Asp Gly Glu Thr Ile
            195                 200                 205

Gln Leu Gln Glu His Ala Val Ala Lys Tyr Phe Thr Glu
```

```
              210                 215                 220
```

```
<210> SEQ ID NO 10
<211> LENGTH: 202
<212> TYPE: PRT
<213> ORGANISM: Artificial Sequence
<220> FEATURE:
<223> OTHER INFORMATION: ccGFP 1-10 E6 polypeptide

<400> SEQUENCE: 10

Met Ser Met Ser Lys Gln Val Leu Lys Glu Asp Met Lys Met Thr Tyr
1               5                   10                  15

His Met Asp Gly Ser Val Asn Gly His Tyr Phe Thr Ile Glu Gly Glu
            20                  25                  30

Gly Thr Gly Asn Pro Phe Lys Gly Gln Gln Thr Leu Lys Leu Arg Val
        35                  40                  45

Thr Lys Gly Gly Pro Leu Pro Phe Ala Phe Asp Ile Leu Ser Pro Thr
    50                  55                  60

Phe Thr Tyr Gly Asn Arg Val Phe Thr Asp Tyr Pro Glu Asp Met Pro
65                  70                  75                  80

Asp Tyr Phe Lys Gln Ser Leu Pro Glu Gly Tyr Ser Trp Glu Arg Thr
                85                  90                  95

Met Met Tyr Asp Asp Gly Ala Ser Ala Thr Ala Ser Ala Arg Ile Ser
            100                 105                 110

Leu Asp Lys Asn Gly Phe Val His Lys Ser Thr Phe His Gly Glu Asn
        115                 120                 125

Phe Pro Ala Asn Gly Pro Val Met Lys Lys Lys Gly Val Asn Trp Glu
    130                 135                 140

Pro Ser Ser Glu Thr Ile Thr Ala Ser Asp Gly Ile Leu Lys Gly Asp
145                 150                 155                 160

Val Thr Met Phe Leu Val Leu Glu Gly Gly Gln Arg Leu Lys Ala Leu
                165                 170                 175

Phe Gln Thr Thr Tyr Lys Ala Asn Lys Val Val Lys Met Pro Pro Arg
            180                 185                 190

His Lys Ile Glu His Arg Leu Val Arg Ser
        195                 200

<210> SEQ ID NO 11
<211> LENGTH: 17
<212> TYPE: PRT
<213> ORGANISM: Artificial Sequence
<220> FEATURE:
<223> OTHER INFORMATION: split ccGFP S11 E6 polypeptide

<400> SEQUENCE: 11

Gly Asp Thr Val Gln Leu Gln Glu His Ala Val Ala Lys Tyr Phe Thr
1               5                   10                  15

Val

<210> SEQ ID NO 12
<211> LENGTH: 221
<212> TYPE: PRT
<213> ORGANISM: Corynactis californica

<400> SEQUENCE: 12

Met Ser Leu Ser Lys Gln Val Val Lys Glu Asp Met Lys Met Thr Tyr
1               5                   10                  15

His Met Asp Gly Cys Val Asn Gly His Tyr Phe Thr Ile Glu Gly Glu
            20                  25                  30
```

```
Gly Thr Gly Lys Pro Phe Lys Gly Gln Lys Thr Leu Lys Leu Arg Val
        35                  40                  45

Thr Glu Gly Gly Pro Leu Pro Phe Ala Phe Asp Ile Leu Ser Ala Thr
    50                  55                  60

Phe Thr Tyr Gly Asn Arg Cys Phe Cys Asp Tyr Pro Glu Asp Met Pro
65                  70                  75                  80

Asp Tyr Phe Lys Gln Ser Leu Pro Glu Gly Tyr Ser Trp Glu Arg Thr
                85                  90                  95

Met Met Tyr Glu Asp Gly Ala Cys Gly Thr Ala Ser Ala His Ile Ser
                100                 105                 110

Leu Asp Lys Asn Gly Phe Val His Asn Ser Thr Phe His Gly Val Asn
            115                 120                 125

Phe Pro Ala Asn Gly Pro Val Met Lys Lys Gly Val Asn Trp Glu
        130                 135                 140

Pro Ser Ser Glu Lys Ile Thr Ala Cys Asp Gly Ile Leu Lys Gly Asp
145                 150                 155                 160

Val Thr Met Phe Leu Val Leu Glu Gly Gly His Arg Leu Lys Cys Leu
                165                 170                 175

Phe Gln Thr Thr Tyr Lys Ala Asp Lys Val Val Lys Met Pro Pro Asn
            180                 185                 190

His Ile Ile Glu His Arg Leu Val Arg Ser Glu Asp Gly Asp Ala Val
            195                 200                 205

Gln Ile Gln Glu His Ala Val Ala Lys Tyr Phe Thr Val
    210                 215                 220

<210> SEQ ID NO 13
<211> LENGTH: 221
<212> TYPE: PRT
<213> ORGANISM: Artificial Sequence
<220> FEATURE:
<223> OTHER INFORMATION: ccGFP m

<400> SEQUENCE: 13

Met Ser Leu Ser Lys Gln Val Val Lys Glu Asp Met Lys Met Thr Tyr
1               5                   10                  15

His Met Asp Gly Cys Val Asn Gly His Tyr Phe Thr Ile Glu Gly Glu
                20                  25                  30

Gly Thr Gly Lys Pro Phe Lys Gly Gln Lys Thr Leu Lys Leu Arg Val
        35                  40                  45

Thr Glu Gly Gly Pro Leu Pro Phe Ala Phe Asp Ile Leu Ser Ala Thr
    50                  55                  60

Phe Thr Tyr Gly Asn Arg Cys Phe Cys Asp Tyr Pro Glu Asp Met Pro
65                  70                  75                  80

Asp Tyr Phe Lys Gln Ser Leu Pro Glu Gly Tyr Ser Trp Glu Arg Thr
                85                  90                  95

Met Met Tyr Glu Asp Gly Ala Cys Gly Thr Ala Ser Ala His Ile Ser
                100                 105                 110

Leu Asp Lys Asn Gly Phe Val His Asn Ser Thr Phe His Gly Glu Asn
            115                 120                 125

Phe Pro Ala Asn Gly Pro Val Met Lys Lys Gly Val Asn Trp Glu
        130                 135                 140

Pro Ser Ser Glu Lys Ile Thr Ala Cys Asp Gly Ile Leu Lys Gly Asp
145                 150                 155                 160

Val Thr Met Phe Leu Val Leu Glu Gly Gly His Arg Leu Lys Cys Leu
                165                 170                 175
```

```
Phe Gln Thr Thr Tyr Lys Ala Asp Lys Val Val Lys Met Pro Pro Arg
            180                 185                 190

His Glu Ile Glu His Arg Leu Val Arg Ser Glu Asp Gly Asp Ala Val
            195                 200                 205

Gln Ile Gln Glu His Ala Val Ala Lys Tyr Phe Thr Val
    210                 215                 220

<210> SEQ ID NO 14
<211> LENGTH: 221
<212> TYPE: PRT
<213> ORGANISM: Artificial Sequence
<220> FEATURE:
<223> OTHER INFORMATION: ccGFP syn

<400> SEQUENCE: 14

Met Ser Leu Ser Lys Gln Val Val Lys Glu Asp Met Lys Met Thr Tyr
1               5                   10                  15

His Met Asp Gly Cys Val Asn Gly His Tyr Phe Thr Ile Glu Gly Glu
            20                  25                  30

Gly Thr Gly Lys Pro Phe Lys Gly Gln Lys Thr Leu Lys Leu Arg Val
            35                  40                  45

Thr Glu Gly Gly Pro Leu Pro Phe Ala Phe Asp Ile Leu Ser Ala Thr
    50                  55                  60

Phe Thr Tyr Gly Asn Arg Cys Phe Cys Asp Tyr Pro Glu Asp Met Pro
65                  70                  75                  80

Asp Tyr Phe Lys Gln Ser Leu Pro Glu Gly Tyr Ser Trp Glu Arg Thr
                85                  90                  95

Met Met Tyr Glu Asp Gly Ala Cys Gly Thr Ala Ser Ala His Ile Ser
            100                 105                 110

Leu Asp Lys Asn Gly Phe Val Gln Lys Ser Thr Phe His Gly Glu Asn
            115                 120                 125

Phe Pro Ala Asn Gly Pro Val Met Lys Lys Lys Gly Val Asn Trp Glu
    130                 135                 140

Pro Ser Ser Glu Lys Ile Thr Ala Cys Asp Gly Ile Leu Lys Gly Asp
145                 150                 155                 160

Val Thr Met Phe Leu Val Leu Glu Gly Gly His Arg Leu Lys Cys Leu
                165                 170                 175

Phe Gln Thr Thr Tyr Lys Ala Asp Lys Val Val Lys Met Pro Pro Arg
            180                 185                 190

His Glu Ile Glu His Arg Leu Val Arg Ser Glu Asp Gly Asp Ala Val
            195                 200                 205

Gln Ile Gln Glu His Ala Val Ala Lys Tyr Phe Thr Val
    210                 215                 220

<210> SEQ ID NO 15
<211> LENGTH: 606
<212> TYPE: DNA
<213> ORGANISM: Artificial Sequence
<220> FEATURE:
<223> OTHER INFORMATION: nucleic acid sequence encoding ccGFP 1-10
      version 1

<400> SEQUENCE: 15
atgtctatgt caaaacaagt gctcaaagaa aacatgaaaa cgacttatca catggacggt        60
tcggtgaacg ggcattattt cacgatagaa ggtgaaggga ctgggaaccc atttaaaggc       120
caacagtcct tgaaattacg cgttacgaag gggggcccgc ttccgtttgc atttgatatc       180
```

-continued

```
ctgagtccca cttttaccta cgggaatcgt gtttttcactg attatcccga ggatatgcca    240
gattacttca agcagagtct accagaggga tactcatggg aacgaaccat gatgtatgaa    300
gacggagcca cggccacggc ctcagcgcgt atatctttag acaaaaacgg cttcgtacat    360
aaaagcacct ttcatggtga gaacttccct gcaaatggac cagtaatgaa gaagaagggg    420
gtaaactggg aaccgtcttc agagacgata actccttcgg atggcattct caaaggggat    480
gtcaccatgt tccttgtatt agaaggaggg caacgcttga aggctttgtt tcagaccaca    540
tataaggcta acaaagttgt caaaatgccg ccacgccaca agatcgaaca caggctagtg    600
cgctct                                                                606
```

```
<210> SEQ ID NO 16
<211> LENGTH: 606
<212> TYPE: DNA
<213> ORGANISM: Artificial Sequence
<220> FEATURE:
<223> OTHER INFORMATION: nucleic acid sequence encoding ccGFP 1-10
      version 2

<400> SEQUENCE: 16
atgtctatgt caaaacaagt gctcaaagaa aacatgaaaa cgacttatca catggacggt     60
tcggtgaacg ggcattattt cacgatagaa ggtgaaggga ctgggaaccc atttaaaggc    120
caacagtcct tgaaattacg cgttacgaag gggggcccgc ttccgtttgc atttgatatc    180
ctgagtccca cttttaccta cgggaatcgt gtttttcactg attatcccga gtatatgcca    240
gattacttca agcggagtct accagaggga tactcatggg aacgaaccat gatgtatgaa    300
gacggagcca cggccacggc ctcagtgcgt atatctttag acaaaaacgg cttcgtacat    360
aaaagcacct ttcatggtga gaacttccct gcaaatggac cagtaatgaa gaagaagggg    420
gtaaactggg aaccgtcttc agagacgata actccttcgg atggcattct caaaggggat    480
gtcaccatgt tccttgtatt agaaggaggg caacgcttga aggctttgtt tcagaccaca    540
tataaggcta acaaagttgt caaaatgccg ccacgccaca agatcgaaca caggctagtg    600
cgctca                                                                606
```

```
<210> SEQ ID NO 17
<211> LENGTH: 606
<212> TYPE: DNA
<213> ORGANISM: Artificial Sequence
<220> FEATURE:
<223> OTHER INFORMATION: nucleic acid sequence encoding ccGFP 1-10
      version 3

<400> SEQUENCE: 17
atgtctatgg aaaaacaagt gctcaaagaa aacatgaaaa cgacttatca catggacggt     60
tcggtggatg ggcattattt cgaaatagaa ggtgaaggga ctgggaaccc atttaaaggc    120
gaacaggaat tgaaattacg cgttacgaag gggggcccgc ttccgttcgc atttgatatc    180
ctgagtccca cttttaccta cgggaatcgt gtttttcactg attatcccga ggatatgccc    240
gattacttca agcagagtct accagaggga tactcatggg aacgaaccat gatgtatgaa    300
gacggagcca cggccacggc ctcagcgcgt atatctttag acaaaaacgg cttcgtacat    360
aaaagcacct ttcatggaga gaacttcccc gcaaatggac cagtaatgaa gaaaaagggg    420
gtagattggg aaccgtcttc agagacgata actcctgaag atggcattct caaagggggat    480 gtcgaaatgt tccttgtatt agaaggaggg caacgcttga aggctttgtt tcagaccaca    540
tataaggcta acaaagttgt caaaatgccg ccacgccaca agatcgaaca caggctagtg    600
```

-continued

```
cgctct                                              606

<210> SEQ ID NO 18
<211> LENGTH: 51
<212> TYPE: DNA
<213> ORGANISM: Artificial Sequence
<220> FEATURE:
<223> OTHER INFORMATION: nucleic acid sequence encoding ccGFP S11

<400> SEQUENCE: 18
ggggagacta tacagctcca ggagcacgca gtcgctaaat atttcacgga a          51
```

FLUORESCENT PROTEINS AND SPLIT FLUORESCENT PROTEINS FROM CORYNACTIS CALIFORNICA AND METHODS OF USE

CROSS REFERENCE TO RELATED APPLICATION

This application claims the benefit of U.S. Provisional Patent Application No. 63/181,449, filed on Apr. 29, 2021, which is incorporated herein by reference in its entirety.

ACKNOWLEDGMENT OF GOVERNMENT SUPPORT

This invention was made with government support under Contract No. 89233218CNA000001 awarded by the U.S. Department of Energy/National Nuclear Security Administration and Grant No. 5P01GM098177-02 awarded by the National Institutes of Health. The government has certain rights in the invention.

FIELD

The present disclosure relates generally to compositions for improved fluorescent based protein-protein interaction and protein solubility detection methods.

BACKGROUND

Fluorescent proteins such as green fluorescent protein (GFP) from the Pacific Northwest jellyfish, *Aequorea victoria*, form a three-dimensional structure including eleven anti-parallel outer beta strands and one inner alpha strand. Several natural and engineered GFP variants are known, including variants that exhibit altered fluorescent properties.

Split Fluorescent Proteins (SFPs) are composed of multiple fragments of the eleven anti-parallel outer β-strands and one inner α-strand of a fluorescent protein. Individually, the fragments are not fluorescent, but when complemented, they form a functional fluorescent molecule. Typically, the SFP includes a first fragment known as an "SFP detector" that includes nine or ten contiguous β-strands and the α-strand of the fluorescent protein or a circular permutant thereof, and one or two separate fragments known as the "SFP tag(s)" that include the remaining β-strand or strands. Some tripartite SFP systems are known, which include three separate proteins that can form a fluorescent protein. For example, a tripartite split-Green Fluorescent Protein (split-GFP) system can include an SFP detector including GFP β-strands 1-9 (GFP1-9), a first SFP tag including GFP β-strand 10 (GFP10), and a second SFP tag including GFP β-strand 11 (GFP11). The GFP10 and GFP11 tags can be placed on unrelated polypeptide sequences and detected using the GFP1-9 detector. However, known split-GFP systems exhibit poor assembly characteristics, poor stability, and/or high background fluorescence. Thus, there is a need for fluorescent proteins with improved folding, stability, and solubility characteristics.

Recent work shows the utility of split fluorescent proteins for large scale labeling of proteins in cells using CRISPR. However, in order to make split fluorescent protein labeling of proteins in living cells widely applicable, several technical advances are needed, including new approaches to insert the split protein tags, faster complementing split fluorescent proteins, and additional orthogonal split fluorescent proteins that do not "cross-react" (e.g., the large detector fragment from one does not efficiently bind and fold with the small beta strand fragment from another) and that have spectrally-distinct colors.

SUMMARY

Provided herein are SFP detector and tag polypeptides. In some embodiments, a SFP detector polypeptide includes an amino acid sequence having at least 95% sequence identity to SEQ ID NO: 1, wherein amino acid residue 11 is asparagine, amino acid residue 14 is threonine, amino acid residue 43 is serine, amino acid residue 100 is glutamic acid, amino acid residue 104 is threonine, and amino acid residue 152 is proline, and wherein the SFP detector complements with an SFP tag to form a functional SFP. In particular examples, the SFP detector polypeptide further includes a tyrosine at amino acid residue 78, an arginine at amino acid residue, and a valine at amino acid residue 109. In other embodiments, a SFP detector polypeptide includes an amino acid sequence having at least 95% sequence identity to SEQ ID NO: 3, wherein amino acid residue 4 is glutamic acid, amino acid residue 11 is asparagine, amino acid residue 14 is threonine, amino acid residue 23 is aspartic acid, amino acid residue 28 is glutamic acid, amino acid residue 41 is glutamic acid, amino acid residue 43 is glutamic acid, amino acid residue 100 is glutamic acid, amino acid residue 104 is threonine, amino acid residue 142 is aspartic acid, amino acid residue 152 is proline, amino acid residue 153 is glutamic acid, and amino acid residue 162 is glutamic acid, and wherein the SFP detector complements with an SFP tag to form a functional SFP. In some examples, the SFP polypeptide includes or consists of the amino acid sequence of any one of SEQ ID NOs: 1-3.

In some embodiments a SFP tag polypeptide includes an amino acid sequence having at least 95% sequence identity to SEQ ID NO: 4, wherein amino acid residue 2 is glutamic acid, amino acid 4 is isoleucine, and amino acid 17 is glutamic acid, and wherein the SFP tag complements with an SFP detector to form a functional SFP. In some examples, the SFP polypeptide includes or consists of the amino acid sequence of SEQ ID NO: 4.

Also provided are fusion polypeptides including a disclosed SFP detector polypeptide or SFP tag polypeptide linked to a protein of interest. In some examples, the SFP detector or tag polypeptide is linked to the protein of interest via a peptide linker.

Also provided are green fluorescent proteins including an amino acid sequence having at least 95% sequence identity to SEQ ID NO: 8, wherein amino acid residue 206 is glutamic acid, amino acid residue 208 is isoleucine, and amino acid residue 221 is glutamic acid. In some examples, the GFP further includes an asparagine at amino acid residue 11, a threonine at amino acid residue 14, a serine at amino acid residue 43, a glutamic acid at amino acid residue 100, a threonine at amino acid residue 104, and a proline at amino acid residue 152. In further examples, the GFP also includes a tyrosine at amino acid residue 78, an arginine at amino acid residue 85, and a valine at amino acid residue 109. In other embodiments, provided is a green fluorescent protein including an amino acid sequence having at least 95% sequence identity to SEQ ID NO: 7, wherein amino acid residue 4 is glutamic acid, amino acid residue 11 is asparagine, amino acid residue 14 is threonine, amino acid residue 23 is aspartic acid, amino acid residue 28 is glutamic acid, amino acid residue 41 is glutamic acid, amino acid residue 43 is glutamic acid, amino acid residue 100 is glutamic acid, amino acid residue 104 is threonine, amino acid residue 142 is aspartic acid, amino acid residue 152 is proline, amino acid residue 153 is glutamic acid, amino acid residue 162 is glutamic acid, amino acid residue 206 is glutamic acid, amino acid residue 208 is isoleucine, and amino acid residue 221 is glutamic acid. In some examples, the GFP polypeptide includes or consists of the amino acid sequence of any one of SEQ ID NOs: 6-9.

Also provided are nucleic acid molecules encoding the disclosed polypeptides. In some examples, the nucleic acid molecule includes a nucleic acid sequence with at least 90% sequence identity to any one of SEQ ID NOs: 15-18. In other examples, the nucleic acid molecule includes or consists of the nucleic acid sequence of any one of SEQ ID NOs: 15-18.

In some embodiments, the disclosed nucleic acid molecules are included in a recombinant vector. In some examples, the nucleic acid molecule is operably linked to a heterologous promoter. In some examples, the heterologous promoter is a promoter from *E. coli*, a viral promoter, or a mammalian promoter. In additional embodiments, provided herein are host cells including the nucleic acid molecule or the recombinant vector. In some examples, the host cell is a bacterial cell (such as *E. coli*), a fungal cell, or a mammalian cell.

Also provided are kits including one or more of the disclosed polypeptides, nucleic acid molecules, recombinant vectors, or host cells.

In some embodiments, a split-fluorescent protein system, including at least two polypeptide fragments of a fluorescent protein is provided. In some examples, the system includes a first polypeptide comprising a disclosed SFP detector polypeptide (e.g., one of SEQ ID NOs: 1-3) and a second polypeptide comprising a disclosed SFP tag polypeptide (e.g., SEQ ID NO: 4). In some examples, the at least two polypeptide fragments together contain the full complement of beta-strands in the fluorescent protein, for example, the at least two polypeptide fragments spontaneously self-complement to reconstitute the fluorescent protein and fluorescent phenotype. In some examples, the second polypeptide is operably linked to a protein of interest to form a fusion polypeptide, which fusion polypeptide spontaneously self-complements with the first polypeptide if the protein of interest is soluble.

Also provided herein are methods of detecting a protein of interest. In some embodiments, the methods include providing a disclosed SFP detector polypeptide (such as one of SEQ ID NOs: 1-3) and a SFP tag polypeptide (such as SEQ ID NO: 4) which is linked to the protein of interest, wherein the SFP detector and SFP tag complement to form a fluorescent protein complex; and detecting fluorescence of the fluorescent protein complex, thereby detecting the protein of interest. In some examples, the SFP detector and the SFP tag linked to the protein of interest are expressed from one or more expression vectors in a host cell. In some examples, the SFP detector and the SFP tag linked to the protein of interest are each expressed from an independently inducible promoter. In some examples, the methods further include culturing the host cell under baseline conditions permitting the repression of both of the independently inducible promoters; inducing the expression of the SFP tag-protein of interest fusion for a time sufficient to permit expression of the fusion protein and permit the expressed fusion protein to aggregate if insoluble; and inducing the expression of the SFP detector for a time sufficient to permit expression of the SFP detector and its self-complementation with the SFP tag-protein of interest fusion protein, thereby detecting the soluble protein of interest.

Also provided are methods of detecting interaction between a first polypeptide and a second polypeptide. In some embodiments, the methods include providing a SFP detector polypeptide (such as one of SEQ ID NOs: 1-3) linked to the first polypeptide and a SFP tag polypeptide (such as SEQ ID NO: 4) linked to the second polypeptide, wherein the SFP detector and SFP tag complement to form a fluorescent protein complex on interaction between the first polypeptide and the second polypeptide; and detecting fluorescence of the fluorescent protein complex, thereby detecting the interaction between the first polypeptide and the second polypeptide. In some examples the SFP detector linked to the first polypeptide and the SFP tag linked to the second polypeptide are expressed from one or more expression vectors in a host cell.

Also provided are methods for quantifying a protein of interest in vitro. In some embodiments, the methods include providing a polynucleotide construct comprising the coding sequence of a SFP tag (such as SEQ ID NO: 4), fused to the coding sequence of the protein of interest; culturing a cell containing the construct under conditions permitting the expression of the SFP tag-protein of interest fusion protein encoded by the construct for a time sufficient to permit expression of the fusion protein and permit the expressed fusion protein to aggregate if insoluble; lysing the cell and solubilizing the total protein in the lysate by chemical denaturation; renaturing the solubilized protein in the lysate in a suitable diluent containing an SFP detector, wherein the SFP detector and SFP tag complement to form a fluorescent protein complex, under conditions and for a time sufficient to allow self-complementation; and, quantitatively detecting fluorescence to determine the quantity of the protein of interest.

Methods for determining the total quantity of a protein of interest in vivo are also provided. In some embodiments, the methods include providing a first polynucleotide construct comprising the coding sequence of a SFP tag (such as SEQ ID NO: 4), fused to the coding sequence of the protein of interest; providing a second polynucleotide construct comprising the coding sequence of a SFP detector wherein the SFP detector and the SFP tag complement to form a fluorescent protein complex; culturing a cell containing the first and second constructs under conditions permitting the expression of the SFP tag-protein of interest fusion protein encoded by the first construct and the SFP detector encoded by the second construct for a time sufficient to permit self-complementation of the SFP tag and SFP detector; and quantitatively detecting fluorescence to determine the quantity of the protein of interest.

Also provided are methods for detecting a soluble or insoluble protein of interest in vitro. In some embodiments a method for detecting a soluble protein of interest in vitro includes providing a polynucleotide construct comprising the coding sequence of a SFP tag (such as SEQ ID NO: 4), fused to the coding sequence of the protein of interest; culturing a cell containing the construct under conditions permitting the expression of the SFP tag-protein of interest fusion encoded by the construct for a time sufficient to permit expression of the fusion protein and permit the expressed fusion protein to aggregate if insoluble; lysing the cell and contacting the lysate with an SFP detector (such as one of SEQ ID NOs: 1-3), wherein the SFP detector and SFP tag complement to form a fluorescent protein complex, under conditions and for a time sufficient to allow self-complementation; and detecting fluorescence, wherein the presence of detectable fluorescence provides an indication that the test protein is soluble.

In other embodiments, a method of quantifying insoluble protein of interest in vitro includes providing a polynucleotide construct comprising the coding sequence of a SFP tag (such as SEQ ID NO: 4), fused to the coding sequence of the protein of interest; culturing a cell containing the construct under conditions permitting the expression of the SFP tag-protein of interest fusion encoded by the construct for a time sufficient to permit expression of the fusion protein and permit the expressed fusion protein to aggregate if insoluble; lysing the cell and isolating the insoluble fraction therefrom; solubilizing the insoluble fraction by chemical denaturation; renaturing the solubilized denatured insoluble protein fraction in a suitable diluent containing an SFP detector (such as one of SEQ ID NOs: 1-3), wherein the SFP detector and SFP tag complement to form a fluorescent protein complex, under conditions and for a time sufficient to allow self-complementation; and quantitatively detecting fluorescence in order to determine the insoluble protein quantity.

The foregoing and other features of the disclosure will become more apparent from the following detailed description, which proceeds with reference to the accompanying figures.

BRIEF DESCRIPTION OF THE DRAWINGS

(FIG. 1A) Sequences leading up to the well-folded ccGFP E6. Legend: ccGFP wt, starting sequence GenBank accession number AAZ14788.1 (SEQ ID NO: 12); ccGFP m, monomerizing mutations (SEQ ID NO: 13); ccGFP syn, synthetic sequence containing the monomerizing mutations and additional mutations H120Q, N121K (SEQ ID NO: 14); ccGFP E6, optimal mutant after six rounds of gene shuffling to improve folding, and three additional rounds of gene shuffling after replacing cysteine residues with alanine or serine (SEQ ID NO: 5). (FIG. 1B) Split protein fragments for strands 1-and S11 used in this study, showing the starting versions derived from ccGFP E6 and the indicated mutants. ccGFP 1-10 E6 (SEQ ID NO: 10), ccGFP 1-10 v1 (SEQ ID NO: 1), ccGFP 1-10 v2 (SEQ ID NO: 2), ccGFP 1-10 v3 (SEQ ID NO: 3), ccGFP S11 E6 (SEQ ID NO: 11), ccGFP S11 (SEQ ID NO: 4).

(FIG. 2A) Progress curves for in vitro complementation after mixing indicated ccGFP 1-10 variant (800 μmol) with SR-ccGFP S11 (50 μmol) in 200 μl reaction wells (upper traces); development of autofluorescence of each ccGFP 1-10 without added S11 ('no S11,' lower traces). Due to lack of chromophore residues, S11 fragments are not autofluorescent, as expected (not shown). Maximum arbitrary scale signal (~0.8) corresponds to 45,000 fluorescence units on BioTek instrument (99,999 full scale). Progress curves were normalized by dividing measured fluorescence by the fluorescence of a sodium fluorescein control (nominally 60,000 fluorescence units) to compensate for instrument drift and jitter noise. Typical background signal (buffer only) is less than ~100 fluorescence units on a scale of 99,999 full scale. (FIG. 2B) Normalized progress curves for indicated ccGFP 1-10 variant from FIG. 2A after subtraction of progress curve of corresponding ccGFP 1-10 fragments alone ('no S11'). (FIG. 2C) In vitro complementation of equal molar amounts of ccGFP S11 variants (50 μmol) with ccGFP 1-10 v2 (800 μmol) in 200 μl reaction wells.

(FIG. 3A) Superimposition of scaled progress curves for complementation of 200, 100, 50, 25. 12.5, 6.25, 3.13 and 1.56 pmol SR-ccGFP S11 in 20 μl aliquots, mixed with 180 μl aliquots containing 800 pmol of ccGFP 1-10 v2. Maximum signal (~0.8) corresponds to 45,000 fluorescence units on BioTek instrument scale (99, 999 full scale). Progress curves were normalized by dividing by the fluorescence of a sodium fluorescein control (nominally 60,000 fluorescence units) to compensate for instrument baseline drift. The curves can be superimposed by linear scaling indicating that the shape of the progress curve does not depend on the concentration of the tagged protein or depletion of the pool of unbound ccGFP 1-10 fragment. Note, in the superposition (top), noisy traces naturally result from the required scaling of the lowest concentration progress curves. (FIG. 3B) In vitro sensitivity of SR-ccGFP S11 complementation with ccGFP 1-10 v2. Values of progress curves at 1 h from FIG. 3A are plotted vs. concentration of SR-ccGFP S11. (FIG. 3C) Same as FIG. 3B, but data from FIG. 3A taken at 6 min.

(FIG. 7A) Progress curves for complementation of 200, 100, 50, 25, 12.5, 6.25, 3.13 and 1.56 pmol SR-ccGFP S11 in 20 µl aliquots, mixed with 180 µl aliquots containing 800 pmol of high autofluorescence variant ccGFP 1-10 v1 in 200 µl reaction wells. (FIG. 7B) Same progress curves in FIG. 7A after subtraction of the blank progress curve (labeled 0 µmol) in FIG. 7A. (FIG. 7C) In vitro sensitivity of SR-ccGFP S11 complementation with ccGFP 1-10 v1 after background subtraction, that is the 6 h data in FIG. 7B. (FIG. 7D) Same as FIG. 7C, but data taken from FIG. 7B at 6 min.

(FIG. 8A) Progress curves for complementation of 200, 100, 50, 25, 12.5, 6.25. 3.13 and 1.56 pmol SR-ccGFP S11 in 20 µl aliquots, mixed with 180 µl aliquots containing 800 pmol of −8 charged ccGFP 1-10 v3 in 200 µl reaction wells. (FIG. 8B) Same progress curves in FIG. 8A after subtraction of the blank progress curve (labeled 0 µmol) in FIG. 8A. (FIG. 8C) In vitro sensitivity of SR-ccGFP S11 complementation with ccGFP 1-10 v3 after background subtraction, that is the 8 h data in FIG. 8B. (FIG. 8D) Same as FIG. 8C, but data taken from FIG. 8B at 15 min.

(FIG. 12A) Equilibrium unfolding plots (fraction of initial fluorescence) for GdnHCI-denatured ccGFP variants as a function of the final concentration of GdnHCI in buffer. Proteins are (left to right): SF GFP (o), and the ccGFP variants #7 (♦) ccGFP #5 (▲), E6 (•), #9 (■) and #8 (Δ). Equilibrium fluorescence normalized by dividing by fluorescence of corresponding nondenatured samples diluted in parallel. (FIG. 12B) Dependence of the standard free energy of denaturation on urea concentration assuming a two-state folding model for the fluorescent proteins (see Table 4).

(FIG. 13A) Equilibrium unfolding plots (fraction of initial fluorescence) for GdnHCI-denatured GFP and ccGFP variants as a function of the final concentration of GdnHCI in buffer. Proteins are (left to right): SF GFP (o), and the ccGFP variants #7 (♦), #5 (▲), E6 (•). #9 (■) and #8 (Δ). Equilibrium fluorescence normalized by dividing by fluorescence of corresponding nondenatured samples diluted in parallel. (FIG. 13B) Dependence of the standard free energy of denaturation on urea concentration assuming a two-state folding model for the fluorescent proteins (see Table 2).

(FIG. 14A) Three-exponential fit to short term ccGFP E6 refolding progress curve, showing residual (data-fit)×4. RMSD=2802. (FIG. 14B) Three-exponential fit to medium term ccGFP E6 refolding progress curve, showing residual (data-fit)×4. RMSD=3035. (FIG. 14C) Three-exponential fit to long term ccGFP E6 refolding progress curve, showing residual (data-fit)×4. RMSD=1356.

(FIG. 15A) Three-exponential fit to short term ccGFP #5 refolding progress curve, showing residual (data-fit)×4. RMSD=3351. (FIG. 15B) Three-exponential fit to medium term ccGFP #5 refolding progress curve, showing residual (data-fit) 4. RMSD=5547. (FIG. 15C) Three-exponential fit to long term ccGFP #5 refolding progress curve, showing residual (data-fit)×4. RMSD=1097. Data from 2000-7500 s omitted due to uncorrected baseline drift, and was not included in the fit.

(FIG. 16A) Three-exponential fit to short term ccGFP #8 refolding progress curve, showing residual (data-fit)×4. RMSD=1368. (FIG. 16B) Three-exponential fit to medium term ccGFP #8 refolding progress curve, showing residual (data-fit)×4. RMSD=2161. (FIG. 16C) Three-exponential fit to long term ccGFP #8 refolding progress curve, showing residual (data-fit)×4. RMSD=1887.

(FIG. 17A) Two-exponential fit to short term ccGFP #8 refolding progress curve, showing residual (data-fit)×4. RMSD=2901. (FIG. 17B) Two-exponential fit to medium term ccGFP #8 refolding progress curve, showing residual (data-fit)×4. RMSD=4788. (FIG. 17C) Two-exponential fit to long term ccGFP #8 refolding progress curve, showing residual (data-fit)×4. RMSD=3691.

(FIG. 18A) Three-exponential fit to short term ccGFP #7 refolding progress curve, showing residual (data-fit)×4. RMSD=3522. (FIG. 18B) Three-exponential fit to medium term ccGFP #7 refolding progress curve, showing residual (data-fit)×4. RMSD=3383. (FIG. 18C) Three-exponential fit to long term ccGFP #7 refolding progress curve, showing residual (data-fit)×4. RMSD=771. Data from 2000-7500 s omitted due to uncorrected baseline drift, and was not included in the fit.

FIGS. 19A-19C are graphs showing ccGFP #9 refolding. (FIG. 19A) Three-exponential fit to short term ccGFP #9 refolding progress curve, showing residual (data-fit)×4. RMSD=635. (FIG. 19B) Three-exponential fit to medium term ccGFP #9 refolding progress curve, showing residual (data-fit)×4. RMSD=1262. (FIG. 19C) Three-exponential fit to long term ccGFP #9 refolding progress curve, showing residual (data-fit)×4. RMSD=2659.

(FIG. 20A) Three-exponential fit to short term sfGFP refolding progress curve, showing residual (data-fit)×4. RMSD=2758. (FIG. 20B) Three-exponential fit to medium term sfGFP refolding progress curve, showing residual (data-fit)×4. RMSD=3066. (FIG. 20C) Three-exponential fit to long term sfGFP refolding progress curve, showing residual (data-fit)×4. RMSD=4664.

(FIG. 21A) Two-exponential fit to short term sfGFP refolding progress curve, showing residual (data-fit)× 4. RMSD=15147. (FIG. 21B) Two-exponential fit to medium term sfGFP refolding progress curve, showing residual (data-fit)×4. RMSD=8863. (FIG. 21C) Two-exponential fit to long term sfGFP refolding progress curve, showing residual (data-fit)×4. RMSD=5528.

(FIG. 22A) Three-exponential fit to short term GFP 1-10M3 refolding progress curve, showing residual (data-fit)×4. RMSD=1722. (FIG. 22B) Three-exponential fit to medium term GFP 1-10M3 refolding progress curve, showing residual (data-fit)×4. RMSD=3697. (FIG. 22C) Three-exponential fit to long term GFP 1-10M3 refolding progress curve, showing residual (data-fit)×4. RMSD=2317.

(FIG. 23A) Two-exponential fit to short term GFP 1-10M3 refolding progress curve, showing residual (data-fit)×4. RMSD=9422. (FIG. 23B) Two-exponential fit to medium term GFP 1-10M3 refolding progress curve, showing residual (data-fit)×4. RMSD=8560. (FIG. 23C) Two-exponential fit to long term GFP 1-10M3 refolding progress curve, showing residual (data-fit)×4. RMSD=2494.

SEQUENCE LISTING

Figure 1:
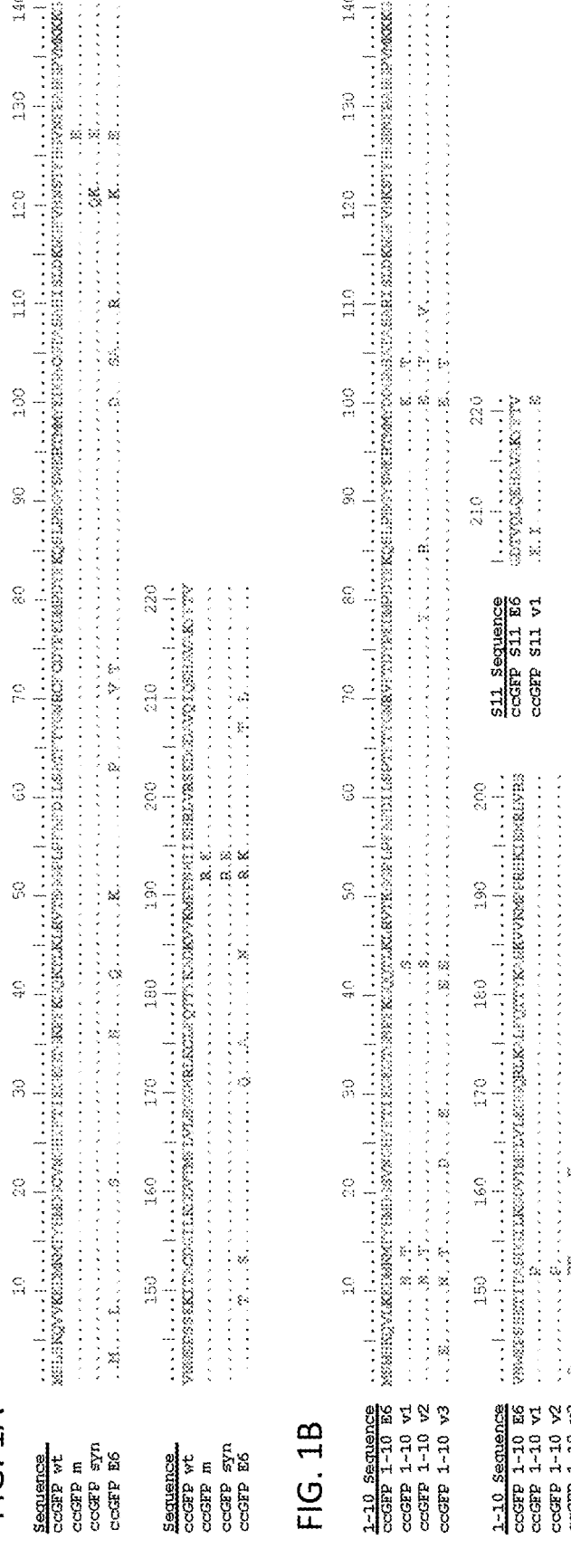
FIGS. 1A and 1B are sequence alignments of *Corynactis californica* GFPs.

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Apr. 28, 2022, and is 27,441 bytes, which is incorporated by reference herein.

SEQ ID NO: 1 is the amino acid sequence of a split ccGFP 1-10 polypeptide, version 1:

```
MSMSKQVLKENMKTTYHMDGSVNGHYFTIEGEGTGNPFKGQQSLKLRVT
KGGPLPFAFDILSPTFTYGNRVFTDYPEDMPDYFKQSLPEGYSWERTMM
YEDGATATASARISLDKNGFVHKSTFHGENFPANGPVMKKKGVNWEPSS
ETITPSDGILKGDVTMFLVLEGGQRLKALFQTTYKANKVVKMPPRHKIE
HRLVRS
```

SEQ ID NO: 2 is the amino acid sequence of a split ccGFP 1-10 polypeptide, version 2:

```
MSMSKQVLKENMKTTYHMDGSVNGHYFTIEGEGTGNPFKGQQSLKLRVT
KGGPLPFAFDILSPTFTYGNRVFTDYPEYMPDYFKRSLPEGYSWERTMM
YEDGATATASVRISLDKNGFVHKSTFHGENFPANGPVMKKKGVNWEPSS
ETITPSDGILKGDVTMFLVLEGGQRLKALFQTTYKANKVVKMPPRHKIE
HRLVRS
```

SEQ ID NO: 3 is the amino acid sequence of a split ccGPP 1-10 polypeptide, version 3:

```
MSMEKQVLKENMKTTYHMDGSVDGHYFEIEGEGTGNPFKGEQELKLRVT
KGGPLPFAFDILSPTFTYGNRVFTDYPEDMPDYFKQSLPEGYSWERTMM
```

-continued
```
YEDGATATASARISLDKNGFVHKSTFHGENFPANGPVMKKKGVDWEPSS
ETITPEDGILKGDVEMFLVLEGGQRLKALFQTTYKANKVVKMPPRHKIE
HRLVRS
```

SEQ ID NO: 4 is the amino acid sequence of a split ccGFP S11 polypeptide: GETIQLQEHAVAKYFTE

```
SEQ ID NO: 5 is the amino acid sequence of a
modified ccGFP E6 polypeptide:
MSMSKQVLKEDMKMTYHMDGSVNGHYFTIEGEGTGNPFKGQQTLKLRVT
KGGPLPFAFDILSPTFTYGNRVFTDYPEDMPDYFKQSLPEGYSWERTMM
YDDGASATASARISLDKNGFVHKSTFHGENFPANGPVMKKKGVNWEPSS
ETITASDGILKGDVTMFLVLEGGQRLKALFQTTYKANKVVKMPPRHKIE
HRLVRSEDGDTVQLQEHAVAKYFTV
```

SEQ ID NO: 6 is the amino acid sequence of a modified ccGPP polypeptide (#8):

```
MSMSKQVLKENMKTTYHMDGSVNGHYFTIEGEGTGNPFKGQQSLKLRVT
KGGPLPFAFDILSPTFTYGNRVFTDYPEDMPDYFKQSLPEGYSWERTMM
YEDGATATASARISLDKNGFVHKSTFHGENFPANGPVMKKKGVNWEPSS
ETITPSDGILKGDVTMFLVLEGGQRLKALFQTTYKANKVVKMPPRHKIE
HRLVRSEDGETIQLQEHAVAKYFTE
```

SEQ ID NO: 7 is the amino acid sequence of an additional modified ccGFP polypeptide (#9):

```
MSMEKQVLKENMKTTYHMDGSVDGHYFEIEGEGTGNPFKGEQELKLRVT
KGGPLPFAFDILSPTFTYGNRVFTDYPEDMPDYFKQSLPEGYSWERTMM
YEDGATATASARISLDKNGFVHKSTFHGENFPANGPVMKKKGVDWEPSS
ETITPEDGILKGDVEMFLVLEGGQRLKALFQTTYKANKVVKMPPRHKIE
HRLVRSEDGETIQLQEHAVAKYFTE
```

SEQ ID NO: 8 is the amino acid sequence of an additional modified ccGFP polypeptide:

```
MSMSKQVLKEDMKMTYHMDGSVNGHYFTIEGEGTGNPFKGQQTLKLRVT
KGGPLPFAFDILSPTFTYGNRVFTDYPEDMPDYFKQSLPEGYSWERTMM
YDDGASATASARISLDKNGFVHKSTFHGENFPANGPVMKKKGVNWEPSS
ETITASDGILKGDVTMFLVLEGGQRLKALFQTTYKANKVVKMPPRHKIE
HRLVRSEDGETIQLQEHAVAKYFTE
```

SEQ ID NO: 9 is the amino acid sequence of an additional modified ccGFP polypeptide:

```
MSMSKQVLKENMKTTYHMDGSVNGHYFTIEGEGTGNPFKGQQSLKLRVT
KGGPLPFAFDILSPTFTYGNRVFTDYPEYMPDYFKRSLPEGYSWERTMM
YEDGATATASVRISLDKNGFVHKSTFHGENFPANGPVMKKKGVNWEPSS
ETITPSDGILKGDVTMFLVLEGGQRLKALFQTTYKANKVVKMPPRHKIE
HRLVRSEDGETIQLQEHAVAKYFTE
```

SEQ ID NO: 10 is the amino acid sequence of a split ccGFP 1-10 E6 polypeptide:

MSMSKQVLKEDMKMTYHMDGSVNGHYFTIEGEGTGNPFKGQQTLKLRVT

KGGPLPFAFDILSPTFTYGNRVFTDYPEDMPDYFKQSLPEGYSWERTMM

YDDGASATASARISLDKNGFVHKSTFHGENFPANGPVMKKKGVNWEPSS

ETITASDGILKGDVTMFLVLEGGQRLKALFQTTYKANKVVKMPPRHKIE

HRLVRS

SEQ ID NO: 11 is the amino acid sequence of a split ccGFP S11 E6 polypeptide: GDTVQLQEHAVAKYFTV SEQ ID NO: 12 is the amino acid sequence of ccGFP wild type:
MSLSKQVVKEDMKMTYHMDGCVNGHYFTIEGEGTGKPFKGQKTLKLRVT

EGGPLPFAFDILSATFTYGNRCFCDYPEDMPDYFKQSLPEGYSWERTMM

YEDGACGTASAHISLDKNGFVHNSTFHGVNFPANGPVMKKKGVNWEPSS

EKITACDGILKGDVTMFLVLEGGHRLKCLFQTTYKADKVVKMPPNHIIE

HRLVRSEDGDAVQIQEHAVAKYFTV

SEQ ID NO: 13 is the amino acid sequence of ccGFP m:

MSLSKQVVKEDMKMTYHMDGCVNGHYFTIEGEGTGKPFKGQKTLKLRVT

EGGPLPFAFDILSATFTYGNRCFCDYPEDMPDYFKQSLPEGYSWERTMM

YEDGACGTASAHISLDKNGFVHNSTFHGENFPANGPVMKKKGVNWEPSS

EKITACDGILKGDVTMFLVLEGGHRLKCLFQTTYKADKVVKMPPRHEIE

HRLVRSEDGDAVQIQEHAVAKYFTV

SEQ ID NO: 14 is the amino acid sequence of ccGFP syn:

MSLSKQVVKEDMKMTYHMDGCVNGHYFTIEGEGTGKPFKGQKTLKLRVT

EGGPLPFAFDILSATFTYGNRCFCDYPEDMPDYFKQSLPEGYSWERTMM

YEDGACGTASAHISLDKNGFVQKSTFHGENFPANGPVMKKKGVNWEPSS

EKITACDGILKGDVTMFLVLEGGHRLKCLFQTTYKADKVVKMPPRHEIE

HRLVRSEDGDAVQIQEHAVAKYFTV

SEQ ID NO: 15 is an exemplary nucleic acid sequence encoding ccGFP 1-10 version 1:

ATGTCTATGTCAAAACAAGTGCTCAAAGAAAACATGAAAACGACTTATC

ACATGGACGGTTCGGTGAACGGGCATTATTTCACGATAGAAGGTGAAGG

GACTGGGAACCCATTTAAAGGCCAACAGTCCTTGAAATTACGCGTTACG

AAGGGGGGCCCGCTTCCGTTTGCATTTGATATCCTGAGTCCCACTTTTA

CCTACGGGAATCGTGTTTTCACTGATTATCCCGAGGATATGCCAGATTA

CTTCAAGCAGAGTCTACCAGAGGGATACTCATGGGAACGAACCATGATG

TATGAAGACGGAGCCACGGCCACGGCCTCAGCGCGTATATCTTTAGACA

AAAACGGCTTCGTACATAAAAGCACCTTTCATGGTGAGAACTTCCCTGC

AAATGGACCAGTAATGAAGAAGAAGGGGGTAAACTGGGAACCGTCTTCA

GAGACGATAACTCCTTCGGATGGCATTCTCAAAGGGGATGTCACCATGT

TCCTTGTATTAGAAGGAGGGCAACGCTTGAAGGCTTTGTTTCAGACCAC

ATATAAGGCTAACAAAGTTGTCAAAATGCCGCCACGCCACAAGATCGAA

CACAGGCTAGTGCGCTCT

SEQ ID NO: 16 is an exemplary nucleic acid sequence encoding ccGFP 1-10 version 2:

ATGTCTATGTCAAAACAAGTGCTCAAAGAAAACATGAAAACGACTTATC

ACATGGACGGTTCGGTGAACGGGCATTATTTCACGATAGAAGGTGAAGG

GACTGGGAACCCATTTAAAGGCCAACAGTCCTTGAAATTACGCGTTACG

AAGGGGGGCCCGCTTCCGTTTGCATTTGATATCCTGAGTCCCACTTTTA

CCTACGGGAATCGTGTTTTCACTGATTATCCCGAGTATATGCCAGATTA

CTTCAAGCGGAGTCTACCAGAGGGATACTCATGGGAACGAACCATGATG

TATGAAGACGGAGCCACGGCCACGGCCTCAGTGCGTATATCTTTAGACA

AAAACGGCTTCGTACATAAAAGCACCTTTCATGGTGAGAACTTCCCTGC

AAATGGACCAGTAATGAAGAAGAAGGGGGTAAACTGGGAACCGTCTTCA

GAGACGATAACTCCTTCGGATGGCATTCTCAAAGGGGATGTCACCATGT

TCCTTGTATTAGAAGGAGGGCAACGCTTGAAGGCTTTGTTTCAGACCAC

ATATAAGGCTAACAAAGTTGTCAAAATGCCGCCACGCCACAAGATCGAA

CACAGGCTAGTGCGCTCA

SEQ ID NO: 17 is an exemplary nucleic acid sequence encoding ccGFP 1-10 version 3:

ATGTCTATGGAAAAACAAGTGCTCAAAGAAAACATGAAAACGACTTATC

ACATGGACGGTTCGGTGGATGGGCATTATTTCGAAATAGAAGGTGAAGG

GACTGGGAACCCATTTAAAGGCGAACAGGAATTGAAATTACGCGTTACG

AAGGGGGGCCCGCTTCCGTTCGCATTTGATATCCTGAGTCCCACTTTTA

CCTACGGGAATCGTGTTTTCACTGATTATCCCGAGGATATGCCCGATTA

CTTCAAGCAGAGTCTACCAGAGGGATACTCATGGGAACGAACCATGATG

TATGAAGACGGAGCCACGGCCACGGCCTCAGCGCGTATATCTTTAGACA

AAAACGGCTTCGTACATAAAAGCACCTTTCATGGAGAGAACTTCCCCGC

AAATGGACCAGTAATGAAGAAAAGGGGGTAGATTGGGAACCGTCTTCA

GAGACGATAACTCCTGAAGATGGCATTCTCAAAGGGGATGTCGAAATGT

TCCTTGTATTAGAAGGAGGGCAACGCTTGAAGGCTTTGTTTCAGACCAC

ATATAAGGCTAACAAAGTTGTCAAAATGCCGCCACGCCACAAGATCGAA

CACAGGCTAGTGCGCTCT

SEQ ID NO: 18 is an exemplary nucleic acid sequence encoding ccGFP S11:

GGGGAGACTATACAGCTCCAGGAGCACGCAGTCGCTAAATATTTCACGG
AA

DETAILED DESCRIPTION

I. Terms

Unless otherwise noted, technical terms are used according to conventional usage. Definitions of common terms in molecular biology can be found in Benjamin Lewin, Genes VII, published by Oxford University *Press,* 1999; Kendrew et al. (eds.), *The Encyclopedia of Molecular Biology*, published by Blackwell Science Ltd., 1994; and Robert A. Meyers (ed.), *Molecular Biology and Biotechnology: a Comprehensive Desk Reference*, published by VCH Publishers, Inc., 1995; and other similar references.

As used herein, the singular forms "a," "an," and "the," refer to both the singular as well as plural, unless the context clearly indicates otherwise. For example, the term "a polypeptide" includes single or plural polypeptides and can be considered equivalent to the phrase "at least one polypeptide." As used herein, the term "comprises" means "includes." Thus, "comprising a polypeptide" means "including a polypeptide" without excluding other elements. It is further to be understood that any and all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting. To facilitate review of the various embodiments, the following explanations of terms are provided:

Binding: A specific interaction between two molecules. For example, binding can occur between a fragments of a split fluorescent protein (e.g., a GFP 1-10 detector and a GFP S11 tag). Binding can be specific and selective, so that one molecule is bound preferentially when compared to another molecule. In one example, specific binding is identified by a disassociation constant ($K_d$) of an agent for a particular protein or class of proteins, compared to the $K_d$ for one or more other proteins.

Conservative variants: "Conservative" amino acid substitutions are those substitutions that do not substantially affect or decrease a function of a protein, such as the fluorescent or other properties of a fluorescent protein. The term conservative variation also includes the use of a substituted amino acid in place of an unsubstituted parent amino acid. Furthermore, one of ordinary skill will recognize that individual substitutions, deletions or additions which alter, add or delete a single amino acid or a small percentage of amino acids (for instance less than 5%, in some embodiments less than 1%) in an encoded sequence are conservative variations where the alterations result in the substitution of an amino acid with a chemically similar amino acid.

Conservative amino acid substitution tables providing functionally similar amino acids are well known to one of ordinary skill in the art. The following six groups are examples of amino acids that are considered to be conservative substitutions for one another:

1) Alanine (A), Serine(S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Non-conservative substitutions are those that alter a function of the protein, such as the fluorescent or other properties of a fluorescent protein. For instance, if an amino acid residue is important (or even essential) for a function of the protein, even an otherwise conservative substitution may disrupt that activity. Thus, a conservative substitution does not alter the basic function of a protein of interest.

Expression: The process by which the coded information of a gene is converted into an operational, non-operational, or structural part of a cell, such as the synthesis of a protein.

Fluorescent protein: A protein or protein complex that has the ability to emit light of a particular wavelength (emission wavelength) when exposed to light of another wavelength (excitation wavelength). Fluorescent proteins typically form a three-dimensional structure including eleven anti-parallel outer beta strands and one inner alpha strand. Several natural and recombinant green fluorescent protein (GFP) variants are known, including variants that exhibit altered fluorescent properties. Corynactis *californica*, a bright red colonial anthozoan similar to sea anemones and scleractinian stony corals, expresses several fluorescent proteins in its morphs, including GFPs.

Split-Fluorescent Protein (SFP): A protein complex composed of two or more protein fragments that individually are not fluorescent, but, when formed into a complex, result in a functional (that is, fluorescing) fluorescent protein complex. Individual protein fragments of an SFP are known as complementing fragments or complementary fragments. Complementing fragments which will spontaneously assemble into a functional fluorescent protein complex are known as self-complementing, self-assembling, or spontaneously-associating complementing fragments. A complemented split fluorescent protein complex is a protein complex comprising all the complementing fragments of an SFP necessary for the SFP to be active (e.g., fluorescent).

Complementary SFP fragments can be derived from the three dimensional structure of GFP, which includes eleven anti-parallel outer beta strands and one inner alpha strand (see e.g., the GFP structure deposited as PDB No. 1EMA, and Ormo et al., Science, 273:1392-5, 1996, and Yang et al., Nat. Biotechnol., 14:1246-51, 1996.) A SFP tag corresponds to one or two of the eleven beta-strands of the GFP molecule, and a SFP detector corresponds to the remaining nine or ten β-strands and the α-strand of the GFP. An SFP10 tag includes β-strand 10 of an eleven stranded fluorescent protein β-barrel, and a SFP11 tag includes β-strand 11 of an eleven stranded fluorescent protein β-barrel. An SFP10 detector includes β-strands 1-10 of an eleven-stranded fluorescent protein β-barrel. Other combinations of fragments are also possible, for example, as disclosed in U.S. Pat. App. Pub. Nos. 2005/0221343 and 2015/0099271.

Fused: Linkage by covalent bonding. In some embodiments, "fused" refers to making two polypeptides into one contiguous polypeptide molecule by recombinant means. For example, a fusion protein is a protein including two separate polypeptides that are linked together.

Heterologous: Originating from a different genetic source or species or altered compared to its original source or species. For example, a nucleic acid that is heterologous to a cell originates from an organism or species other than the cell in which it is expressed. In one specific, non-limiting example, a heterologous nucleic acid includes a SFP nucleic acid that is present or expressed in a bacterial cell (such as an *E. coli* cell) or in an fungal, plant, or mammalian cell. Methods for introducing a heterologous nucleic acid into bacterial, fungal, plant, and mammalian cells are known in the art, for example transformation with a nucleic acid, including electroporation, lipofection, and particle gun acceleration.

In another example of use of the term heterologous, a nucleic acid operably linked to a heterologous promoter is from an organism or species other than that of the promoter. In other examples of the use of the term heterologous, a nucleic acid encoding a polypeptide (such as a SFP polypeptide disclosed herein) or portion thereof is operably linked to a heterologous nucleic acid encoding a second polypeptide or portion thereof, for example to form a non-naturally occurring fusion protein.

Host Cell or Recombinant Host Cell: A cell that has been genetically altered, or is capable of being genetically altered, by introduction of an exogenous polynucleotide, such as a recombinant plasmid or vector. Typically, a host cell is a cell in which a vector can be propagated and its DNA expressed. The cell may be prokaryotic or eukaryotic. For example, the host cell may be a bacterial cell, including an *E. coli* cell. "Host cell" also includes a colony of cells, for example, a colony of *E. coli* cells. Thus, "contacting a host cell" and "incubating a host cell" include contacting a colony of host cells or incubating a colony of host cells. The term also includes any progeny of the subject host cell. It is understood that all progeny may not be identical to the parental cell since there may be mutations that occur during replication. However, such progeny are included when the term "host cell" is used. A host cell encompasses material inside the outermost cell membrane, the outermost cell membrane itself and material fused or attached to the outermost cell membrane. In the case of a cell having a cell wall, the outermost cell membrane is the cell wall. Thus, the phase "within a host cell" includes material inside the outermost cell membrane, the outermost cell membrane itself and material fused or attached to the outermost cell membrane.

Isolated: A biological component (such as a host cell, nucleic acid molecule, or protein) that has been substantially separated or purified away from other biological components in the medium, cell, or organism in which the component occurs. The term isolated does not require absolute purity. Nucleic acids and proteins that have been isolated include nucleic acids and proteins purified by standard purification methods. The term also embraces nucleic acids and proteins prepared by recombinant expression in a host cell, as well as chemically synthesized nucleic acids.

Operably linked: A first nucleic acid sequence is operably linked to a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein-coding regions, in the same reading frame.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, for example, by genetic engineering techniques. A recombinant protein is one that has a sequence that is not naturally occurring or has a sequence that is made by an artificial combination of two otherwise separated segments of sequence.

The term recombinant also includes nucleic acids or proteins that have been altered solely by addition, substitution, or deletion of a portion of the nucleic acid sequence or amino acid sequence, respectively.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes or other genetic elements known in the art. An integrating vector is capable of integrating itself into a host nucleic acid. An expression vector is a vector that contains the necessary regulatory sequences to allow transcription and translation of inserted gene or genes.

II. Modified ccGFP and Fragments Thereof

A. Polypeptides

Provided herein are modified *Corynactis californica* GFP (ccGFP) polypeptides, which in some examples have improved properties, including improved solubility, stability, binding, and/or fluorescence compared to native *C. californica* GFP polypeptides. The disclosed GFP polypeptides include modified full-length (or substantially full-length) ccGFP polypeptides and split ccGFP polypeptides.

In some embodiments, a ccGFP polypeptide provided herein includes an amino acid sequence with at least 90% sequence identity (e.g., at least 90%, 91%, 92%, 93%, 94%, 95%, 96%, 97%, 98%, 99%, or more identity) to SEQ ID NO: 5. In other embodiments, the ccGFP polypeptide includes or consists of the amino acid sequence of SEQ ID NO: 5.

In other embodiments, a ccGFP polypeptide provided herein includes an amino acid sequence with at least 90% sequence identity (e.g., at least 90%, 91%, 92%, 93%, 94%, 95%, 96%, 97%, 98%, 99%, or more identity) to SEQ ID NO: 6, wherein the amino acid sequence includes one or more or all of asparagine at position 11, threonine at position 14, serine at position 43, glutamic acid at position 100, threonine at position 104, proline at position 152, glutamic acid at position 206, isoleucine at position 208, and glutamic acid at position 221 of SEQ ID NO: 6. In other embodiments, the ccGFP polypeptide includes or consists of the amino acid sequence of SEQ ID NO: 6.

In still further embodiments, a ccGFP polypeptide provided herein includes an amino acid sequence with at least 90% sequence identity (e.g., at least 90%, 91%, 92%, 93%, 94%, 95%, 96%, 97%, 98%, 99%, or more identity) to SEQ ID NO: 7, wherein the amino acid sequence includes one or more or all of glutamic acid at position 4, asparagine at position 11, threonine at position 14, aspartic acid at position 23, glutamic acid at position 28, glutamic acid at position 41, glutamic acid at position 43, glutamic acid at position 100, threonine at position 104, aspartic acid at position 142, proline at position 152, glutamic acid at position 162, glutamic acid at position 206, isoleucine at position 208, and glutamic acid at position 221 of SEQ ID NO: 7. In other embodiments, the ccGFP polypeptide includes or consists of the amino acid sequence of SEQ ID NO: 7.

In yet further embodiments, a ccGFP polypeptide provided herein includes an amino acid sequence with at least 90% sequence identity (e.g., at least 90%, 91%, 92%, 93%, 94%, 95%, 96%, 97%, 98%, 99%, or more identity) to SEQ ID NO: 8, wherein the amino acid sequence includes one or more or all of glutamic acid at position 206, isoleucine at position 208, and glutamic acid at position 221 of SEQ ID NO: 8. In other embodiments, the ccGFP polypeptide includes or consists of the amino acid sequence of SEQ ID NO: 8.

In additional embodiments, a ccGFP polypeptide provided herein includes an amino acid sequence with at least 90% sequence identity (e.g., at least 90%, 91%, 92%, 93%, 94%, 95%, 96%, 97%, 98%, 99%, or more identity) to SEQ ID NO: 9, wherein the amino acid sequence includes one or more or all of asparagine at position 11, threonine at position 14, serine at position 43, tyrosine at position 78, arginine at position 85, glutamic acid at position 100, threonine at position 104, valine at position 109, proline at position 152, glutamic acid at position 206, isoleucine at position 208, and glutamic acid at position 221 of SEQ ID NO: 9. In other embodiments, the ccGFP polypeptide includes or consists of the amino acid sequence of SEQ ID NO: 9.

Also provided herein are split GFP detector and tag polypeptides. The split detector and tag polypeptides are capable of complementation with a detector or tag polypeptide from a fluorescent protein to form a functional (e.g., fluorescing) SFP. In some examples, the detector and tag are from the same GFP polypeptide, or a modified version thereof (e.g., both are from ccGFP). In other examples, the detector and tag are from different GFP polypeptides.

In some embodiments the SFP detector includes at least ten contiguous β-strands (e.g., β-strands 1-10) of a ccGFP including the amino acid sequence of SEQ ID NO: 5. Thus, in some examples, the SFP detector includes amino acids 1-202 of SEQ ID NO: 5. In other examples, the SFP detector includes or consists of the amino acid sequence of SEQ ID NO: 10.

In other embodiments, the split GFP detector includes an amino acid sequence with at least 90% sequence identity (e.g., at least 90%, 91%, 92%, 93%, 94%, 95%, 96%, 97%, 98%, 99%, or more identity) to SEQ ID NO: 1, wherein the amino acid sequence includes one or more or all of asparagine at position 11, threonine at position 14, serine at position 43, glutamic acid at position 100, threonine at position 104, and proline at position 152 of SEQ ID NO: 1.

In further embodiments, the split GFP detector includes an amino acid sequence with at least 90% sequence identity (e.g., at least 90%, 91%, 92%, 93%, 94%, 95%, 96%, 97%, 98%, 99%, or more identity) to SEQ ID NO: 2, wherein the amino acid sequence includes one or more or all of asparagine at position 11, threonine at position 14, serine at position 43, tyrosine at position 78, arginine at position 85, glutamic acid at position 100, threonine at position 104, valine at position 109, and proline at position 152 of SEQ ID NO: 2.

In additional embodiments, the split GFP detector includes an amino acid sequence with at least 90% sequence identity (e.g., at least 90%, 91%, 92%, 93%, 94%, 95%, 96%, 97%, 98%, 99%, or more identity) to SEQ ID NO: 3, wherein the amino acid sequence includes one or more or all of glutamic acid at position 4, asparagine at position 11, threonine at position 14, glutamic acid at position 23, glutamic acid at position 28, glutamic acid at position 41, glutamic acid at position 43, glutamic acid at position 100, threonine at position 104, glutamic acid at position 142, proline at position 152, glutamic acid at position 153, and glutamic acid at position 162 of SEQ ID NO: 3.

In other embodiments, the polypeptide includes or consists of the amino acid sequence of SEQ ID NO: 10. In other embodiments, the SFP detector includes or consists of the amino acid sequence of any one of SEQ ID NOs: 1-3.

In some embodiments, a split ccGFP tag provided herein includes β-strand 11 (e.g., β-strand S11) of a ccGFP including the amino acid sequence of SEQ ID NO: 5. Thus, in some examples, the SFP tag includes amino acids 205-221 of SEQ ID NO: 5. In other examples, the SFP tag includes or consists of the amino acid sequence of SEQ ID NO: 11.

In particular embodiments, the split ccGFP tag includes an amino acid sequence with at least 90% sequence identity (e.g., at least 90%, 91%, 92%, 93%, 94%, 95%, 96%, 97%, 98%, 99%, or more identity) to SEQ ID NO: 4, wherein the amino acid sequence includes one or more or all of glutamic acid at position 2, isoleucine at position 4, and glutamic acid at position 17 of SEQ ID NO: 4. In other embodiments, the split ccGFP tag includes or consists of the amino acid sequence of SEQ ID NO: 4.

Based on the known three-dimensional structure of GFP, one of ordinary skill in the art can design variants of the disclosed ccGFP polypeptides, including the ccGFP detectors and/or tags that would not affect the function of the detectors or tags. For example, amino acid substitutions (such as conservative amino acid substitutions) to the connecting loops between the beta strands of the eleven stranded beta-barrel structure of GFP are possible. Thus, in some examples, the disclosed ccGFP polypeptides, ccGFP detectors, or ccGFP tags can include one or more conservative amino acid substitution (such as a single conservative amino acid substitution, for example, one or more conservative amino acid substitutions, for example 1-10 conservative substitutions, 2-5 conservative substitutions, 4-9 conservative substitutions, such as 1, 2, 5 or 10 conservative substitutions). In other examples, the protein may include one or more non-conservative substitutions (for example 1-10 non-conservative substitutions, 2-5 non-conservative substitutions, 4-9 non-conservative substitutions, such as 1, 2, 5 or 10 non-conservative substitutions), so long as the protein retains one or more of its functions, including fluorescence and/or ability to form a fluorescent complex (e.g., by association of an SFP detector and an SFP tag).

In additional embodiments, a polypeptide comprising an SFP detector can vary in length according to the specific application. For example, in some embodiments, a polypeptide including an SFP detector includes a minimum length, such as at least 75 (such as at least 100, at least 125, at least 150, at least 200, at least 250, at least 300, at least 350, at least 400, at least 450, at least 500, at least 550, at least 600, at least 650, at least 700, at least 750, at least 800, at least 850, at least 900, at least 950, or at least 1000) amino acids in length, wherein the polypeptide comprises an SFP detector as described herein and wherein the SFP detector retains the ability to complement with an SFP tag to form a functional fluorescent protein. In further embodiments, a polypeptide comprising an SFP detector includes a maximum length, such as no more than 250 (such as no more than 300, no more than 350, no more than 400, no more than 450, no more than 500, no more than 550, no more than 600, no more than 650, no more than 700, no more than 750, no more than 800, no more than 850, no more than 900 no more than 950, or no more than 1000) amino acids in length, wherein the polypeptide comprises an SFP detector as described herein and wherein the SFP detector retains the ability to complement with an SFP tag to form a functional fluorescent protein. A polypeptide comprising an SFP tag can vary in length according to the specific application. For example, in some embodiments, a polypeptide including an SFP tag includes a minimum length, such as at least 15 (such as at least 20, at least 30, at least 50, at least 75, at least 100, at least 200, at least 300, at least 400, at least 450, at least 500, at least 550, at least 600, at least 650, at least 700, at least 750, at least 800, at least 850, at least 900, at least 950, or at least 1000) amino acids in length, wherein the polypeptide comprises an SFP tag as described herein and wherein the SFP tag retains the ability to complement with an SFP detector to form a functional fluorescent protein. In further embodiments, a polypeptide comprising an SFP tag includes a maximum length, such as no more than 20 (such as no more than 30, no more than 50, no more than 75, no more than 100, no more than 200, no more than 300, no more than 400, no more than 450, no more than 500, no more than 550, no more than 600, no more than 650, no more than 700, no more than 750, no more than 800, no more than 850, no more than 900 no more than 950, or no more than 1000) amino acids in length, wherein the polypeptide comprises an SFP tag as described herein and wherein the SFP tag retains the ability to complement with an SFP detector to form a functional fluorescent protein.

In some embodiments, a polypeptide including a disclosed SFP detector is fused to a protein of interest or a portion thereof. In some examples, the protein of interest is fused to the N-terminus or the C-terminus of the SFP detector. In other examples, the protein of interest is fused to an internal portion of the SFP detector polypeptide. In some embodiments, the SFP detector is joined to the protein of interest by a peptide linker. Suitable peptide linkers are known to one of ordinary skill in the art and include glycine-serine linkers. In some non-limiting examples, the protein of interest includes a subcellular localization element, for example as described in U.S. App. Pub. Nos. 2005/0221343 and 2012/0282643; PCT Pub. No. WO/2005/074436; and U.S. Pat. Nos. 7,666,606 and 7,585,636, each of which is incorporated herein in its entirety. Typically, when fused to a polypeptide (e.g., a protein of interest), an SFP detector is substantially non-perturbing to the structure of the protein of interest.

In additional embodiments, a polypeptide including a disclosed SFP tag can be fused to a protein of interest, or a portion thereof. In some examples, the protein of interest is fused to the N-terminus or the C-terminus of the SFP tag. In some embodiments, the SFP tag is joined to the protein of interest by a peptide linker. Suitable peptide linkers are known to one of ordinary skill in the art and include glycine-serine linkers. Typically, when fused to a polypeptide (e.g., a protein of interest), an SFP tag is substantially non-perturbing to the structure of the protein of interest.

B. Nucleic acids, Vectors, and Host Cells

Also provided are exemplary nucleic acid molecules encoding the ccGFP and split ccGFP polypeptides disclosed herein. The disclosed nucleic acids include DNA, cDNA and RNA sequences which encode the polypeptides, for example, including the nucleic acid sequences disclosed herein. The coding sequences include variants that result from the degeneracy (e.g., redundancy) of the genetic code, whereby more than one codon can encode the same amino acid residue. Tables showing the standard genetic code can be found in various sources.

In addition, the disclosed nucleic acids may be codon-optimized for expression in a given organism. Codon usage bias, the use of synonymous codons at unequal frequencies, is ubiquitous among genetic systems. The strength and direction of codon usage bias is related to genomic G+C content and the relative abundance of different isoaccepting tRNAs. Codon usage can affect the efficiency of gene expression. Codon-optimization refers to replacement of at least one codon (such as at least 5 codons, at least 10 codons, at least 25 codons, at least 50 codons, at least 75 codons, at least 100 codons or more) in a nucleic acid sequence with a synonymous codon (one that codes for the same amino acid) more frequently used (preferred) in the organism. Each organism has a particular codon usage bias for each amino acid, which can be determined from publicly available codon usage tables. For example, a codon usage database is available on the World Wide Web at kazusa.or.jp/codon. One of skill in the art can modify a nucleic acid encoding a particular amino acid sequence, such that it encodes the same amino acid sequence, while being optimized for expression in a particular cell type.

In some embodiments, the split GFP detector includes a nucleic acid molecule with at least 90% sequence identity (e.g., at least 90%, 91%, 92%, 93%, 94%, 95%, 96%, 97%, 98%, 99%, or more identity) to SEQ ID NO: 15, wherein the nucleic acid molecule encodes one or more or all of asparagine at amino acid position 11, threonine at amino acid position 14, serine at amino acid position 43, glutamic acid at amino acid position 100, threonine at amino acid position 104, and proline at amino acid position 152 (amino acid positions corresponding to the amino acid sequence of SEQ ID NO: 1). In other embodiments, the split GFP detector is encoded by a nucleic acid molecule that includes or consists of the nucleic acid sequence of SEQ ID NO: 15.

In further embodiments, the split GFP detector includes a nucleic acid molecule with at least 90% sequence identity (e.g., at least 90%, 91%, 92%, 93%, 94%, 95%, 96%, 97%, 98%, 99%, or more identity) to SEQ ID NO: 16, wherein the nucleic acid molecule encodes one or more or all of asparagine at amino acid position 11, threonine at amino acid position 14, serine at amino acid position 43, tyrosine at amino acid position 78, arginine at amino acid position 85, glutamic acid at amino acid position 100, amino acid threonine at position 104, valine at amino acid position 109, and proline at amino acid position 152 (amino acid positions corresponding to the amino acid sequence of SEQ ID NO: 2). In other embodiments, the split GFP detector is encoded by a nucleic acid molecule that includes or consists of the nucleic acid sequence of SEQ ID NO: 16.

In additional embodiments, the split GFP detector includes a nucleic acid molecule with at least 90% sequence identity (e.g., at least 90%, 91%, 92%, 93%, 94%, 95%, 96%, 97%, 98%, 99%, or more identity) to SEQ ID NO: 17, wherein the nucleic acid molecule encodes one or more or all of glutamic acid at amino acid position 4, asparagine at amino acid position 11, threonine at amino acid position 14, glutamic acid at amino acid position 23, glutamic acid at amino acid position 28, glutamic acid at amino acid position 41, glutamic acid at amino acid position 43, glutamic acid at amino acid position 100, threonine at amino acid position 104, glutamic acid at amino acid position 142, proline at amino acid position 152, glutamic acid at amino acid position 153, and glutamic acid at amino acid position 162 (amino acid positions corresponding to the amino acid sequence of SEQ ID NO: 3). In other embodiments, the split GFP detector is encoded by a nucleic acid molecule that includes or consists of the nucleic acid sequence of SEQ ID NO: 17.

In other embodiments, the split ccGFP tag includes a nucleic acid molecule with at least 90% sequence identity (e.g., at least 90%, 91%, 92%, 93%, 94%, 95%, 96%, 97%, 98%, 99%, or more identity) to SEQ ID NO: 18, wherein the nucleic acid molecule encodes one or more or all of glutamic acid at amino acid position 2, isoleucine at amino acid position 4, and glutamic acid at amino acid position 17 (amino acid positions corresponding to the amino acid sequence of SEQ ID NO: 4). In other embodiments, the split ccGFP tag is encoded by a nucleic acid molecule that includes or consists of the nucleic acid sequence of SEQ ID NO: 18.

Nucleic acid molecules encoding one or more ccGFP proteins, ccGFP detectors, and ccGFP tags provided herein, and fusions of a disclosed ccGFP protein, detector, or tag with a protein of interest can be included in one or more expression vectors to direct expression of the nucleic acid. The vectors may further include expression control sequences including one or more of appropriate promoters, enhancers, transcription terminators, a start codon 5' of a protein-encoding sequence, splicing signal for introns, maintenance of the correct reading frame of that gene to permit proper translation of mRNA, and stop codons can be included in an expression vector. Generally, expression control sequences include at least a promoter, a minimal sequence sufficient to direct transcription. The promoter can be inducible or constitutive. In one embodiment, the promoter is a heterologous promoter.

Expression vectors used to express one or more ccGFP proteins, ccGFP detectors, and ccGFP tags provided herein, and fusions of a disclosed ccGFP protein, detector, or tag with a protein of interest are selected to be compatible with the host cell in which the proteins are to be expressed. Similarly, various promoter systems are selected for compatibility with the host cell. Codon optimization techniques may be employed to adapt sequences for use in particular cell types.

Unlike constitutive promoters, an inducible promoter is not always active. Some inducible promoters are activated by physical stimuli, such as the heat shock promoter. Others are activated by chemical stimuli, such as IPTG or Tetracycline (Tet), or galactose. Inducible promoters or geneswitches are used to both spatially and temporally regulate gene expression. Thus, for a typical inducible promoter in the absence of the inducer, there would be little or no gene expression while, in the presence of the inducer, expression should be high (e.g., off/on).

In some embodiments, multiple inducible promoters are included in an expression vector, each promoter induced by the same or a different inducer. In other embodiments, multiple expression vectors are included in the host cell, each expression vector comprising an inducible promoter, each inducible promoter induced by the same or a different inducer. In this way, expression of multiple proteins in a host cell can be independently under the control of separate inducible promoters. Thus, in some embodiments, host cells are engineered to express one or more complementary fragments of an SFP (such as a ccGFP detector and a ccGFP tag), one or more of which are fused to one or more proteins of interest. The fragments may be expressed simultaneously or sequentially.

In one example, a vector in which the promoter is under the repression of the Laclq protein and the arabinose inducer/repressor is used for expression of the SFP detector (e.g., pPROLAR vector available from Clontech, Palo Alto, Calif.). Repression is relieved by supplying IPTG and arabinose to the growth media, resulting in the expression of the SFP detector. In this system, the araC repressor is supplied by the genetic background of the host E. coli cell. For the controlled expression of a test protein-SFP tag fusion, a vector in which the test protein-SFP tag fusion is under the repression of the tetracycline repressor protein may be used (e.g., pPROTET vector; Clontech). In this system, repression is relieved by supplying anhydrotetracycline to the growth media, resulting in the expression of the test protein-SFP tag fusion construct. The tetR and Laclq repressor proteins may be supplied on a third vector or may be incorporated into the fragment-carrying vectors.

The disclosed embodiments may be applied in virtually any host cell type. including without limitation bacterial cells (e.g., E. coli) and mammalian cells. Host cells can include isolated microbial, yeast, insect and mammalian cells, as well as cells located in an organism. For example, the host cell may be an E. coli cell, such as an E. coli BL21 (DE3) strain cell. Secretion competent yeast and bacterial cells may be used. Nucleic acid encoding one or more ccGFP proteins, ccGFP detectors, and/or ccGFP tags provided herein, and/or fusions of a disclosed ccGFP protein, detector, or tag with a protein of interest are included in an expression vector introduced into the host cells.

A transformed cell is a cell into which (or into an ancestor of which) has been introduced, by means of recombinant DNA techniques, a DNA molecule encoding one or more ccGFP proteins, ccGFP detectors, and/or ccGFP tags provided herein, and fusions of a disclosed ccGFP protein, detector, or tag with a protein of interest. Transformation of a host cell with recombinant DNA may be carried out by techniques as known to one of ordinary skill in the art. Where the host is prokaryotic, such as E. coli, competent cells which are capable of DNA uptake can be prepared from cells harvested after exponential growth phase and subsequently treated by the $CaCl_2$) method using procedures well known in the art. Alternatively, $MgCl_2$ or RbCl can be used. Transformation can also be performed after forming a protoplast of the host cell if desired, or by electroporation.

When the host is a eukaryote, such as a mammalian cell, such methods of transfection of DNA as calcium phosphate coprecipitation, mechanical procedures such as microinjection, electroporation, insertion of a plasmid encased in a liposome, or virus vectors may be used. Eukaryotic cells can also be cotransformed with DNA sequences encoding one or more ccGFP proteins, ccGFP detectors, and/or ccGFP tags provided herein, or fusions of a disclosed ccGFP protein, detector, or tag with a protein of interest and a second nucleic acid molecule encoding a selectable phenotype, such as neomycin resistance. Another method is to use a eukaryotic viral vector, such as simian virus 40 (SV40) or bovine papilloma virus, to transiently infect or transform eukaryotic cells and express the protein. Other specific, non-limiting examples of viral vectors include adenoviral vectors, lentiviral vectors, retroviral vectors, and pseudorabies vectors.

III. Methods of Use

Methods of using the disclosed SFPs and fluorescent proteins are also provided. For example, the disclosed SFP detectors and tags are useful in methods of detecting a protein of interest (including detecting and/or quantifying a soluble or insoluble protein) or detecting protein-protein interactions between a first second protein. For example, the disclosed ccGFP 1-10 detectors exhibit minimal self-assembly with the ccGFP S11 tag, unless the tag and detector are brought into relatively close proximity with one another. In some examples, the tag and detector are brought into proximity by linkage to the N- and C-terminus of the same protein, or by linkage to interacting protein pairs. The methods may be carried out in living cells, in cell lysates, or other in vitro assay formats.

Suitable conditions for complementing split GFP detectors and GFP tags are known to a person of ordinary skill in the art (see, e.g., U.S. App. Pub. Nos. 2005/0221343 and 2012/0282643; PCT Pub. No. WO/2005/074436, and U.S. Pat. Nos. 7,666,606; and 7,585,636). Exemplary methods are also provided in the Examples below.

In some examples, the methods include complementation of a disclosed ccGFP detector and a disclosed ccGFP tag. In other examples, the methods include complementation of a disclosed ccGFP detector with a SFP tag known in the art. In further examples, the methods include complementation of a SFP detector known in the art with a disclosed ccGFP tag. SFP detectors and tags that can be used with the disclosed ccGFP detectors and tags include those described in, e.g., U.S. App. Pub. Nos. 2005/0221343, 2012/0282643, and 2015/0099271; and U.S. Pat. Nos. 7,666,606; and 7,585,636, each of which is incorporated by reference herein in its entirety.

In some embodiments, a method of detecting a protein of interest is provided. The method may be carried out in vitro or in vivo. In some examples, the method includes providing an SFP detector, for example a ccGFP detector disclosed herein and an SFP tag (e.g., a ccGFP tag disclosed herein) linked to the protein of interest, wherein the SFP detector and SFP tag complement to form a fluorescent protein complex and detecting fluorescence of the fluorescent protein complex, thereby detecting the protein of interest. In some examples, the SFP detector includes the amino acid sequence of any one of SEQ ID NOs: 1-3 and/or the SFP tag includes the amino acid sequence of SEQ ID NO: 4.

In some embodiments of the method, the SFP detector and the SFP tag linked to the protein of interest are expressed in a host cell from one of more expression vectors encoding the SFP detector and the SFP tag linked to the protein of interest. In some examples, the SFP detector and the SFP tag linked to the protein of interest are each expressed from an independently inducible promoter. In some examples, the inducible promoter is an IPTG-inducible promoter or a tetracycline regulatable promoter; however, one of ordinary skill in the art can select additional appropriate inducible promoters. In some examples, the host cell is maintained under conditions where both of the independently inducible promoters are repressed, then inducing expression of the SFP tag-protein of interest fusion for a time sufficient to permit expression of the fusion protein and to permit the expressed fusion protein to aggregate if insoluble, then inducing the expression of the SFP detector for a time sufficient to permit expression of the SFP detector and its self-complementation with the SFP tag-protein of interest fusion protein. Detection of fluorescence indicates presence of the soluble protein of interest.

In other embodiments, a method of detecting a protein-protein interaction between a first protein of interest and a second protein of interest in a sample is provided. The method may be carried out in vitro or in vivo. The method includes providing a SFP detector (e.g., a ccGFP detector as disclosed herein) fused to a first protein of interest, wherein the SFP detector can complement with a SFP tag (which may be a ccGFP tag disclosed herein) to form a fluorescent protein complex. A second protein of interest fused to the SFP tag is also provided. If the first protein of interest binds to the second protein of interest, then the SFP tag is brought within close proximity of the SFP detector and detector and the tag will complement to form a fluorescent protein complex. The methods also include measuring fluorescence of the sample, and detection of fluorescence detects the protein-protein interaction. In some examples, the SFP detector includes the amino acid sequence of any one of SEQ ID NOs: 1-3 and/or the SFP tag includes the amino acid sequence of SEQ ID NO: 4. In some examples, the method includes expressing the SFP detector linked to the first polypeptide and the SFP tag linked to the second polypeptide from one or more expression vectors in a host cell.

In an additional embodiment, the first and second protein of interest do not interact directly with each other, but instead form a tertiary complex with a third, untagged protein. In this embodiment, complementation of the SFP fragments is facilitated by the binding of the first protein of interest and the second protein of interest to the third protein, which brings the SFP tag within close proximity of the SFP detector. In this embodiment, detecting the fluorescence of the complemented split-GFP protein complex detects the protein interaction between the first, second, and third proteins.

Also provided in some embodiments are methods of quantifying a protein of interest. In some examples, the methods are carried out in vitro, and include providing a polynucleotide construct comprising the coding sequence of a SFP tag (e.g. a ccGFP tag provided herein) fused to the coding sequence of the protein of interest and culturing a cell containing the polynucleotide construct under conditions permitting the expression of the SFP tag-protein of interest fusion protein for a time sufficient to permit expression of the fusion protein and permit the expressed fusion protein to aggregate if insoluble. The cell is lysed and total protein in the lysate is solubilized, for example by chemical denaturation. The solubilized protein in the lysate is renatured, for example, in a suitable diluent containing an SFP detector (such as a ccGFP detector disclosed herein), wherein the SFP detector and SFP tag complement to form a fluorescent protein complex, under conditions and for a time sufficient to allow self-complementation. Fluorescence in the sample is quantitatively detected to determine the quantity of the protein of interest. In some examples, the SFP detector includes the amino acid sequence of any one of SEQ ID NOs: 1-3 and/or the SFP tag includes the amino acid sequence of SEQ ID NO: 4.

In other embodiments, the methods are carried out in vivo. In some examples, the methods include providing a first polynucleotide construct comprising the coding sequence of a SFP tag (e.g. a ccGFP tag provided herein), fused to the coding sequence of the protein of interest and providing a second polynucleotide construct comprising the coding sequence of a SFP detector (e.g., a ccGFP detector provided herein) and culturing a cell containing the first and second polynucleotide constructs under conditions permitting the expression of the SFP tag-protein of interest fusion and the SFP detector for a time sufficient to permit self-complementation of the SFP tag and SFP detector. Fluorescence in the sample is quantitatively detected to determine the quantity of the protein of interest. In some examples, the SFP detector includes the amino acid sequence of any one of SEQ ID NOs: 1-3 and/or the SFP tag includes the amino acid sequence of SEQ ID NO: 4.

Further provided are methods of detecting a soluble protein of interest in vitro. The methods include providing a polynucleotide construct comprising the coding sequence of a SFP tag (e.g. a ccGFP tag provided herein) fused to the coding sequence of the protein of interest and culturing a cell containing the polynucleotide construct under conditions permitting the expression of the SFP tag-protein of interest fusion and for a time sufficient to permit expression of the fusion protein and permit the expressed fusion protein to aggregate if insoluble. The cell is lysed and the lysate is contacted with an SFP detector (e.g., a ccGFP detector provided herein), wherein the SFP detector and SFP tag complement to form a fluorescent protein complex, under conditions and for a time sufficient to allow self-complementation; and detecting fluorescence, wherein the presence of detectable fluorescence provides an indication that the protein of interest is soluble. In some examples, the SFP detector includes the amino acid sequence of any one of SEQ ID NOs: 1-3 and/or the SFP tag includes the amino acid sequence of SEQ ID NO: 4.

In additional embodiments, methods of quantifying an insoluble protein of interest in vitro are provided. In some examples, the methods include providing a polynucleotide construct comprising the coding sequence of a SFP tag (e.g. a ccGFP tag provided herein) fused to the coding sequence of the protein of interest and culturing a cell containing the polynucleotide construct under conditions permitting the expression of the SFP tag-protein of interest fusion and for a time sufficient to permit expression of the fusion protein and permit the expressed fusion protein to aggregate if insoluble. The method also includes lysing the cell, isolating the insoluble fraction from the lysate and solubilizing the insoluble fraction, for example, by chemical denaturation. The solubilized denatured insoluble protein fraction is resolubilized in a suitable diluent containing an SFP detector (e.g., a ccGFP detector disclosed herein), wherein the SFP detector and SFP tag complement to form a fluorescent protein complex, under conditions and for a time sufficient to allow self-complementation; and quantitatively detecting fluorescence in order to determine the insoluble protein quantity. In some examples, the SFP detector includes the amino acid sequence of any one of SEQ ID NOs: 1-3 and/or the SFP tag includes the amino acid sequence of SEQ ID NO: 4.

It will be understood that some background fluorescence can be present. For example, detecting the fluorescence (or lack thereof) of the complemented split-GFP protein can include detecting an increase (or decrease) in fluorescence compared to a control.

Additionally, the person of skill in the art will understand that the disclosed SFPs and fluorescent proteins have utility, for example, in known methods of using SFPs and fluorescent proteins. Such methods include those described in e.g., U.S. App. Pub. Nos. 2005/0221343, 2012/0282643, and 2015/0099271; and U.S. Pat. Nos. 7,666,606; and 7,585, 636, each of which is incorporated herein in its entirety, and are further described herein.

IV. Kits

Provided herein are kits useful for the various embodiments described herein. Kits may contain various materials and reagents (e.g., for practicing the methods described herein). For example, a kit may contain reagents including, without limitation, polypeptides or polynucleotides, cell transformation and transfection reagents, reagents and materials for purifying polynucleotides and polypeptides including lysis regents, protein denaturing and refolding reagents, as well as other solutions or buffers useful in carrying out the assays and other methods provided herein. Kits may also include control samples, materials useful in calibrating methods described herein, and containers, tubes, microtiter plates and the like in which assay reactions may be conducted. Kits may be packaged in containers, which may comprise compartments for receiving the contents of the kits, and may include instructions for conducting methods described herein or using the polypeptides and polynucleotides described herein.

For example, a kit may provide one or more SFP fragments or fluorescent proteins as described herein (including one or more proteins including or consisting of any one of SEQ ID NOs: 1-11), one or more nucleic acids encoding the one or more SFP fragments or fluorescent proteins (including vectors including the nucleic acids), cell strains suitable for propagating the constructs, cells pre-transformed or stably transfected with constructs encoding one or more SFP fragment or fluorescent proteins, and reagents for purification of expressed fusion proteins or nucleotides encoding an expressed fusion protein.

For example, a kit may provide a nucleic acid construct encoding an SFP tag (e.g., encoding SEQ ID NO: 4) and a multiple cloning site adjacent thereto, such that an encoding sequence inserted into the multiple cloning site results in a nucleic acid that encodes a protein of interest encoded by the encoding sequence fused with the SFP tag, and instructions for using the nucleic acid (e.g., instructions for carrying out the methods described herein). In another example, a kit may provide a nucleic acid construct encoding an SFP detector as described herein (e.g., encoding any one of SEQ ID NOs: 1-3) and a multiple cloning site adjacent thereto, such that an encoding sequence inserted into the multiple cloning site results in a nucleic acid molecule that encodes a protein of interest encoded by the encoding sequence fused with the SFP detector and instructions for using the nucleic acid (e.g., instructions for carrying out the methods described herein).

The kit can include a container and a label or package insert on or associated with the container. The label or package insert typically will further include instructions for use of the polypeptide, nucleic acid molecules, or expression vectors provided with the kit, for example for use in the methods disclosed herein. The instructional materials may be written, in an electronic form, or may be visual (such as video files).

EXAMPLES

The following examples are provided to illustrate particular features of certain embodiments, but the scope of the claims is not intended to be limited to those features exemplified.

Example 1

Engineering Split *Corynactis californica* Green Fluorescent Protein

This example presents a monomeric split green fluorescent proteins (ccGFP) engineered from a tetrameric GFP found in *Corynactis californica*.

Results

Engineering a monomeric and stable Corynactis California GFP protein scaffold Choosing a fluorescent protein

*Corynactis californica*, a bright red colonial anthozoan similar to sea anemones and scleractinian stony corals, expresses several fluorescent proteins in its morphs. One displays an as-yet-uncharacterized timer phenotype (slow conversion of chromophore from green to red) that varies according to expression conditions. The second red fluorescent protein has very poor fluorescence quantum yield. There are also a yellow and an orange fluorescent protein. Morphs of *C. californica* express at least two green fluorescent proteins. One is partially folded when expressed in *E. coli*, while the other is mostly misfolded and nonfluorescent. The *C. californica* GFPs were chosen for three reasons. First, the multimeric red proteins appeared to have less desirable features and the yellow and orange fluorescent proteins were poorly characterized. Second, previous work has shown that considerable engineering may be required to retain red fluorescent phenotypes while re-engineering monomeric mutants. Third, starting from a previous split GFP, we previously engineered a split YFP (T203Y), as well as an efficient split CFP (Y66W) that contains several additional obligate folding mutations. The insoluble ccGFP variant was chosen in particular as a stringent test of the prior approach for engineering efficient split fluorescent proteins, as well as to develop an orthogonal split fluorescent protein system for multiplex labeling in living cells.

Making a Monomeric, Cysteine-Free Scaffold

It was postulated that in order to be useful as a protein tagging and detection system, the split protein should be monomeric and have no free cysteines. Predicted monomerizing mutations (V127E, N192R, I194E) were introduced to ccGFP following published protocols and based on structural homology with monomeric Azami Green. The protein still failed to fold and was non-fluorescent when expressed in E. coli. Bright fluorescent colonies were obtained after six rounds of directed evolution using DNA shuffling, converging on a small number of sequences. The brightest engineered protein retained all six native cysteine residues. Mutating the cysteines (C20S, C71A, C73S. C104S, C153S, C175A) to eliminate unwanted disulfide bond formation in the unfolded protein (or subsequent split protein fragments), resulted in misfolding and loss of fluorescence. After three additional rounds of directed evolution and gene shuffling, bright colonies were again obtained. The optimal final version (ccGFP E6; SEQ ID NO: 5) contained 24 mutations compared to the wild type protein (FIG. 1A): L3M, V8L, C21S, K36N, K42Q, E50K, A63P. C71V, C73T, E100D, C104S, G105A, H110R, N121K, V127E, K149T, C153S, H171Q, C105A, D184N, N192R, I194K, A207T, and I210L. Interestingly, an N121K mutation present in the template as the result of a gene synthesis error was retained. The other gene synthesis error (H120Q) reverted to wildtype H120. None of the amino acids replacing the six cysteines reverted to cysteine, but two had further mutated, A71V and S73T. Gel filtration chromatography confirmed the protein migrated as a monomer at ~10 mg/ml (data not shown).

Engineering an Efficient Split System from the Engineered C. californica Scaffold Improving ccGFP 1-10 and Eliminating Autofluorescence The same strategy used to engineer split GFP was utilized. Using homology alignment with the structure (PDB 3ADF) of monomeric Azami GFP, the engineered ccGFP E6 protein scaffold was split into two pieces, the large ccGFP 1-10 E6 (amino acids 1-202 of SEQ ID NO: 5) and the small ccGFP S11 E6 (amino acids 205-221 of SEQ ID NO: 5). Strand ccGFP S11 E6 was solubly expressed as a C-terminal tag on the carrier protein sulfite reductase (SR). The ccGFP 1-10 E6 protein aggregated when expressed alone in E. coli at either 37° C. or 20° C. from a pET vector, and soluble lysates did not complement with SR-ccGFP S11 E6. Directed evolution of ccGFP 1-10 dramatically improved the complementation rate and solubility. Unexpectedly, this version, termed ccGFP 1-10 v1 (FIG. 1B; SEQ ID NO: 1), slowly gained fluorescence without the S11 fragment, (at about 1% the rate seen with excess ccGFP S11, FIG. 2A).

To reduce the autofluorescence, after replating the ccGFP 1-10 library from the final round of directed evolution, images of plates were aligned after ccGFP 1-10 expression (to observe ccGFP 1-10 autofluorescence), and after SR-ccGFP S11 expression (to observe full complementation fluorescence). Several colonies were identified (8 out of 20,000) with ccGFP 1-10 clones that were faint or non-fluorescent alone, but that became highly fluorescent after SR-ccGFP S11 E6 expression. The best of these was isolated and termed ccGFP 1-10 v2 (FIG. 1B; SEQ ID NO: 2).

Figure 2:
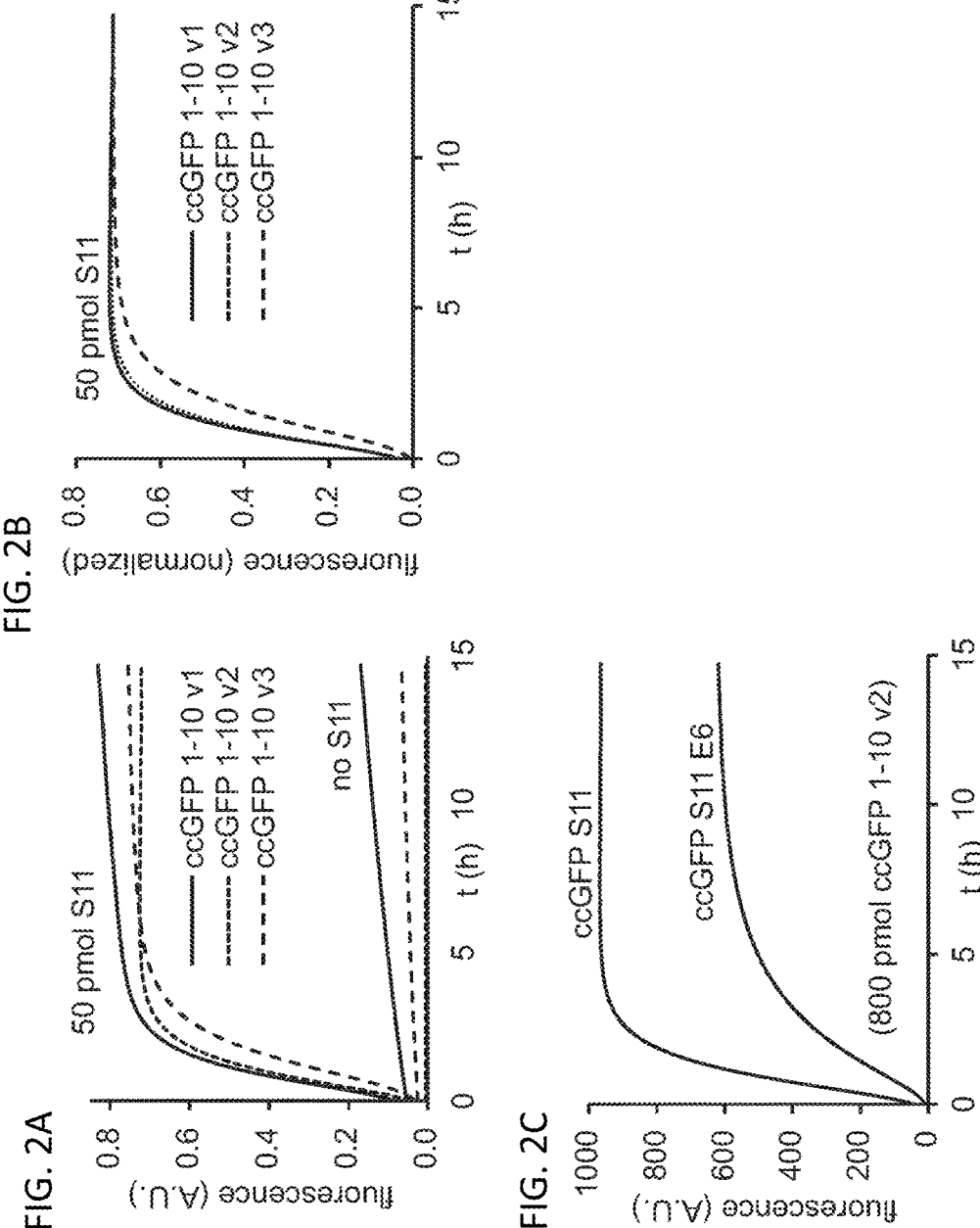
FIGS. 2A-2C are graphs showing complementation and autofluorescence of purified ccGFP 1-10 fragments.

Relative to ccGFP 1-10 v1, ccGFP 1-10 v2 had the additional mutations D78Y, Q85R, and A109V. This variant exhibited no detectable autofluorescence (FIG. 2A).

Improving ccGFP S11

In previous work engineering a two-part split GFP, it was found that the C-terminal GFP S11 wildtype dramatically reduced the solubility of hexulose phosphate synthase (HPS) from P. aerophilum, suggesting that the solubility and folding of this protein was sensitive to C-terminal split protein tags. Thus, HPS was used as 'bait' in a directed evolution schema in E. coli to discover improved mutants of ccGFP S11 for which the HPS-ccGFP S11 fusion solubility matched that of HPS alone. Libraries of ccGFP S11 variants as C-terminal fusions with HPS and ccGFP 1-10 v2 were expressed in succession in the same cells from independently inducible compatible plasmids to avoid false positives caused by cotranslational rescue of the folding of insoluble variants of HPS-ccGFP S11 that might occur with co-expressed ccGFP 1-10 v2 as previously noted for GFP. The brightest clones all contained the mutations D206E, V208I, and V221E, were brighter and matured faster compared to the ccGFP S11 E6, and balanced a lack of perturbation of fusion protein solubility with good complementation (FIG. 2C). This variant was designated ccGFP S11 (FIG. 1B; SEQ ID NO: 4).

Supercharging the ccGFP 1-10 Optima ccGFP 1-10 v1 and v2 were each about 50% soluble expressed at 37° C. from pET T7 plasmids. In an attempt to increase the solubility, some neutral or hydrophobic surface residues of ccGFP 1-10 v1 were mutated to charged residues such as Glu and Arg. The new version, ccGFP 1-10 v3, carried 8 additional negatively charged residues relative to ccGFP 1-10 v1: S4E, N23D, T28E, Q41E, S43E, N142E, S153E, T162E (FIG. 1B; SEQ ID NO: 3).

Characterization of Split ccGFP Fragments by Renaturation, Autofluorescence, and Complementation Renaturation Yield after Unfolding GdnHCI-denatured inclusion bodies of ccGFP 1-10 variants were renatured in 100 mM Tris, 150 mM NaCl, 10% v/v glycerol (TNG) buffer. For the same amount of inclusion bodies (~75 mg/tube), after dilution of the denatured inclusion bodies in 20 ml TNG, ccGFP 1-10 v1 yielded ~0.46 mg/ml, while ccGFP 1-10 v2 yielded ~0.85 mg/ml. The −8 charged version ccGFP 1-10 v3 yielded ~2.5 mg/ml, a 67% yield. To facilitate comparison of specific activities of complementation with S11, for subsequent experiments, all refolded ccGFP 1-10 samples were concentrated or diluted to ~0.75 mg/ml.

Autofluorescence of ccGFP 1-10 Variants

Figures 7A, 7B, 7C, 7D:
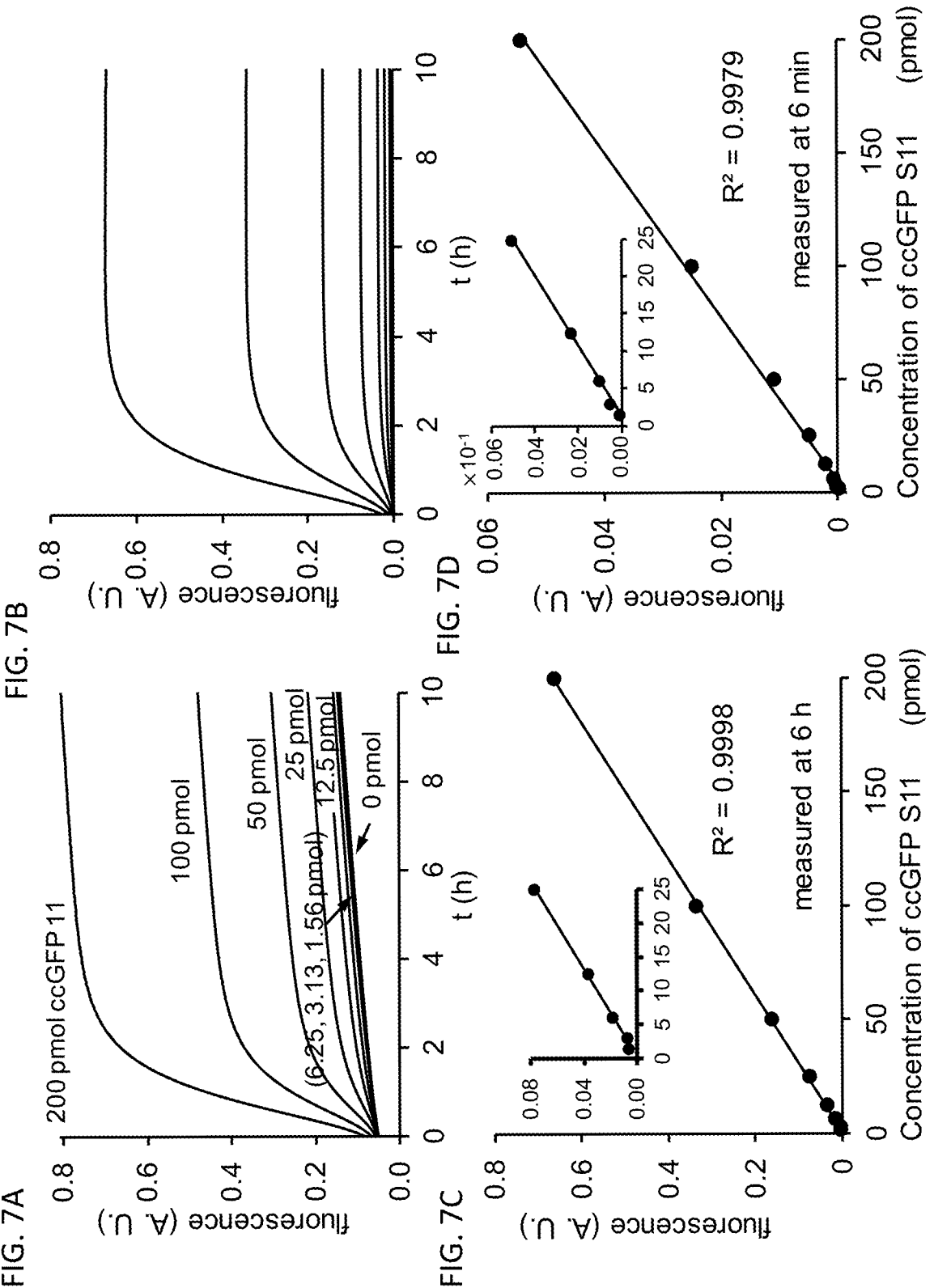
FIGS. 7A-7D are graphs showing complementation of purified ccGFP S11 fragments.

The development of autofluorescence of the ccGFP 1-10 variants alone over time was monitored. Referring to FIG. 2A, autofluorescence was significant for ccGFP 1-10 v1 and ccGFP 1-10 v3 but not ccGFP 1-10 v2. To test the relative in vitro complementation efficiency of the different ccGFP 1-10 variants, the same amount of SR-ccGFP S11 (50 μmol) was added to a large molar excess of ccGFP 1-10 (800 μmol) (FIG. 2A). After subtraction of the blank autofluorescence progress curves as appropriate, both ccGFP 1-10 v1 and ccGFP 1-10 v2 had similar complementation kinetics, while the −8 charged ccGFP 1-10 v3 was slower (FIG. 2B). FIG. 7 shows the appearance of raw fluorescence progress curves for different concentrations of SR-ccGFP S11 complemented with ccGFP 1-10 v3. The background autofluorescence progress curve for ccGFP 1-10 v3 could be easily subtracted. The same amount of either SR-ccGFP S11 E6 or SR-ccGFP S11 (50 μmol) was added to the plate and a large molar excess of ccGFP 1-10 v2 was added (800 µmol). SR-ccGFP S11 complemented significantly faster than SR-ccGFP S11 E6 (FIG. 2C).

Use of the Split ccGFP System for In Vitro Protein Quantification

Figure 3:
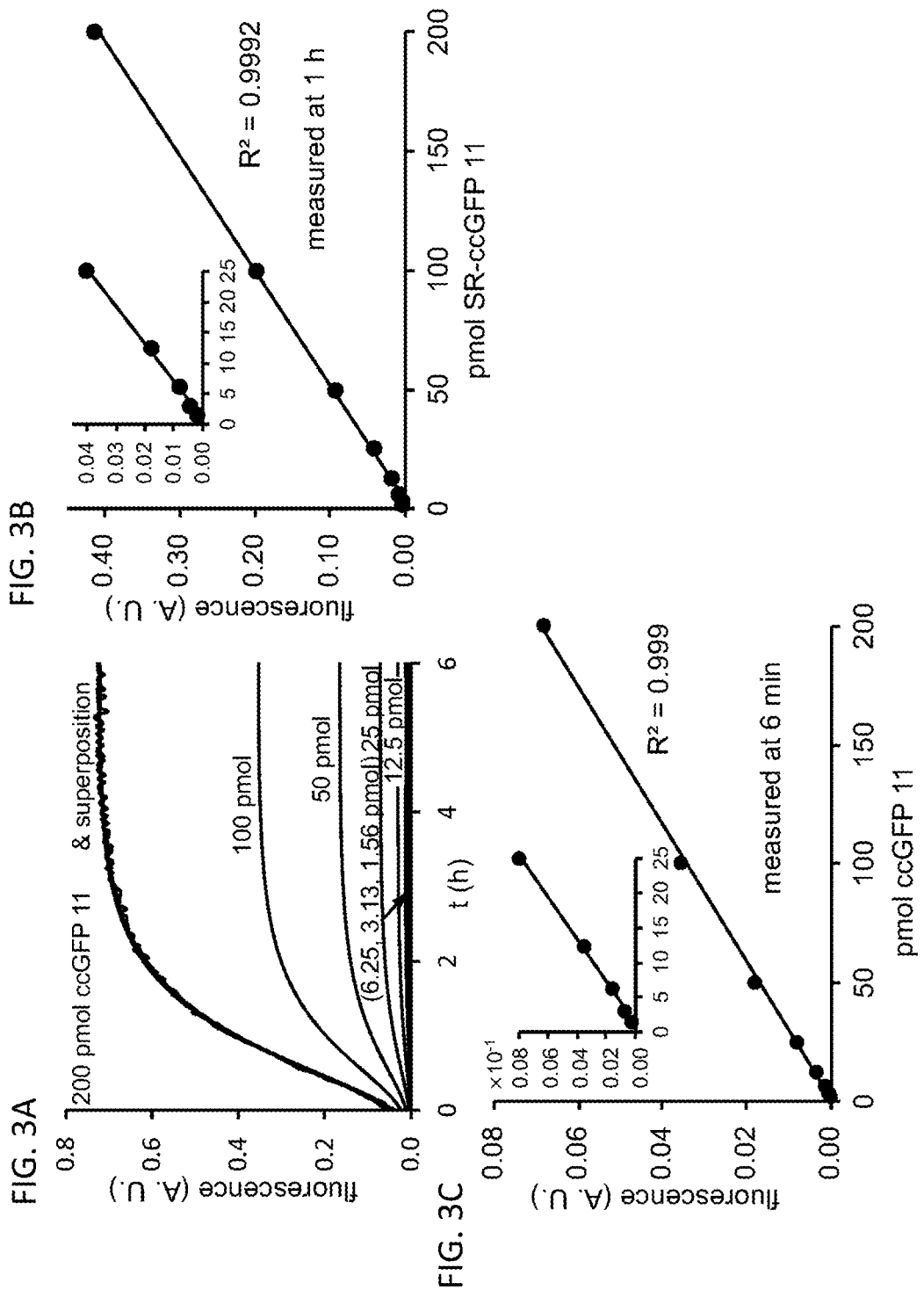
FIGS. 3A-3C are graphs showing in vitro characterization of split ccGFP complementation.
Figures 8A, 8B, 8C, 8D:
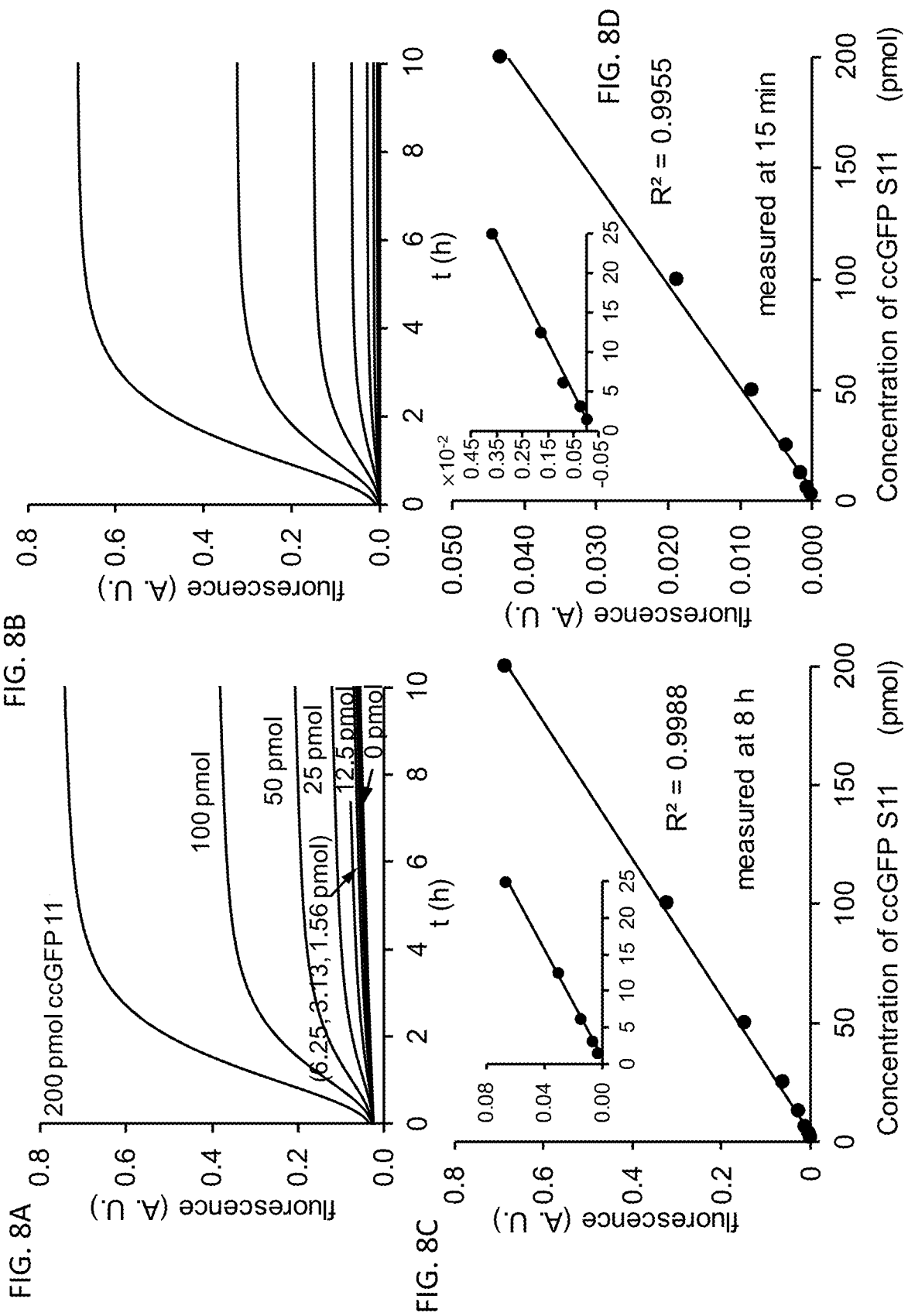
FIGS. 8A-8D are graphs showing complementation of purified ccGFP S11 fragments.
Figure 9:
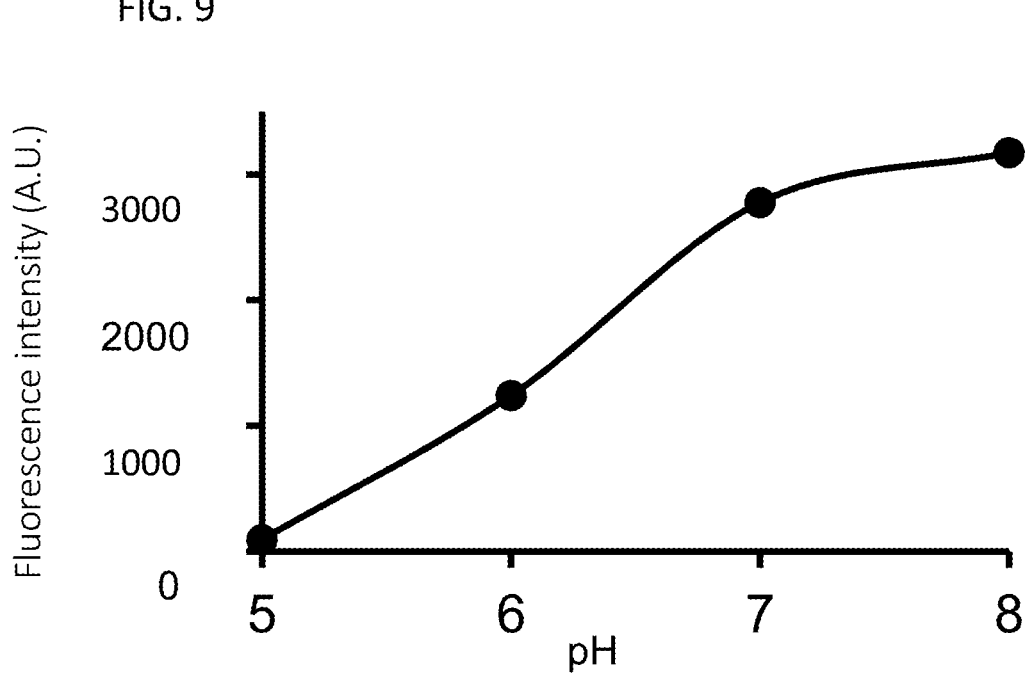
FIG. 9 shows pH dependence of the complementation of ccGFP 1-10 v2 with ccGFP S11. Reactions were initiated by mixing 25 pmol SR-ccGFP S11 in 20 µl aliquot with 180 µl aliquot containing 800 pmol of ccGFP 1-10 v2, each diluted in the appropriate pH buffer (see Methods).
Figure 10:
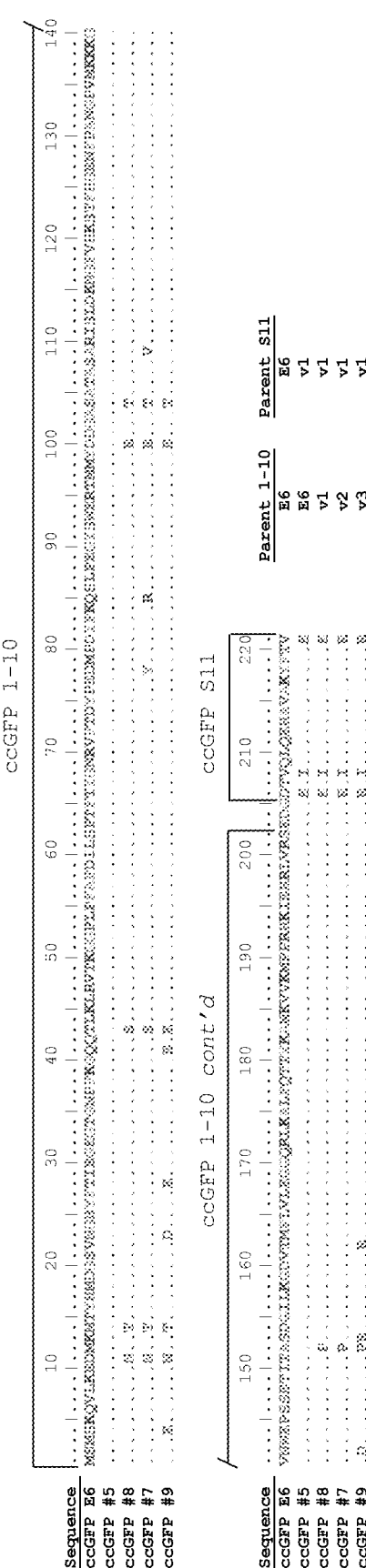
FIG. 10 shows amino acid sequences of full-length ccGFP E6 and ccGFPs carrying mutations from the split fragments. ccGFP E6 (SEQ ID NO: 5), ccGFP #5 (SEQ ID NO: 8), ccGFP #8 (SEQ ID NO: 6), ccGFP #7 (SEQ ID NO: 9), ccGFP #9 (SEQ ID NO: 7).

Fluorescence progress curves for complementation of purified SR-ccGFP S11 and ccGFP 1-10 v2 were measured in 200 µl reactions in a microtiter plate (FIG. 3). Potential higher-order kinetic effects were avoided by initiating the complementation using a high concentration and large molar-excess of ccGFP 1-10 (800 µmol). Progress curves over a wide concentration range could be superimposed by linear scaling (FIG. 3A). Over the range of S11 analyte tested (1.56-200 µmol) it was not necessary to wait until the reactions approached their asymptotic limit (~6 h) to generate calibration curves. For example, robust linear calibration curves were easily generated at 1 h (FIG. 3B), or even as soon as 6 min (FIG. 3C) after the start of complementation. Progress curves were also measured for SR-ccGFP S11 vs. either ccGFP 1-10 v1 (FIG. 7A) or ccGFP 1-10 v3 (FIG. 8A). After subtraction of the blank progress curves due to formation of intrinsic fluorescence (no SR-ccGFP S11) (FIGS. 7B and 8B), robust calibration curves could be generated (FIGS. 7C-7D and 8C-8D). The efficiency of complementation was measured as a function of pH (FIG. 9). The complementation rate was highest above pH 7.0, decreasing linearly with decreasing pH. Below pH 5.0 complementation was inefficient.

Expression and Solubility Screens of 18 Control Proteins from P. Aerophilum

Figure 4:
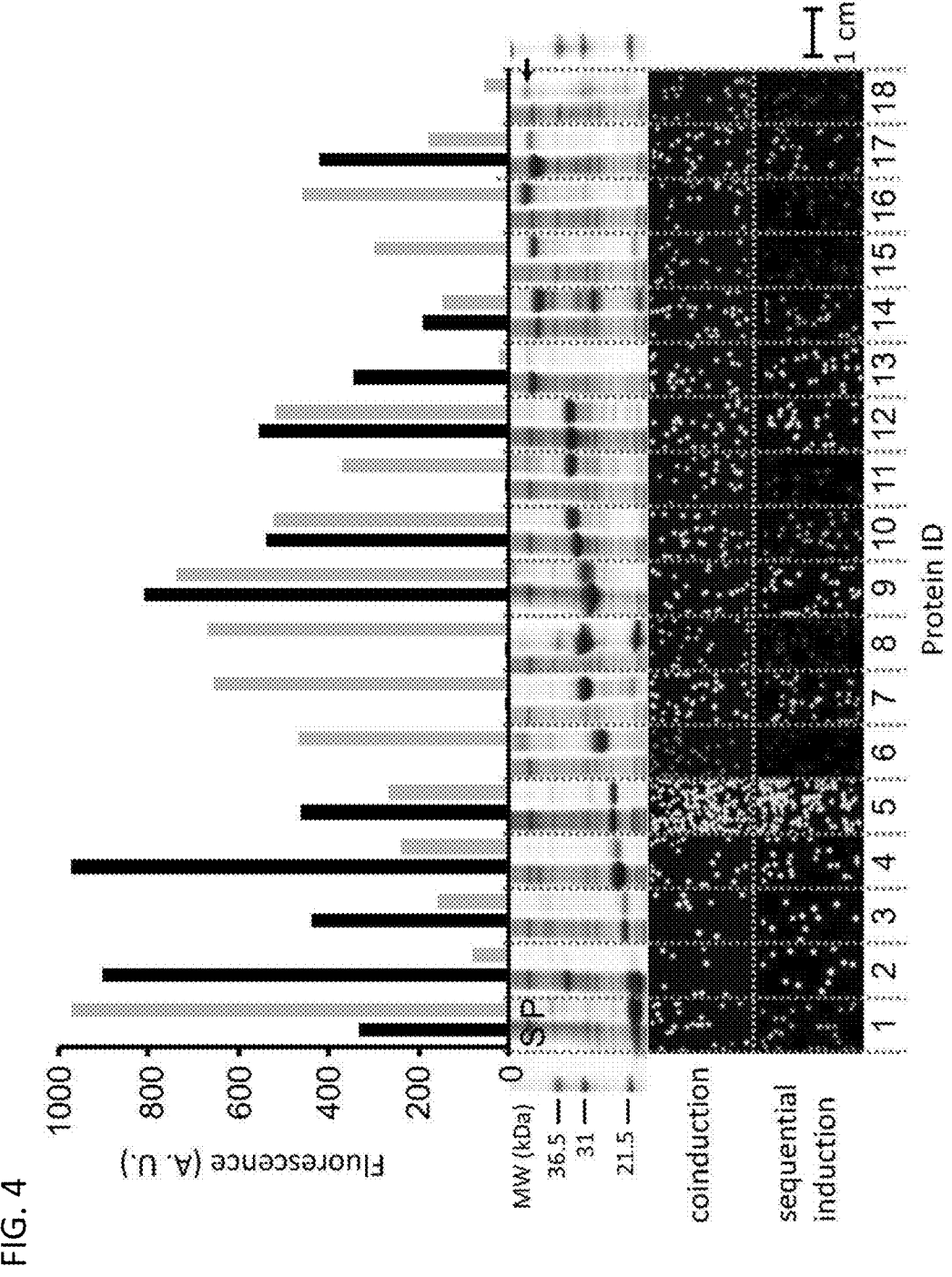
FIG. 4 shows in vitro protein quantification and in vivo protein expression and solubility screens. Protein quantification of eighteen P. aerophilum test proteins (see Table 1) expressed as N-terminal fusions with ccGFP S11 from the strong T7 promoter (bar graph, top). The ccGFP fragment complementation assay fluorescence of soluble (black bars) and unfolded pellet fractions (gray bars) using ccGFP 1-10 v2 (top). Arbitrary fluorescence units (A. U.). SDS-PAGE of the corresponding soluble(S), and pellet fractions (P) (middle). Note that protein #8, tartrate dehydratase β-subunit, shows a second lower band at ~13 kDa. #14, nirD protein, shows secondary bands at ~27 kDa and ~13 kDa. In vivo solubility and expression screen using split ccGFP (lower). The same P. aerophilum test proteins cloned with a C-terminal ccGFP S11 tag on tet promoter plasmid, in *E. coli* BL21 (DE3) strain carrying a pET plasmid for expression of ccGFP 1-10 v2. Fluorescence images of colonies on plates after total expression screen by coinduction of the tagged constructs and ccGFP 1-10 v2 (upper row of colonies); or after soluble expression screen by transient expression of the tagged constructs followed by expression of the ccGFP 1-10 v2 (lower row of colonies). Note 1 cm scale bar (lower right) illustrating the size of the colonies.

To test the utility of the split ccGFP screen for quantifying protein expression in vitro, 18 control proteins from P. aerophilum (Table 1) with different expression and solubility levels, carrying the C-terminal ccGFP S11 tag (SEQ ID NO: 4), were expressed in E. coli at 37° C. from pET vectors using the strong T7 promoter, and split into soluble and pellet fractions. Aliquots of the soluble fractions and solubilized denatured inclusion bodies, processed to allow direct comparison, were complemented with ccGFP 1-10 v2 and the final fluorescence values were measured (FIG. 4, top). The final fluorescence was reflective of the amount of the corresponding protein in the soluble and inclusion body fractions as revealed by SDS-PAGE (FIG. 4, middle). Since several of the urea-solubilized inclusion bodies visibly aggregated soon after dilution in the assay buffer, the successful complementation implies that the ccGFP 1-10 fragment rapidly binds the S11 tag during the dilution step before the formation of insoluble aggregates, committing the chromophore to form regardless of the subsequent solubility of the complex.

TABLE 1

Effect of split fluorescent protein S11 tags on the solubility of eighteen proteins from *Pyrobaculum aerophilum*.

| Protein ID | Protein | MW | NF | GFP S11 M3 | ccGFP S11 |
|---|---|---|---|---|---|
| | | | | Fraction soluble | |
| 1 | DNA-directed RNA polymerase | 12.5 | 0.05 | 0.10 | 0.10 |
| 2 | Sulfite reductase (dissimilatory subunit) | 12.7 | 1.00 | 1.00 | 1.00 |
| 3 | c-type cytochrome biogenesis factor | 14.4 | 0.77 | 0.65 | 0.75 |
| 4 | Translation initiation factor | 15.4 | 0.40 | 0.45 | 0.65 |
| 5 | Ribosomal protein S9p | 16.4 | 0.70 | 0.75 | 0.50 |
| 6 | Polysulfide reductase subunit | 21.0 | 0.00 | 0.00 | 0.00 |

TABLE 1-continued

Effect of split fluorescent protein S11 tags on the solubility of eighteen proteins from *Pyrobaculum aerophilum*.

| Protein ID | Protein | MW | NF | GFP S11 M3 | ccGFP S11 |
|---|---|---|---|---|---|
| | | | | Fraction soluble | |
| 7 | Nucleoside diphosphate kinase | 21.6 | 0.00 | 0.10 | 0.00 |
| 8 | Tartrate dehydratase b-subunit | 23.8 | 0.00 | 0.00 | 0.00 |
| 9 | 3-hexulose 6-phosphate synthase | 23.1 | 0.65 | 0.60 | 0.65 |
| 10 | Hydrogenase formation protein hypE | 26.8 | 0.35 | 0.55 | 0.55 |
| 11 | Methyltransferase | 29.3 | 0.00 | 0.05 | 0.00 |
| 12 | Chorismite mutase | 29.3 | 0.70 | 0.70 | 0.65 |
| 13 | Tyrosine t-RNA synthetase | 36.0 | 0.95 | 0.95 | 0.95 |
| 14 | nirD protein | 36.7 | 0.70 | 0.45 | 0.25 |
| 15 | Soluble hydrogenase | 37.3 | 0.00 | 0.00 | 0.00 |
| 16 | Aspartate-semialdehyde dehydrogenase | 37.4 | 0.00 | 0.00 | 0.00 |
| 17 | Phosphate cyclase | 37.4 | 0.80 | 0.90 | 0.85 |
| 18 | Purine-nucleoside phosphorylase | 41.7 | 0.05 | 0.00 | 0.00 |

MW = theoretical molecular weight (kDa) calculated from amino acid sequence.
Fraction soluble = fraction of total protein found in the soluble lysate as determined by SDS-PAGE densitometry for: non-fusion (NF); fused with C-terminal GFP S11 M3; or C-terminal ccGFP S11.
Relative uncertainty is ±5%, average of three replicates.

Estimating Total Protein Expression In Vivo

To estimate total expression in living E. coli, the C-terminally ccGFP S11-tagged protein (expressed from the moderately strong AnTET regulated promoter) and the ccGFP 1-10 v2 detector protein (expressed from the very strong IPTG-inducible LacUV/T7 promoter) were co-expressed. Referring to FIG. 4 (bottom), upper row of fluorescent colonies, the fluorescence could be easily detected regardless of the solubility of the protein (as estimated from the SDS-PAGE of the soluble and pellet fractions of the same protein expressed alone from the strong T7 promoter (FIG. 4, (middle)). This is consistent with a model where the 1-10 fragment can rapidly bind the S11 tag as soon as it appears in the cell, committing the complex to folding and chromophore formation regardless of the subsequent fate (soluble or aggregated) of the S11-tagged protein of interest. As expected, colonies expressing protein #6 (polysulfide reductase subunit) were fainter than colonies expressing the other 17 control proteins, because its expression leads to the accumulation of large amounts of a red product, absorbing the blue 488 nm excitation light.

Estimating Soluble Protein Expression In Vivo

To estimate soluble expression in an E. coli colony assay, the S11-tagged proteins were expressed first from the moderate AnTET regulated promoter, then the expression was shut off. After resting for 1 h to allow the proteins to remain soluble or become aggregated according to their intrinsic properties, and for any remaining AnTET inducer to diffuse out, the ccGFP 1-10 v2 detector protein was then expressed from the strong T7 promoter to help insure a molar excess of the 1-10 protein. Under these conditions, the 1-10 fragment should only bind soluble and accessible S11 tagged protein molecules. Referring to FIG. 4, (lower row of fluorescent colonies), with the exception of protein #7, nucleoside diphosphate kinase (see below), the fluorescence was reflective of soluble expression as estimated from the SDS-PAGE of the soluble and pellet fractions of the same protein expressed alone from the stronger T7 promoter (FIG. 4, (middle), and Table 2). The in vivo solubility of protein #7 is higher from the moderate AnTET regulated promoter (based on colony fluorescence, FIG. 4 bottom row of colonies) compared to its expression from the strong T7 promoter (SDS gel lanes, FIG. 4, middle, and Table 2). This is consistent with earlier observations using SDS-PAGE that showed protein #7 tagged with GFP S11 M3 is partially soluble as expressed from the moderate pTET AnTET promoter, and insoluble expressed from pET T7 promoter. Taken together, the behavior of the 18 control proteins tagged with the ccGFP S11 is consistent with earlier findings with the GFP S11 M3 fragment, suggesting that the optimized ccGFP S11 tag does not strongly perturb the solubility behavior of the fusion proteins.

Testing Cross-Complementation Between GFP and ccGFP Split Protein Fragments

Figure 5:
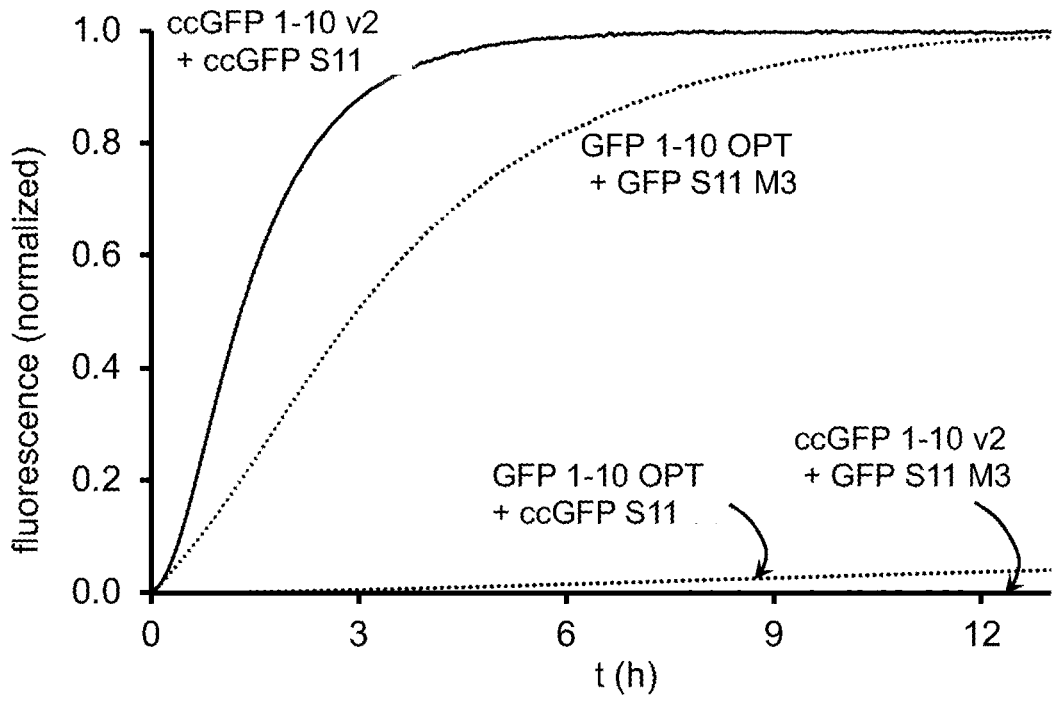
FIG. 5 is a graph showing normalized progress curves for complementation of cognate and non-cognate ccGFP and GFP fragments. Rapid complementation of cognate fragments (upper curves). ccGFP 1-10 v2 and SR-ccGFP S11 (upper solid line); GFP 1-10 OPT and SR-GFP S11 M3 (upper dotted line). GFP fragments are from the original split GFP derived from *A. victoria*. Weak complementation between non-cognate fragments (bottom curves). Complementation between ccGFP 1-10 v2 and its non-cognate fragment SR-S11 M3 is not detectable and the trace is at the baseline (bottom solid line). Complementation of GFP 1-10 OPT with the non-cognate fragment ccGFP S11 (lower dotted line) is ~4% of the final value for the cognate GFP S11 fragment (upper dotted line). Complementation was initiated by mixing 800 pmol of each 1-10 fragment with 50 pmol of S11 fragment in 200 μl reaction wells.

To test the ability of ccGFP fragments to recognize GFP fragments and vice. versa, complementation reactions were set up between the non-cognate pairs, e.g., ccGFP 1-10 v2 with GFP S11 M3 (Cabantous et al., *Nat Biotechnol* 23, 102-107, 2005), and GFP 1-10 OPT (Cabantous et al., *Nat Biotechnol* 23, 102-107, 2005) with ccGFP S11 (FIG. 5). Complementation reactions were also set up between cognate pairs of fragments e.g., ccGFP 1-10 v2 with ccGFP S11, and GFP 1-10 OPT with GFP S11 M3. Under the conditions of the assay, the GFP 1-10 OPT fragment weakly complemented with ccGFP S11 (FIG. 5). Notably this reaction had not reached completion at 13 h, at which time fluorescence was ~4% that from its cognate interaction with GFP S11 M3. Under the same conditions, ccGFP 1-10 v2 did not detectably complement with GFP S11 M3 (FIG. 5).

Double-Labeling Experiments

Figure 6:
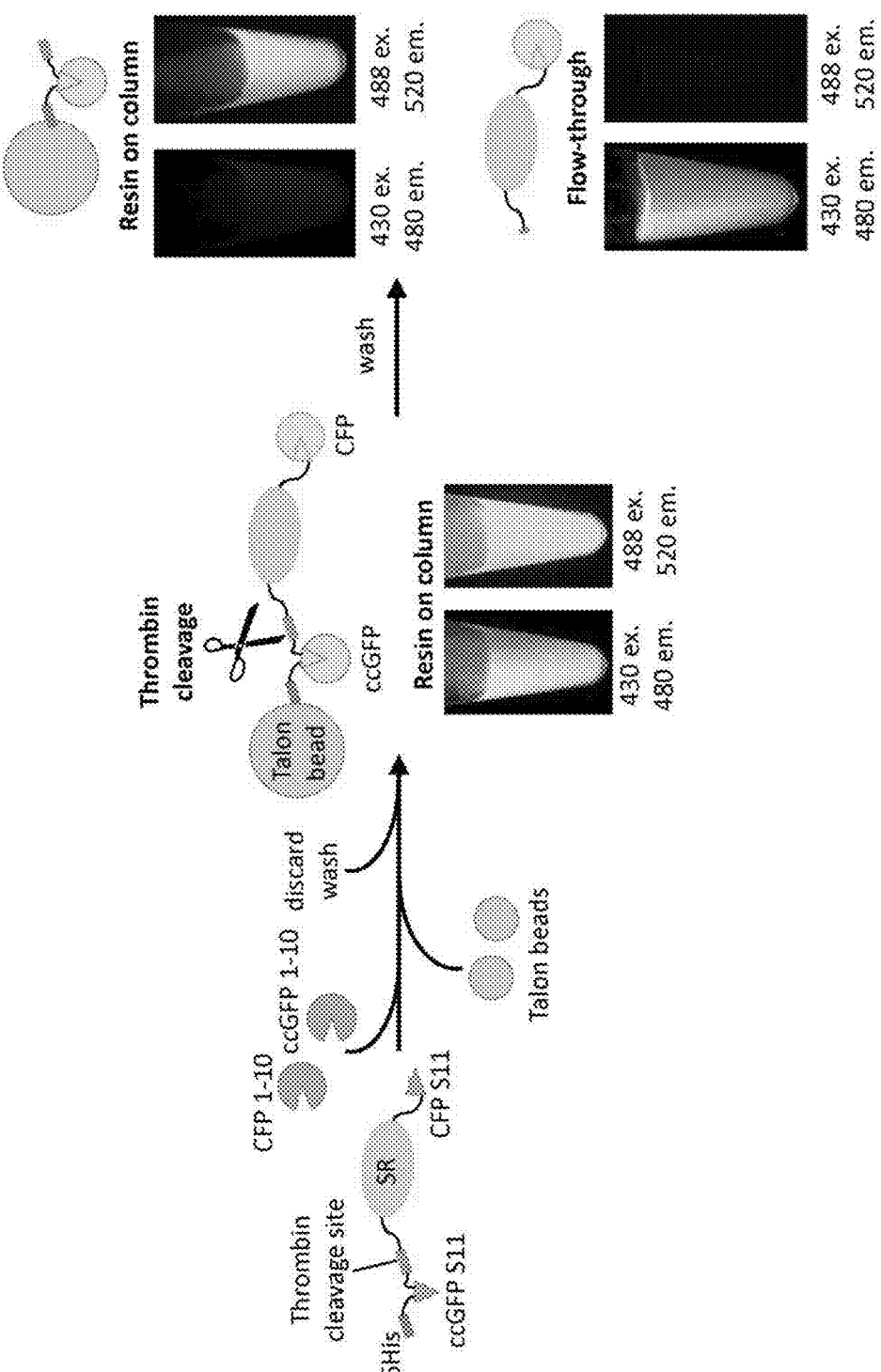
FIG. 6 is a schematic diagram showing an exemplary double-labeling experiment with split CFP and ccGFP. Sulfite reductase with an N-terminal 6HIS and ccGFP S11 tag, and a C-terminal CFP S11 M3 tag was complemented with an excess of CFP 1-10 OPT and ccGFP 1-10 v2 (left). Talon metal affinity beads were added to capture the complex, washed, and the beads imaged to show CFP and GFP bound (middle). After cleavage of the protein on the beads by added thrombin, the beads were washed and the resin and flow through imaged to reveal where the CFP and GFP localized (right). As expected, the ccGFP was retained on the beads (upper right), while the CFP was found in the flow-through (lower right).

To ascertain the utility of the new split ccGFP in cyan and green fluorescent protein double-labeling experiments, the soluble protein sulfite reductase (SR) from P. aerophilum was tagged with an N-terminal ccGFP S11, and a C-terminal CFP S11 M3 fragment. The construct had an N-terminal 6His tag for capture by metal affinity resin, followed by a thrombin tag for selective cleavage and release from the bead. After mixing the tagged complex with CFP 1-10 OPT and ccGFP 1-10 v2, the fluorescent complex was captured on Talon resin (FIG. 6). Imaging the washed beads with the appropriate excitation and emission filters revealed the expected cyan and green fluorescence. The complemented CFP was recovered in the wash after cleavage by thrombin, while the ccGFP was retained on the resin via the 6His tag (FIG. 6).

DISCUSSION

The optimized ccGFP 1-10 v2 contains 32 mutations relative to the wild type ccGFP protein, and 9 mutations compared to the folding optimized full-length ccGFP E6. Most of the mutations are likely important for the enhanced phenotypes, as unlike conventional error prone mutagenesis where mutants are not subjected to recombination, the DNA shuffling (fragmentation and homologous recombination of the 30 best performing clones per cycle of evolution) used here typically results in 'backcrossing as you go', that is, removal of non-essential or neutral stochastic mutations and amplification of beneficial mutations.

Optimized ccGFP S11 contains three mutations relative to the starting ccGFP S11 E6 fragment. These significantly improved complementation with the 1-10 fragment. The autofluorescence phenotype in ccGFP 1-10 v1 and v3 is intriguing. Apparently, the chromophore residues in the 1-10 fragment are capable of forming a population of fluorescent states even without the S11 strand. Autofluorescence of the ccGFP 1-10 v1 can be eliminated by three mutations (D78Y, Q85R, and A109V, yielding ccGFP 1-10 v2) without strongly effecting complementation.

The split ccGFP 1-10 v2 and S11 complemented nearly 3-fold faster than the corresponding split GFP fragments, reaching 80% completion in 2 h rather than 6 h. When quantifying S11-tagged proteins in lysates, it was not necessary to wait until the complementation reaction asymptotically approaches completion. Robust linear calibration curves could be generated at 1 h or as early as 6 min. The complementation was sufficiently robust to allow quantification of solubilized inclusion bodies. The −8 charged variant of ccGFP 1-10 v1, ccGFP 1-10 v3, yielded more soluble protein compared to ccGFP 1-10 v2 during refolding (2.5 mg/ml vs. 0.85 mg/ml), and might be preferred for in vitro assays, since it is a simple matter to eliminate the interference of autofluorescence by subtracting a blank progress curve measured for the 1-10 alone. While the charged variant exhibited slightly lower autofluorescence compared to ccGFP 1-10 v1, it complemented more slowly than either ccGFP 1-10 v1 or v2. In living cells, transient expression of S11 tagged proteins followed by expression of the 1-10 fragment gave colony fluorescence reflective of soluble protein. In contrast, co-expression of S11 tagged protein along with 1-10 produced fluorescence proportional to total expression.

The split ccGFP is nearly orthogonal to split GFP. While ccGFP 1-10 does not complement with GFP S11, GFP 1-10 complements ccGFP S11 at about 4% the efficiency of its cognate interaction with GFP S11. Despite this, the strong preference for cognate interactions should facilitate a variety of double-labeling or multiplex experiments for split CFP and ccGFP.

Methods

Engineering a Monomeric Version of ccGFP for Improved Solubility and Folding.

*C. californica* GFP (ccGFP) wildtype protein was predicted to be a tetramer, predicted monomerizing mutations (V127E, N192R, I194E) were introduced following published protocols based on structural homology with monomeric Azami Green (Karasawa et. al., J Biol Chem 278, 34167-3417, 2003). The gene ordered from Blue Heron contained two unexpected wobble mutations H120Q and N121K (CAT to CAA, and AAT to AAA respectively). This wildtype ccGFP full length protein was evolved to improve solubility and folding by directed evolution. The DNA coding ccGFP was PCR amplified using vector flanking primers and was subjected to DNA fragmentation and shuffling using published protocols (Cabantous et al., Nat Biotechnol 23, 102-107, 2005). The library of DNA plasmids was transformed into E. coli BL21 (DE3) gold (Novagen) competent cells for protein expression. The 1.0 OD600 nm cell stock frozen library was diluted by two sequential 400-fold dilutions and 600 μl plated on each of five supported nitrocellulose membranes resting on 150 mm diameter Bauer plates containing Luria-Bertani (LB) agar supplemented with 50 μg kanamycin/ml media. Cells were grown overnight at 32° C. and proteins were expressed by transferring the membrane colony side up to LB agar plates containing 50 μg kanamycin/ml media and 1 mM isopropyl-β-D-1-thiogalactopyranoside (IPTG) for 3 h at 37° C. Clones (~30-40) displaying the brightest fluorescence (488 nm excitation/520 nm emission) were selected, grown overnight and frozen as 20% glycerol/LB freezer stocks at −80° C. Pooled plasmid preps of these clones served as templates for PCR for the next round of evolution. After six rounds of directed evolution, sequences of the brighter 30-40 constructs were confirmed by DNA sequencing and the brightest clone was chosen for subsequent modification. The six cysteine residues were mutated to alanine or serine by primer-directed PCR (C20S, C71A, C73S, C104S, C153S, C175A). The protein was subjected to another three rounds of directed evolution using the same protocol as indicated and the final, brightest, monomeric clone named ccGFP E6 was chosen for engineering the split version of the protein. Engineering an Efficient Split ccGFP 1-10.

Using ccGFP E6 (SEQ ID NO: 5) as starting scaffold, protein was first split into two fragments: ccGFP S11 E6 (amino acids 205-221 of SEQ ID NO: 5) and ccGFP 1-10 E6 (amino acids 1-202 of SEQ ID NO: 5). ccGFP 1-10 E6 aggregated and was primarily found in inclusion bodies. Neither refolded inclusion bodies nor soluble cell lysates fractions could associate with ccGFP S11 E6 to form a full length, fluorescent protein. ccGFP 1-10 E6 was engineered using directed evolution as previously published and described (Cabantous et al., Nat Biotechnol 23, 102-107, 2005) with the following modifications. Briefly, the DNA library of shuffled ccGFP 1-10 was ligated into an in-house engineered pTET-SpecR with ColEl origin, (which expresses the tetR regulator), where expression is regulated by addition of anhydrotetracycline (AnTET). The plasmid library was transformed into *E. coli* BL21 (DE3) gold (Novagen) competent cells containing the sulfite reductase-ccGFP S11 E6 tagged protein on a modified p15A vector with kanamycin resistance marker where the protein of interest is inducible with IPTG. The 1.0 OD600 nm cell stock frozen library was diluted by two sequential 400-fold dilutions and 600 μl plated on each of 5 supported nitrocellulose membranes resting on 150 mm diameter Bauer plates containing Luria-Bertani (LB) agar supplemented with 50 μg kanamycin/ml and 50 μg spectinomycin/ml. Cells were grown overnight at 32° C. to keep colony sizes below 0.5 mm diameter, and proteins were expressed by transferring the membrane colony side up to an LB agar plate containing 50 μg kanamycin/ml, 50 μg spectinomycin/ml and 350 ng/ml AnTET for 3 hours at 37° C. to express the ccGFP 1-10 library. The membrane was then transferred to an agar plate containing only kanamycin and spectinomycin for 1 h to allow the AnTET to diffuse out of the colonies to shut off expression of the ccGFP 1-10 library. This strategy allows each mutant protein to either remain soluble, or aggregate according to their inherent propensity. The membrane was then moved onto a new LB/agar plate containing the same antibiotics plus 1 mM IPTG to induce expression of the SR-ccGFP S11 E6 for complementation of any soluble (mutant) ccGFP 1-10. Clones exhibiting the most rapid development of fluorescence, indicating soluble and functional ccGFP 1-10 mutants, were selected and stored as freezer stocks at −80° C. in 20% glycerol/LB medium. Brighter clones were grown in 1 ml LB liquid culture containing 50 μg kanamycin/ml, 50 μg spectinomycin/ml to 0.3 OD600 nm and induced with 350 ng/ml AnTET for 3 hours at 37° C. to express just the ccGFP 1-10, and after sonication and centrifugation, 20 μl of the 350 μl soluble cell extract fractions were screened for better complementation efficiency in an in vitro assay with an excess amount of purified SR-ccGFP S11 E6.

The best 30 candidates were pooled, plasmid prepared, then PCR-amplified using flanking primers in the vector backbone surrounding the ccGFP 1-10 insert, and subjected to three additional rounds of directed evolution. Mutations of the top 24 optima were confirmed by DNA sequencing, revealing the population had converged on a small subset of solutions. All the brightest optima showed some autofluorescence (development of fluorescence in the absence of ccGFP S11 E6). The brightest and fastest version was termed ccGFP 1-10 v1 (SEQ ID NO: 1). To eliminate the autofluorescence, the top pool from the final round was replated, and imaged after ccGFP 1-10 expression but prior to ccGFP S11 expression, and imaged again after ccGFP S11 expression. After alignment of the images in NIH Image, the brightest clones also exhibiting the largest dynamic range (faintest prior to, and brightest after ccGFP S11 expression) were picked and sequenced. One such clone, ccGFP 1-10 v2 (SEQ ID NO: 2), was essentially non-fluorescent after expression alone. Using alignment with the structural homolog monomeric Azami Green, GFP 1-10 v3 (SEQ ID NO: 3), with a net-8 charge relative to ccGFP 1-10 v1, was made by primer-directed mutagenesis, mutating neutral surfaces residues predicted to be on the surface of the protein to charged residues such as glutamate and aspartate: S4E, N23D, T28E, Q41E, S43E, N142E, S153E, T162E.
Engineering an Efficient ccGFP S11.

The ccGFP S11 E6 fragment was expressed as a C-terminal fusion with the 'bait protein' hexulose phosphate synthase (HPS), (previously shown to become less soluble with various split fluorescent protein fragments as C-terminal fusions) as HPS-ccGFP S11 E6, and ligated into the in-house engineered pTET-SpecR with ColEl origin, (which expresses the tetR regulator), where expression is regulated by addition of AnTET. HPS-ccGFP S11 fusions were amplified by PCR and shuffled using published protocols (Cabantous et al., Nat Biotechnol 23, 102-107, 2005). For each round of directed evolution, the library of HPS-ccGFP S11 (containing mutants of ccGFP S11) was transformed into *E. coli* BL21 (DE3) gold (Novagen) competent cells expressing the ccGFP 1-10 v2 protein on a modified p15A vector with kanamycin resistance marker where the protein of interest is inducible with IPTG. Optima were screened in vivo using a sequential induction protocol. Briefly, the 1.0 OD600 nm cell stock frozen library was diluted by two sequential 400-fold dilutions and 600 μl plated on each of five supported nitrocellulose membranes resting on 150 mm diameter LB agar Bauer plates supplemented with 50 μg kanamycin/ml and 50 μg spectinomycin/ml. Cells were grown overnight at 32° C. to keep colony sizes below 0.5 mm diameter, and proteins were expressed by transferring the membrane colony side up to an LB agar plate containing 50 μg kanamycin/ml, 50 μg spectinomycin/ml and 350 ng/ml AnTET for 3 hours at 37° C. to express the HPS-ccGFP S11 library. Each membrane was then transferred colony side up to an agar plate containing 50 μg kanamycin/ml, 50 μg spectinomycin/ml for 1 h to allow the AnTET to diffuse out of the colonies, shutting off expression of the HPS-ccGFP S11. This sequential strategy allowed any mutants that interfered with the solubility of the HPS to become insoluble prior to expression of the ccGFP 1-10 in the next step. Next, membranes were moved colony side up to an LB agar plate containing 50 μg kanamycin/ml, 50 μg spectinomycin/ml and 1 mM IPTG for 2 h to induce expression of the complementary ccGFP 1-10 v2 from the pET plasmid. Brighter clones were selected, grown at 37° C. to 0.3 $OD_{600nm}$ in 1 ml LB liquid cultures containing 50 μg kanamycin/ml and 50 μg spectinomycin/ml, and induced at 37° C. for 3 h with 350 ng/ml AnTET only to express just the HPS-ccGFP S11. Note that the medium must not contain lactose, and the cultures should not be allowed to overgrow prior to AnTET induction, otherwise the LacUV/T7 expression of the unwanted ccGFP 1-10 from the second plasmid may leak. After sonication and centrifugation, 20 μl of the 350 μl soluble cell extract fractions (estimated to contain less than 30 pmol of HPS-ccGFP S11) were screened for better complementation efficiency in an in vitro plate assay using a 96-well plate fluorimeter with a molar excess of refolded ccGFP 1-10 v2 (180 μl of 0.75 mg/ml refolded ccGFP 1-10, ~800 μmol). Clones with the fastest complementation rates were selected, pooled, plasmid prepped, and subjected to the next round of evolution and screening. After two rounds of directed evolution ccGFP S11 v2 was selected. HPS-ccGFP S11 v2 solubility was improved relative to HPS-ccGFP S11 E6, and HPS-ccGFP S11 v2 complemented with ccGFP 1-10 v2 three-fold faster and brighter than HPS-ccGFP S11 E6 for comparable amounts of soluble fusion protein.

Expression and Refolding of ccGFP 1-10 and GFP 1-10 Fragments.

Different versions of ccGFP 1-10 and GFP 1-10 proteins were expressed and prepared as previously described (Cabantous et al., Nat Biotechnol 23, 102-107, 2005). One liter LB cultures of BL21 (DE3) cells expressing ccGFP 1-10 or GFP 1-10 constructs were grown until an OD600 nm of 0.5-0.7 was reached, protein expression was induced with 1 mM IPTG and cells were harvested after 5 hours of induction at 37° C. The cell pellets were resuspended in TNG buffer and lysed by sonication on ice. Inclusion bodies were obtained by centrifugation at 20,000 g for 30 minutes, washed, and aliquoted to 75 mg per 1.8 ml Eppendorf tube. To prepare 25 ml of ccGFP 1-10 or GFP 1-10 assay solution, one vial containing 75 mg of prepared inclusion body was unfolded with 1 ml of 9 M urea in TNG buffer, centrifuged at 15,000 g for 10 min, and ~1 ml soluble fraction was rapidly diluted by adding 25 ml of TNG buffer. Refolded protein samples were centrifuged at 15,000 g for 10 min to remove crude precipitate (minor fraction) and the soluble solutions were filtered through a 0.2 mm syringe filter and quantified using the Bio-Rad Protein Assay Reagent Kit (Bio-Rad). To insure ccGFP 1-10 proteins were at equal concentration for subsequent experiments, protein samples were concentrated using a tangential flow Amicon Ultra-15 centrifugal filter device (10 kDa cutoff; Millipore) and protein concentrations were measured and diluted to a final concentration of ~0.75 mg/ml. To examine pH dependence of the complementation of ccGFP 1-10 v2 with ccGFP S11, refolded ccGFP 1-10 v2 was dialyzed against various buffers at different pH values. The protein samples at different pH were then collected, concentrated and diluted to a final concentration of ~0.75 mg/ml. In vitro complementation assays were set up as described below and final fluorescence values were recorded using a Tecan Microplate Fluorescence Reader (Tecan).

Expression and Purification of Sulfite Reductase-ccGFP S11 Fusion Protein.

Sulfite reductase (SR) from P. aerophilum was cloned and expressed as an N-terminal fusion with ccGFP S11 E6 WT and ccGFP S11 fragments in a pET vector with a N-terminal His$_6$ tag. Briefly, 1 liter cultures of BL21 (DE3) cells expressing SR with different versions of ccGFP S11 were grown to OD600 nm ~0.5-0.7 and induced with 1 mM IPTG for 4 hours at 37° C. Cells were harvested and resuspended in TNG buffer and lysed by sonication on ice for 10 minutes at 70% duty cycle. Cell lysates were then centrifuged at 15,000 g for 30 minutes at 10° C. to remove cell debris and the supernatant was incubated with pre-equilibrated Talon® cobalt metal affinity resin (Clontech) at room temperature (22° C.) with gentle rocking for 1 h to allow proteins to bind to resin. The proteins bound to resin was separated from unbound protein by centrifuging at 3,000 g for 5 minutes, and the pelleted resin was washed three times with 10-fold volume excess TNG buffer before it was packed into a gravity-flow column. The column then was washed with 50 ml of TNG buffer followed by 50 ml of TNG buffer with 5 mM imidazole, and 20 ml of TNG buffer with 20 mM imidazole to remove unbound and non-specifically bound proteins, respectively. The purified proteins were completely eluted with 30 ml of 150 mM imidazole in TNG buffer and protein solutions were dialyzed against TNG buffer to eliminate imidazole. Protein was quantified using the Bio-Rad Protein Assay reagent Kit (Bio-Rad) and was concentrated to a final concentration of 5 mg/ml using a tangential flow Amicon Ultra-15 centrifugal filter device (10 kDa cutoff; Millipore).

In Vitro Complementation Assays.

In vitro complementation assays of various combinations of the ccGFP S11 and ccGFP 1-10 were done using previously described protocols (Cabantous et al., Nat Biotechnol 23, 102-107, 2005). Briefly, a 96-well white microplate (Nunc-Immuno plate, Nunc) was first blocked with 0.5% bovine serum albumin (BSA) in TNG for 10 minutes. Purified SR-ccGFP S11 was subjected to twofold serial dilutions in the same buffer so that the dilutions spanned the range 1.56 to 200 pmol per 20 μl aliquot. Protein aliquots were added to 96-well plates and complementation was performed using a large excess of ccGFP 1-10 (0.75 mg/ml, 800 μmol) added in a 180 μl aliquot. Fluorescence kinetics (488 nm excitation/520 nm emission) were monitored with a Tecan Microplate Fluorescence Reader at 3 min intervals for 15 hours. The background fluorescence of a blank sample (20 μl of 0.5% BSA in TNG buffer, 180 μl of 0.75 mg/ml ccGFP 1-10 in TNG buffer) was subtracted from the final fluorescence values. For assays involving the auto-fluorescent ccGFP 1-10 variants v1 and v3, the progress curve for the blank (ccGFP 1-10 alone, no S11) was subtracted from the progress curve of the analytical sample, for the entire time span. For determining solubility levels of 18 protein controls, 20 μl soluble supernatant, or 10 μl of denatured unfolded inclusion bodies were added to the bottom of a Nunc assay plate. 180 μl of ccGFP 1-10 was added to complete the complementation and final fluorescence values were measured after incubation at room temperature (22° C.) overnight using the Tecan Microplate Fluorescence Reader.

In Vivo Complementation Assays.

Eighteen protein controls from P. aerophilum were cloned into the N6His pTET ColEl AnTET vector as an N-terminal fusion with ccGFP S11 fragment and transformed into BL21 (DE3) competent cells containing pET ccGFP 1-10 T7 p15 plasmid for in vivo testing as previously described for split GFP. Proteins expressed from the pTET vector carry an N-terminal 6His tag and C-terminal ccGFP S11 tag. In vivo protein expression and solubility screens were performed as previously described (Cabantous, et al., *Nat Biotechnol* 23, 102-107, 2005). 1 OD600 nm frozen cell stocks in 20% glycerol LB were thawed and diluted 400-fold (twice) in LB and plated onto a nitrocellulose membrane with selective LB agar containing 50 μg/ml kanamycin and 75 μg/ml spectinomycin (the selective media). After overnight growth at 32° C., the membrane was transferred to a pre-warmed selective media plate containing 600 ng/ml AnTET, 1 mM IPTG for 4 hours at 37° C. for total protein expression screening. Under these conditions, both the S11-tagged protein and the ccGFP 1-10 detector fragment are co-expressed. The ccGFP 1-10 can rapidly bind to the S11 tag, prior to insoluble target proteins aggregating, committing to chromophore formation and leading to complementation reflective of total protein. For protein solubility testing, the membrane was transferred to a pre-warmed selective media plate containing 300 ng/ml AnTET for 2 hours, transferred colony side up to its original LB selective media plate for 1 hour to allow the AnTET to diffuse out, and followed by induction on an LB selective plate with 1 mM IPTG at 37° C. for 1 hour to induce the ccGFP 1-10 v2. Under these conditions, the S11-tagged protein is free to remain soluble or aggregate according to its innate propensity prior to the subsequent induction of the ccGFP 1-10 detector. Thus, the fluorescence reflects soluble S11-tagged protein rather than total S11-tagged protein. The induced plates were illuminated and imaged using an Illumatool Lighting System (LightTools Research) equipped with a 488 nm/520 nm excitation/emission filters.

Double-Labeling Experiments

The soluble SR protein from P. aerophilum was cloned and expressed with an N-terminal ccGFP S11, followed by a thrombin cleavage site, and a C-terminal CFP S11 M3 fragment in a pET vector with a N-terminal His$_6$ tag. The fusion protein was expressed and purified as described above for SR-ccGFP S11 proteins. The purified protein was double labeled by incubating with an excess amount of CFP 1-10 OPT and ccGFP 1-10 v2 overnight at 4° C. Protein mixtures were then centrifuged at 15,000 g for 10 minutes at 10° C. to remove any debris and the supernatant was incubated with pre-equilibrated Talon® cobalt metal affinity resin (Clontech) at room temperature (22° C.) with gentle rocking for 1 h to capture protein complex on the resin. The protein complex bound to resin was separated from the excess, uncomplemented ccGFP 1-10 v2 and CFP 1-10 OPT proteins by centrifuging 7,000 g for 5 minutes, and the pelleted resin was washed five times with 3-fold volume excess of TNG buffer. Thrombin cleavage reaction was set up at 37° C. with gentle rocking for 3 h and the flow through fraction was collected. The resin was washed three times with 3-fold volume excess of TNG buffer and photos were taken for both the flow through and the protein complex remaining on the resin fractions using an Illumatool Lighting System equipped with a 488 nm/520 nm and 430 nm excitation/480 nm excitation/emission filters.

Example 2

Highly Stable Variants of Corynactis *Californica* Green Fluorescent Protein

This example describes the refolding kinetics and equilibrium denaturation stability of several full-length *C. californica* GFP scaffold bearing mutations of the various split fragments disclosed herein.

Results

Refolding Kinetics and Stability of Full-Length ccGFP and GFP Variants.

Figure 11:
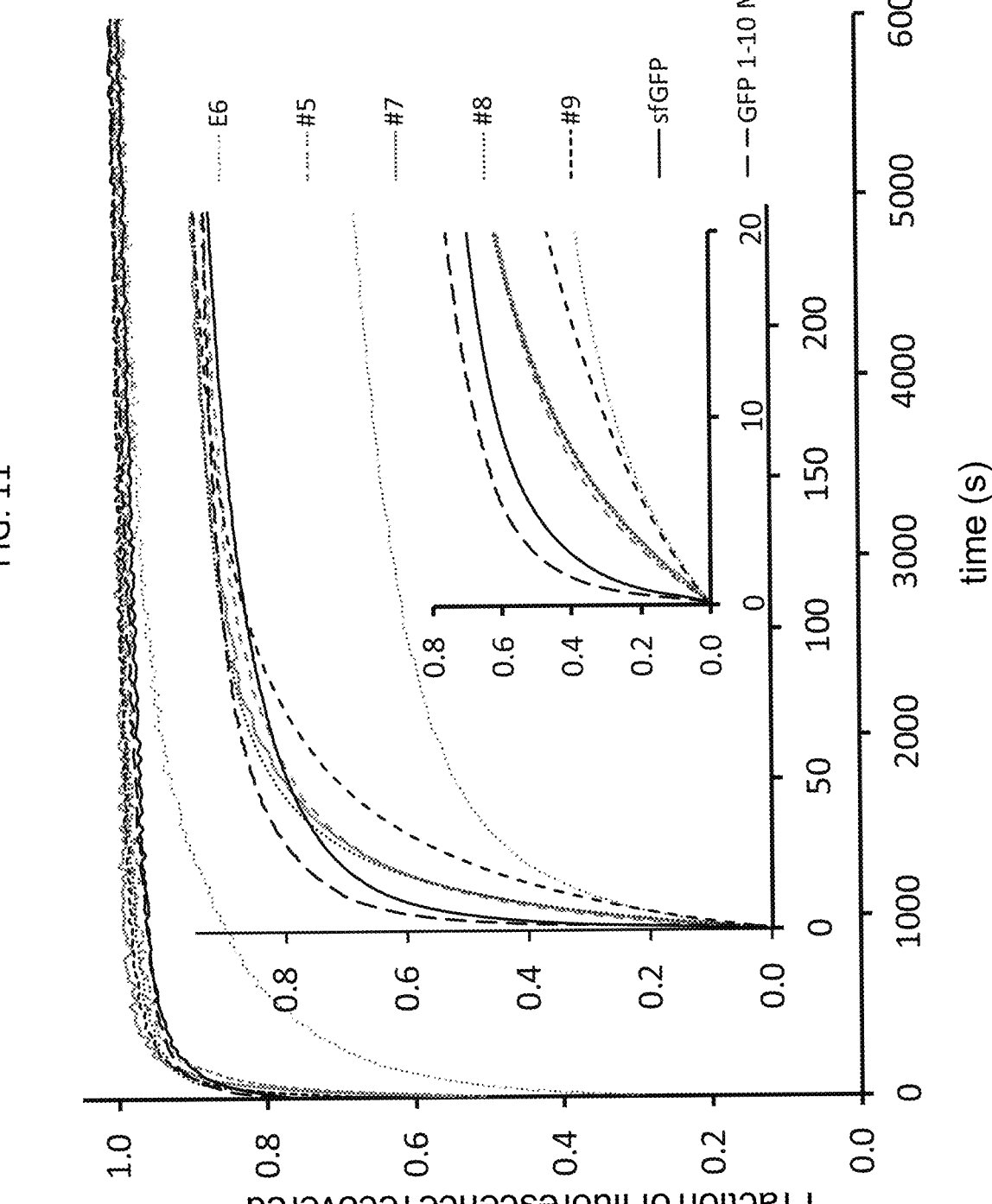
FIG. 11 is a graph showing fluorescence recovery upon renaturation of unfolded fluorescent proteins. Representative long-, medium-, and short-term progress curves for ccGFP E6 (light grey dotted), full-length ccGFPs carrying mutations from the split fragment: ccGFP #5 (light grey dashed), ccGFP #7 (light grey solid), ccGFP #8 (black dotted), ccGFP #9 (black dashed), superfolder GFP (sfGFP) (black solid), and GFP carrying the GFP 1-10 OPT and S11 M3 mutations (GFP 1-10 M3) (blank long dashed).
Figure 16A:
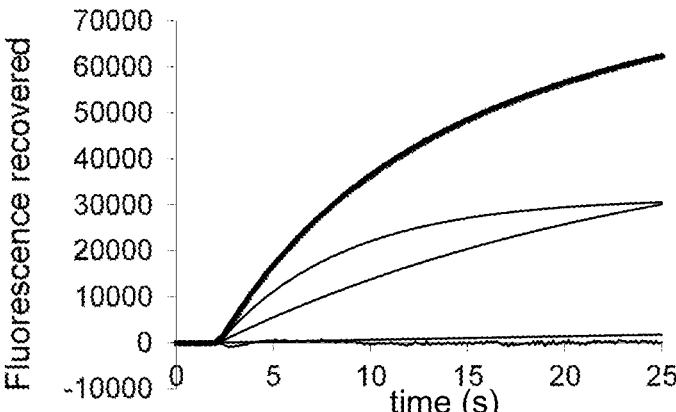
FIGS. 16A-16C are graphs showing ccGFP #8 refolding.
Figure 16B:
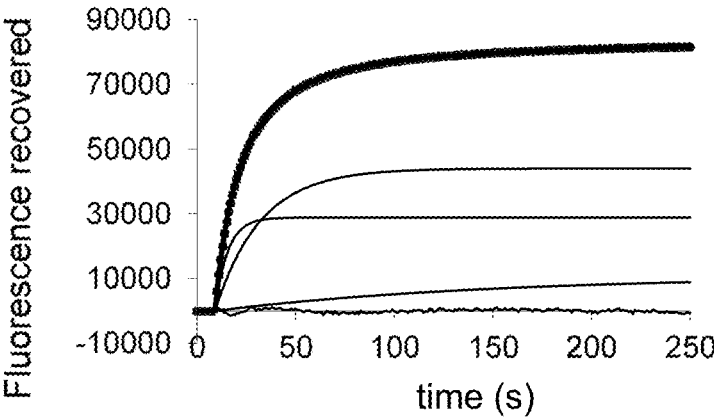
Figure 16C:
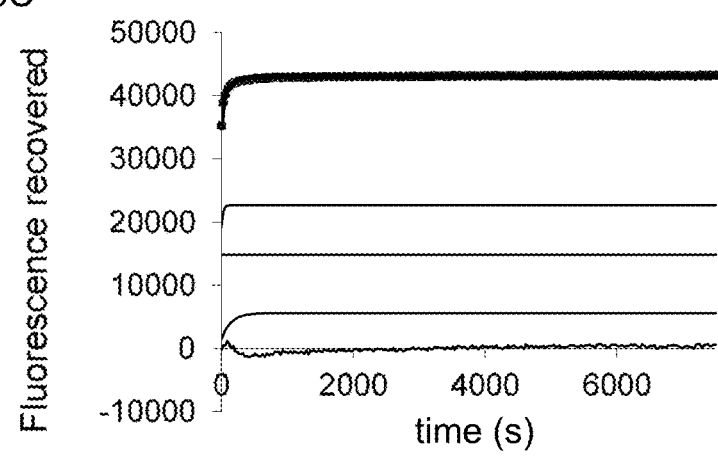
Figure 17A:
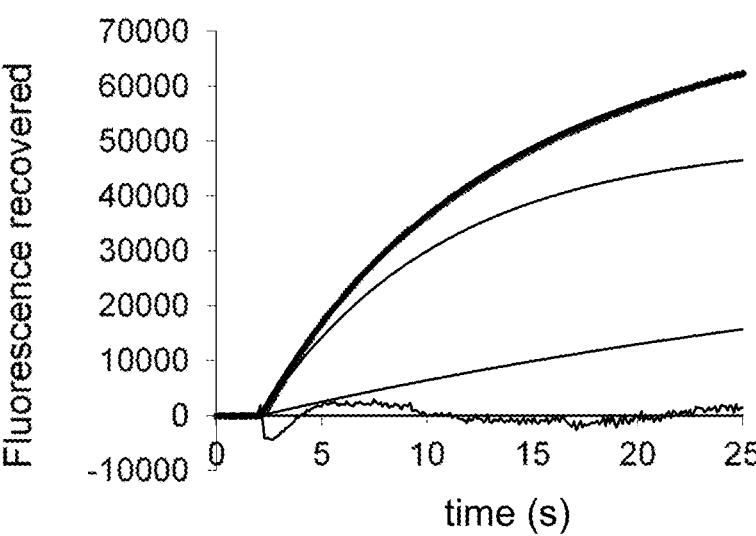
FIGS. 17A-17C are additional graphs showing ccGFP #8 refolding.
Figure 17B:
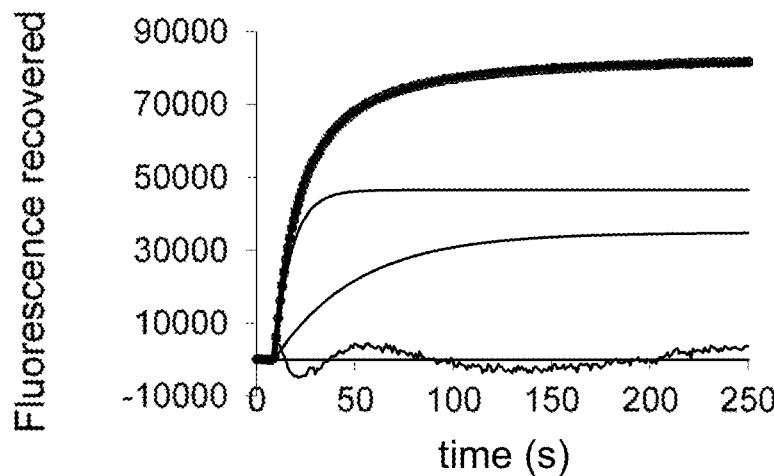
Figure 17C:
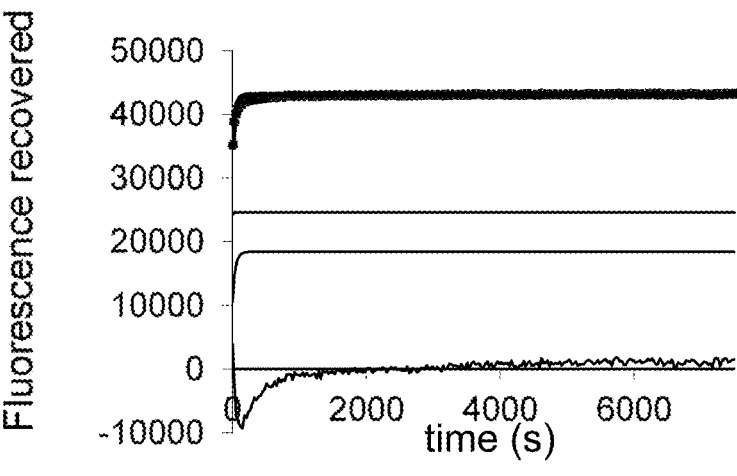
Figure 18A:
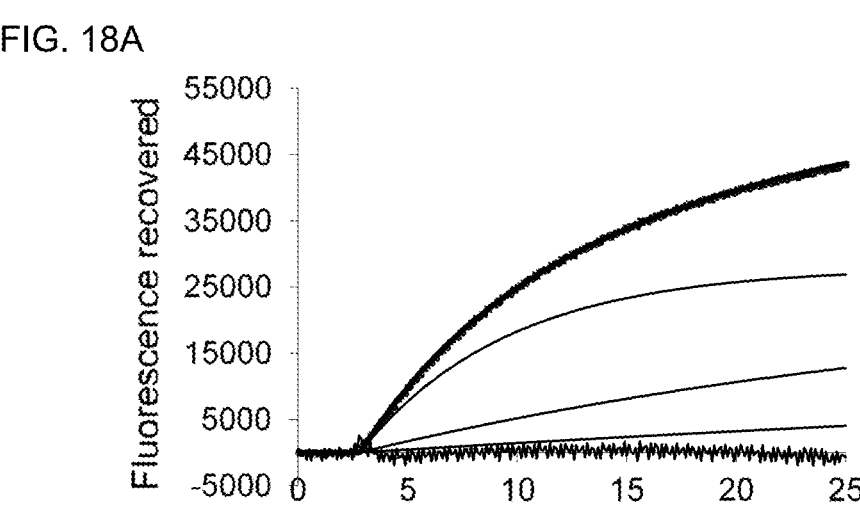
FIGS. 18A-18C are graphs showing ccGFP #7 refolding.
Figure 18B:
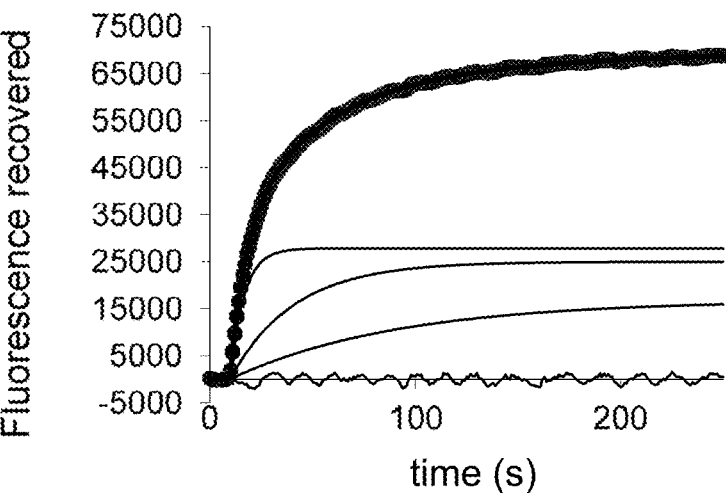
Figure 18C:
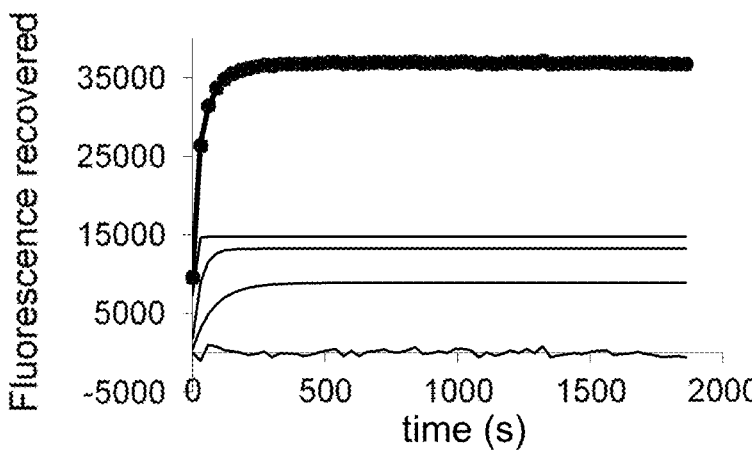
Figure 20A:
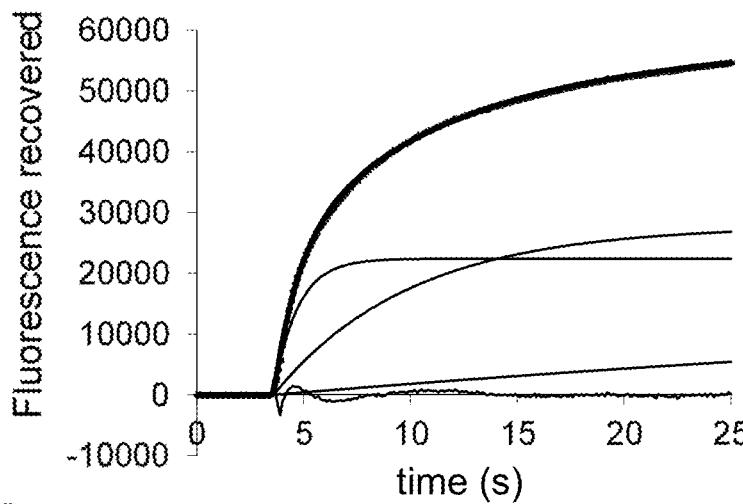
FIGS. 20A-20C are graphs showing sfGFP refolding.
Figure 20B:
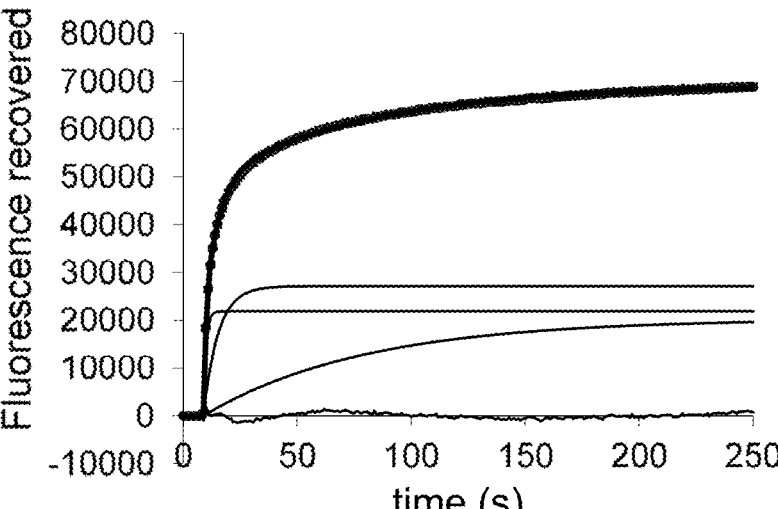
Figure 20C:
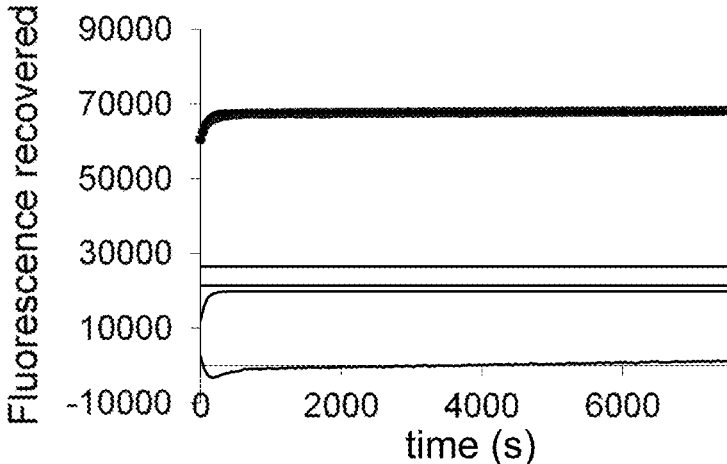
Figure 21A:
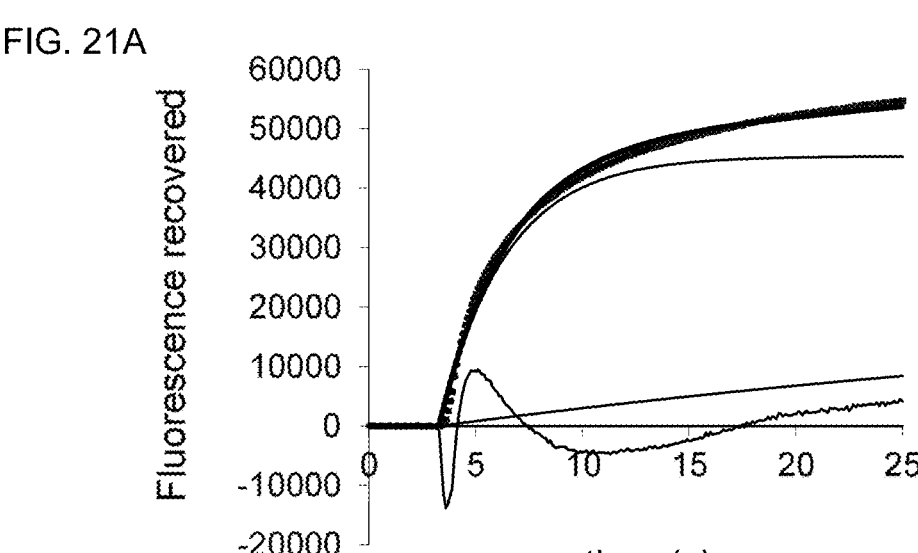
FIGS. 21A-21C are additional graphs showing sfGFP refolding.
Figure 21B:
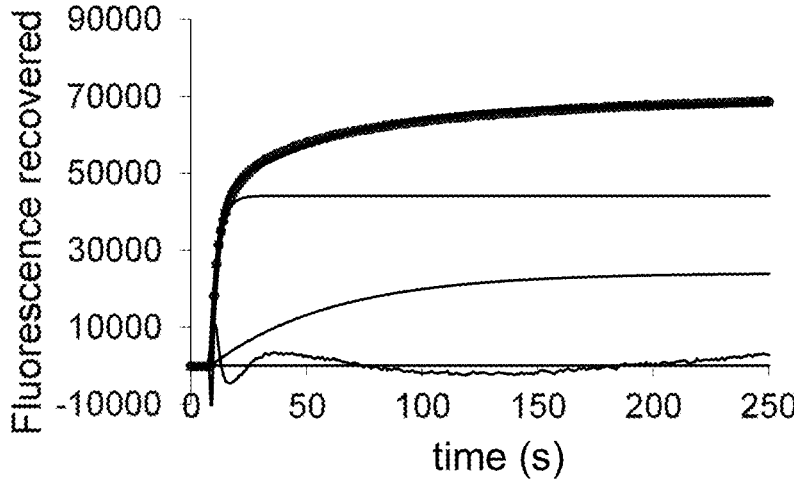
Figure 21C:
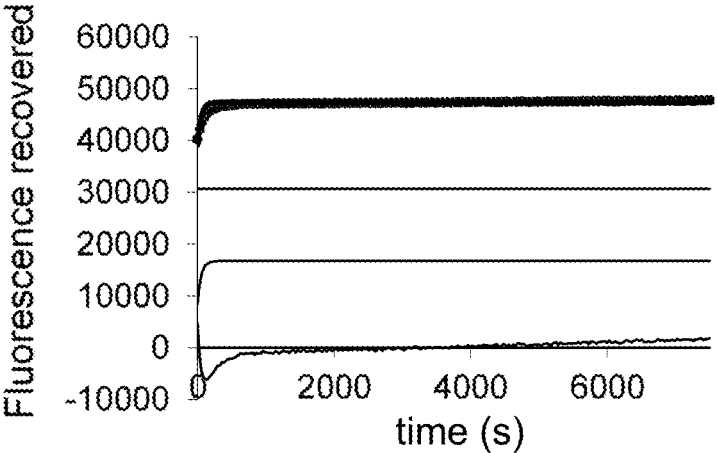
Figure 22A:
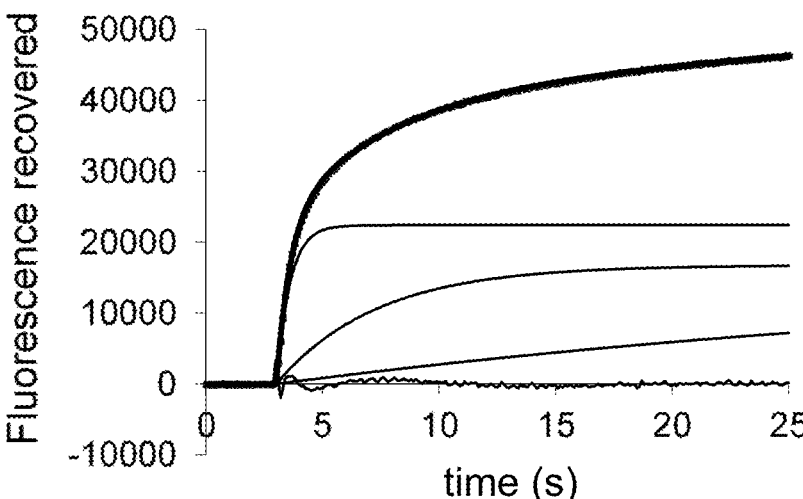
FIGS. 22A-22C are graphs showing GFP 1-1M3 refolding.
Figure 22B:
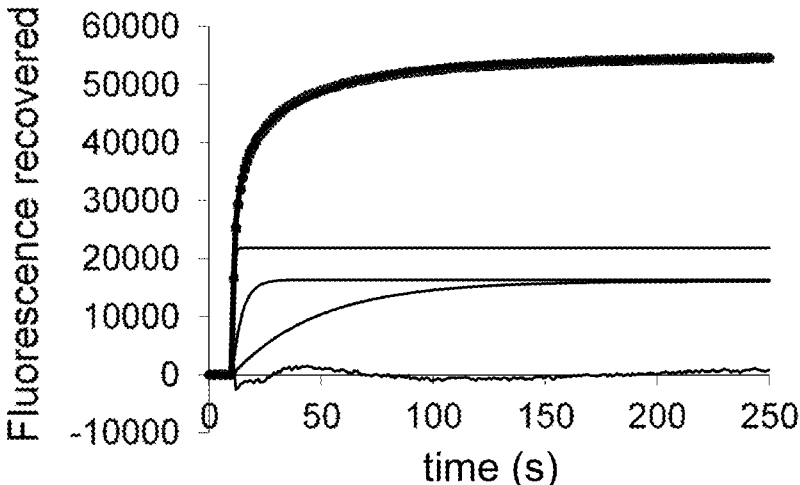
Figure 22C:
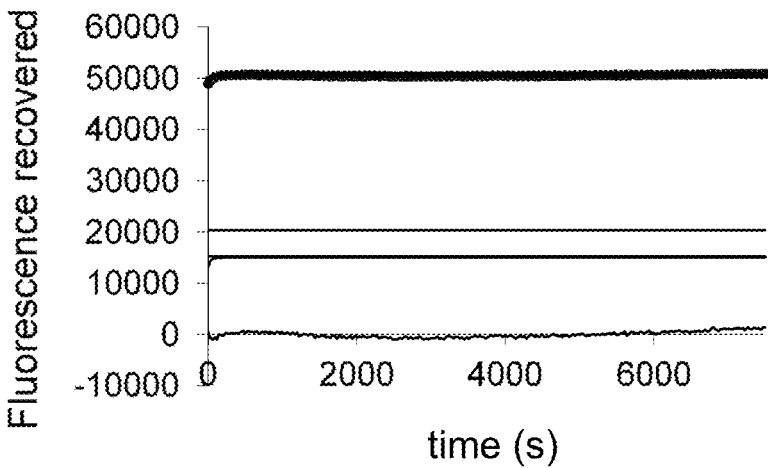
Figure 23A:
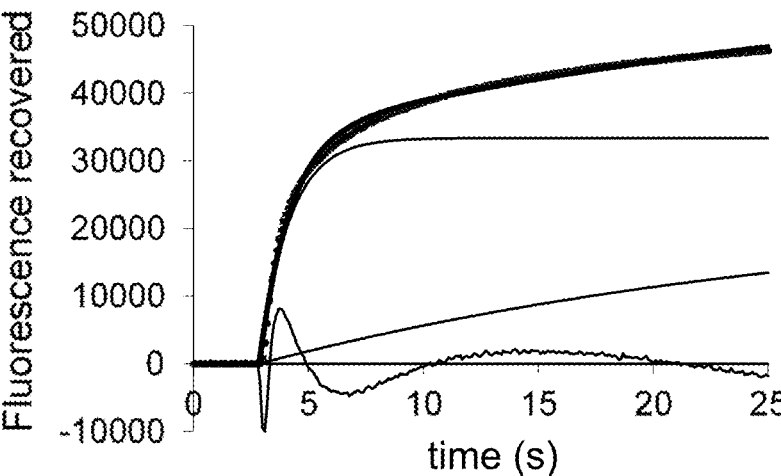
FIGS. 23A-23C are additional graphs showing GFP 1-10M3 refolding.
Figure 23B:
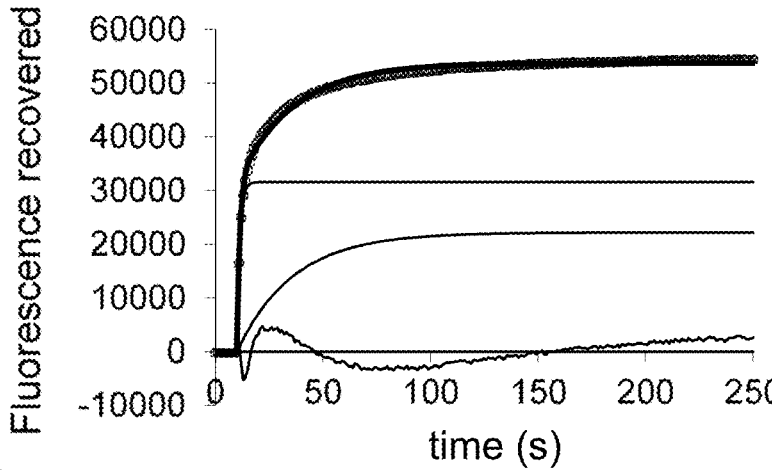
Figure 23C:
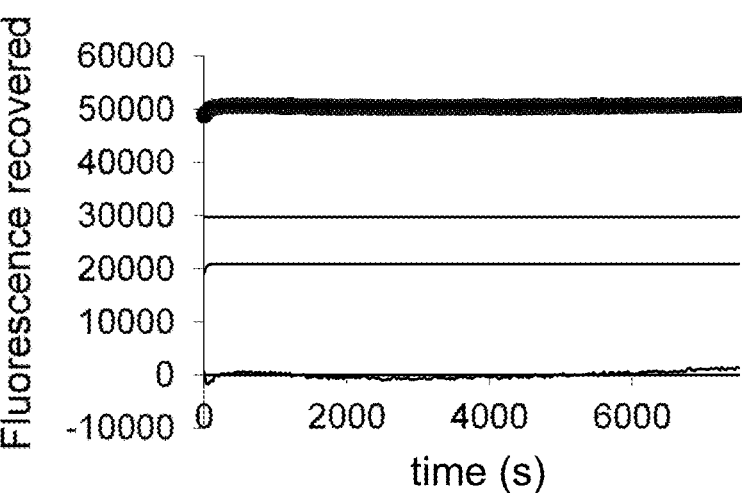

The folding kinetics and stability of the ccGFP E6 (SEQ ID NO: 5) starting optimum was examined, as well as full-length ccGFPs carrying selected combinations of the split protein mutations (FIG. 11). ccGFP E6, the split-protein-derived ccGFPs #5, #7. #8, #9, as well as sfGFP (Pedelacq et al., Nat Biotechnol 24, 79-88, 2006) and GFP 1-10 M3 (full length GFP scaffold carrying the GFP 1-10 OPT and GFP S11 M3 mutants (Cabantous et al., Nat Biotechnol 23, 102-107, 2005)) were denatured in GdnHCl, and the recovery of fluorescence was monitored upon dilution in fresh TNG buffer (FIG. 11). The ccGFP E6 had a pronounced slow phase, taking nearly an hour to recover 95% of the initial fluorescence. In contrast, ccGFPs #5, #7, #8, and #9, as well as sfGFP and GFP 1-10 M3 each recovered more than 95% of the starting fluorescence within 5 min (FIG. 11). Long-, medium- and short-term progress curves were simultaneously fitted with three exponentials using nonlinear least squares (see Table 2, and FIGS. 14-23). Using three exponentials (relaxations) rather than two decreased the overall RMSD of fits more than 2-fold (for example, compare FIG. 16 with FIG. 17, FIG. 20 with FIG. 21, and FIG. 22 with FIG. 23). Referring to FIG. 11 and Table 2, the refolding kinetic parameters of the split-protein-derived ccGFPs #5, #7, #8, and #9 were broadly similar, more than doubling the rate of the first two relaxations, and increasing the rate of the third relaxation up to 30-fold compared to ccGFP E6. Notably, ccGFP #5 differed from ccGFP E6 by only three mutations in S11 (D206E, V208I and V221E), suggesting that much of the improvement in the kinetics of the ccGFP mutants relative to the parent ccGFP E6 was due to the S11 mutations alone. The negatively charged ccGFP #9 exhibited slower kinetics compared to its parent ccGFP #8, perhaps due to effects of the charged residues on the forward folding rate. Both sfGFP and GFP 1-10 M3 exhibited much faster refolding kinetics compared to the ccGFP proteins overall. In particular, the first relaxation of the both GFPs was up to 10-fold faster than the ccGFPs (FIG. 11 and Table 2). Interestingly the rapid burst during refolding measured here for sfGFP denatured in guanidine ($k_1$=9.7+0.4×10$^{-1}$s$^{-1}$) is significantly slower than previously reported for sfGFP denatured in urea ($k_1$=13.5+0.8×10$^{-1}$s$^{-1}$), perhaps due 10 to the differences in denaturation relative to urea by guanidine or its counter-ion Cl-. On the other hand, after guanidine denaturation, the burst for GFP 1-10 M3 ($k_1$=13.0+0.2×10$^{-1}$s$^{-1}$) was faster than for sfGFP. Apparently the split GFP mutations improve the forward refolding rate compared to the sfGFP parent in the context of the full-length scaffold.

| | Fluorescent protein refolding kinetic parameters, and equilibrium refolding | | | | | |
|---|---|---|---|---|---|---|
| protein | $^a k_1$ $(10^{-1}\,s^{-1})$ | $^a k_2$ $(10^{-2}\,s^{-1})$ | $^a k_3$ $(10^{-3}\,s^{-1})$ | $^b a1$ | $^b a2$ | $^b a3$ |
| $^f$E6 | 1.1 ± 0.1 | 1.7 ± 0.1 | 0.48 ± 0.02 | 0.31 ± 0.01 | 0.27 ± 0.01 | 0.42 ± 0.01 |
| $^f$#5 | 2.2 ± 0.1 | 5.9 ± 0.6 | 15 ± 2 | 0.31 ± 0.04 | 0.39 ± 0.05 | 0.30 ± 0.04 |
| $^f$#8 | 1.6 ± 0.1 | 4.4 ± 0.4 | 7.2 ± 0.4 | 0.34 ± 0.03 | 0.53 ± 0.02 | 0.13 ± 0.02 |
| $^f$#7 | 1.5 ± 0.1 | 4.3 ± 0.7 | 12 ± 0.5 | 0.40 ± 0.03 | 0.36 ± 0.05 | 0.24 ± 0.06 |
| $^f$#9 | 1.0 ± 0.1 | 2.7 ± 0.2 | 3.5 ± 0.3 | 0.24 ± 0.02 | 0.60 ± 0.01 | 0.17 ± 0.01 |
| $^h$SF | 9.7 ± 0.4 | 16.0 ± 0.2 | 14.3 ± 0.1 | 0.46 ± 0.02 | 0.23 ± 0.04 | 0.26 ± 0.07 |
| $^i$1-10 M3 | 13.0 ± 0.2 | 15.7 ± 0.2 | 23.0 ± 0.5 | 0.44 ± 0.02 | 0.30 ± 0.01 | 0.26 ± 0.02 |

| protein | $^c C_{1/2}$ (M) 22° C. | $^d \Delta G(H_2O)$ (kcal mol$^{-1}$) 22° C. | $^e m$ (kcal mol$^{-1}$ M$^{-1}$) 22° C. | $^c C_{1/2}$ (M) 50° C. | $^d \Delta G(H_2O)$ (kcal mol$^{-1}$) 50°C | $^e m$ (kcal mol$^{-1}$ M$^{-1}$) 50° C. |
|---|---|---|---|---|---|---|
| $^f$E6 | 5.75 ± 0.05 | 9.6 ± 0.3 | 1.68 ± 0.06 | 3.59 ± 0.03 | 5.9 ± 0.1 | 1.63 ± 0.03 |
| $^f$#5 | 5.68 ± 0.08 | 10.0 ± 0.4 | 1.77 ± 0.07 | 3.54 ± 0.05 | 5.7 ± 0.1 | 1.62 ± 0.02 |

-continued

| | | | Fluorescent protein refolding kinetic parameters, and equilibrium refolding | | | |
|---|---|---|---|---|---|---|
| [f]#8 | [g]NA | [g]NA | [g]NA | 6.41 ± 0.06 | 12.0 ± 0.5 | 1.9 ± 0.1 |
| [f]#7 | 5.06 ± 0.07 | 7.9 ± 0.1 | 1.57 ± 0.04 | 2.99 ± 0.03 | 4.5 ± 0.1 | 1.51 ± 0.04 |
| [f]#9 | 6.64 ± 0.05 | 10.3 ± 0.6 | 1.6 ± 0.1 | 5.48 ± 0.04 | 9.0 ± 0.1 | 1.7 ± 0.1 |
| [h]SF | 4.27 ± 0.05 | 9.3 ± 0.4 | 2.22 ± 0.04 | 2.13 ± 0.05 | 4.3 ± 0.3 | 2.0 ± 0.1 |
| [i]1-10 M3 | NA | NA | NA | NA | NA | NA |

Figure 12A:
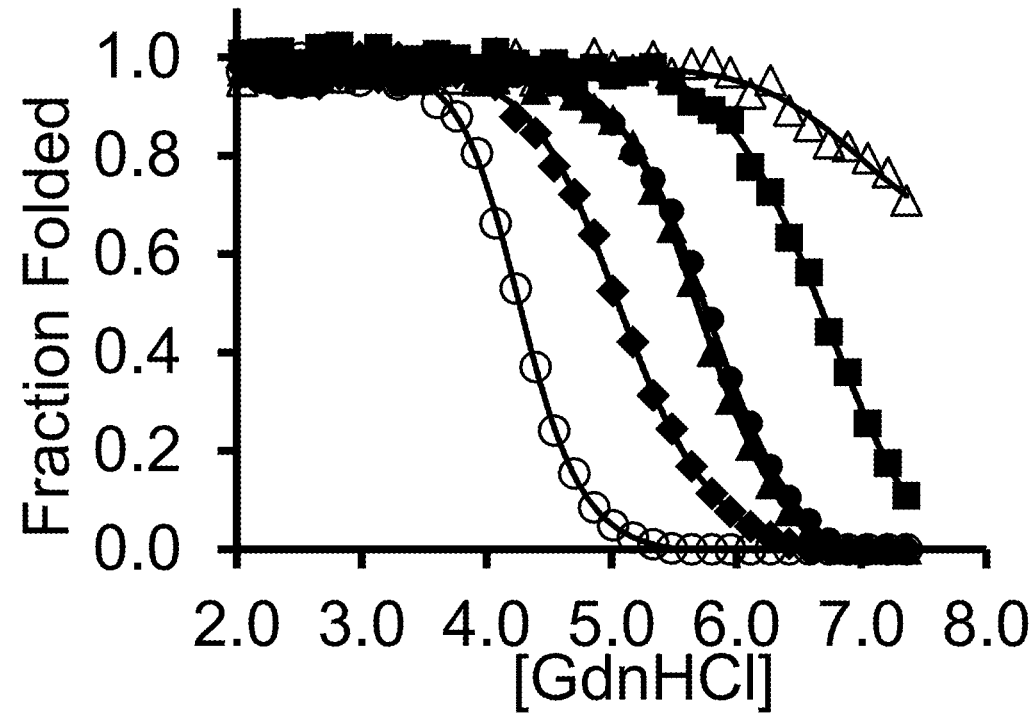
FIGS. 12A and 12B show GFP and ccGFP equilibrium unfolding plots at 22° C.
Figure 12B:
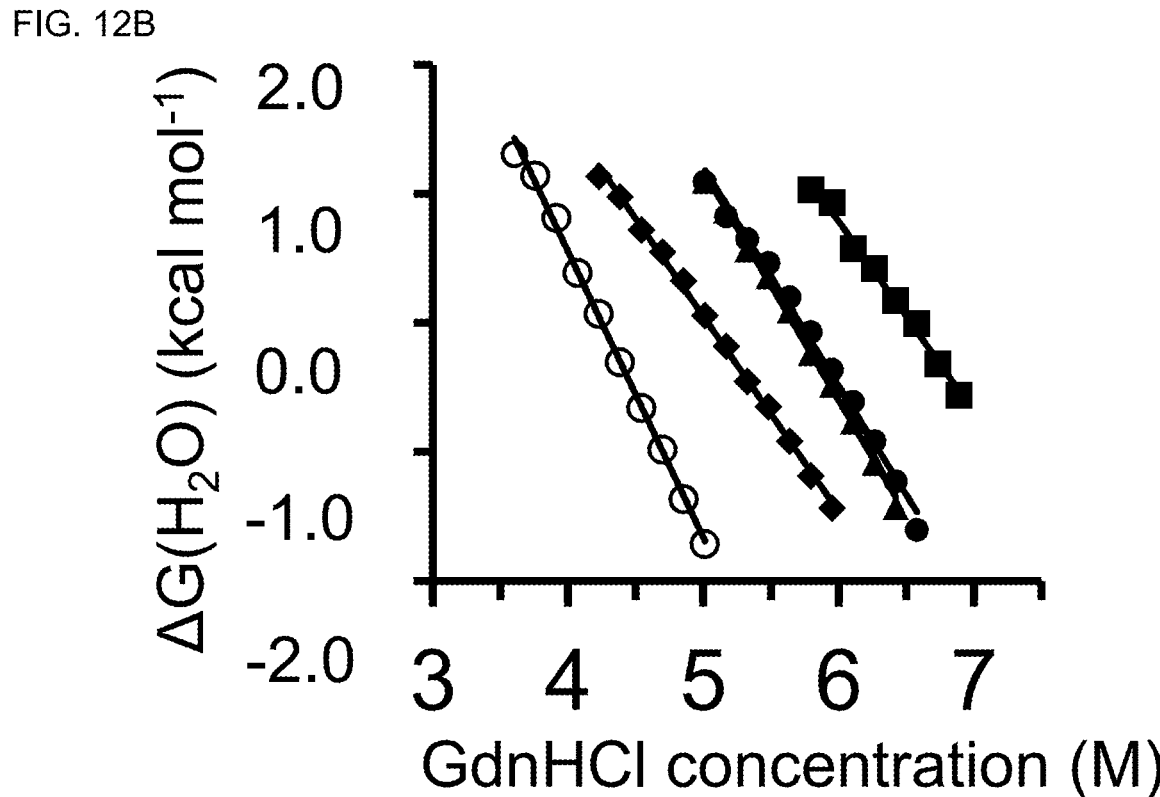

[a]Rate constants for three-exponential fits of refolding progress curves of nonfusion ccGFP variant. Errors reported are one standard deviation, four replicates ($k_1$-$k_3$).
[b]Relative magnitude of each exponential process ($a_1$-$a_3$).
[c]Transition concentration of guanidine at which 50% of the initial fluorescence is retained after 2-1/2 weeks of equilibration at the indicated temperature ($C_{1/2}$), determined by fitting the renaturation profiles of FIG. 12 for 22° C and FIG. 13 for 50° C.
[d]Free energy of denaturation $\Delta G° = \Delta G(H_2O) - m(\text{guanidine})$.
[e]Measure of dependence of $\Delta G$ as a function of denaturant concentration, that is, slope of plots in FIG. 12 for 22° C and FIG. 13 for 50° C.
[f]Indicated ccGFP mutant.
[g]Protein is too stable to measure and calculate these parameters at 22° C.
[h]Superfolder GFP Pedelacq et. al *Nat. Biotechnol.* 24: 79-88, 2006.
[i]Full-length GFP scaffold carrying the GFP 1-10 OPT and S11 M3 mutations Cabantous et. al., *Nat. Biotechnol.* 23: 102-107, 2005.
[j]Parameters not measured or derived.

Stability

Figures 13A, 13B:
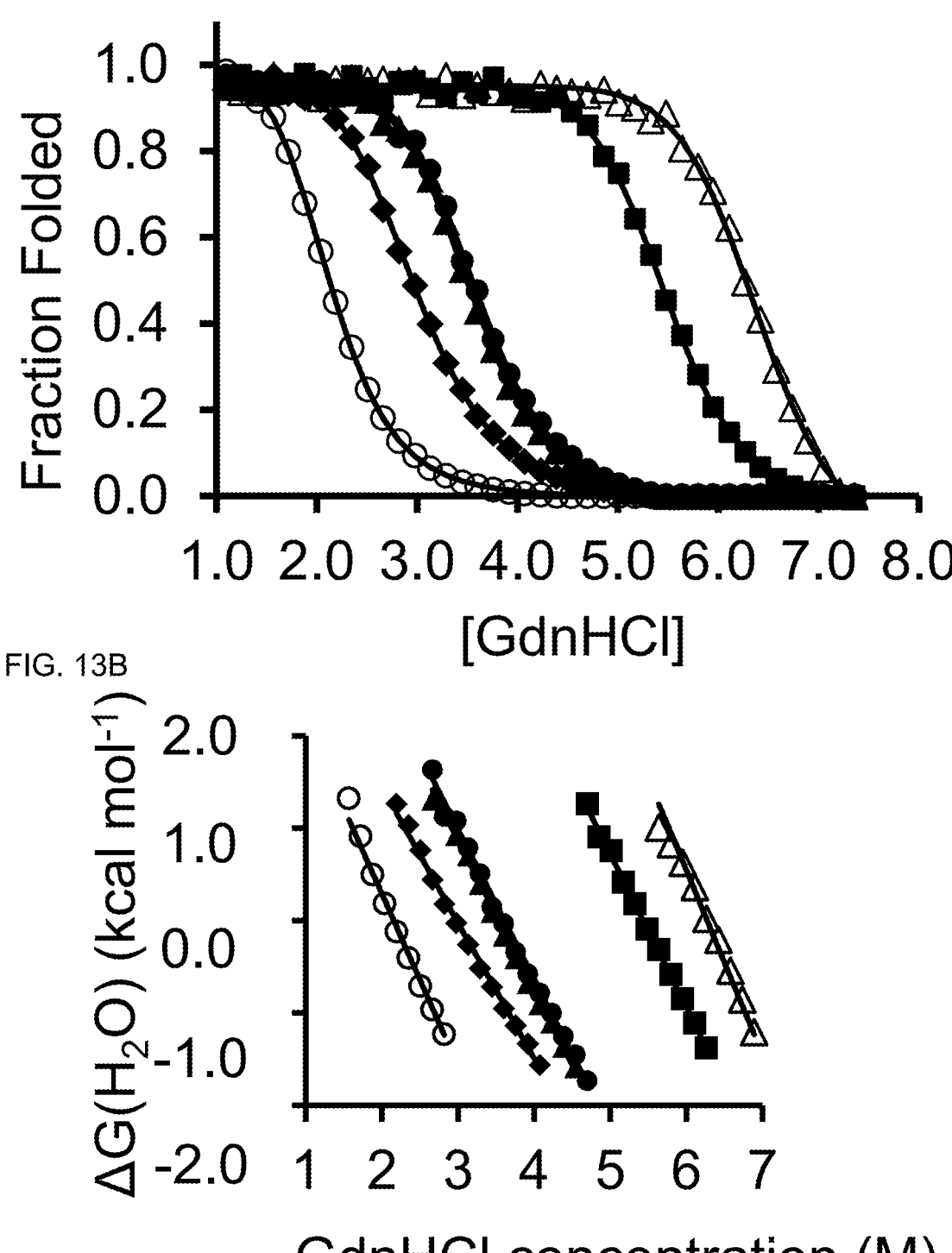
FIGS. 13A and 13B show GFP and ccGFP equilibrium unfolding plots at 50° C.
Figure 14A:
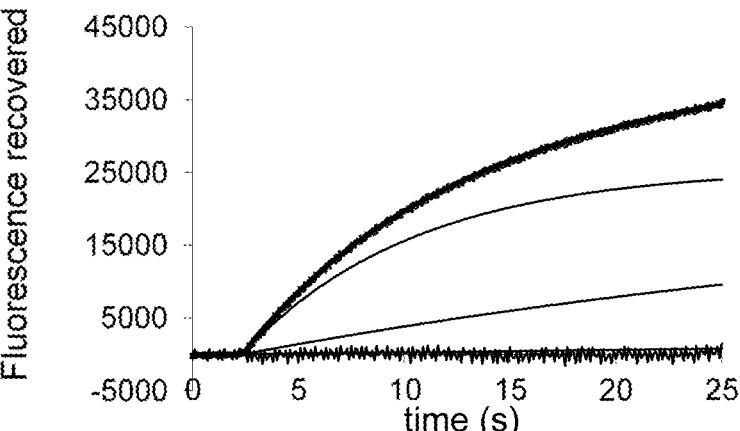
FIGS. 14A-14C are graphs showing ccGFP E6 refolding.
Figure 14B:
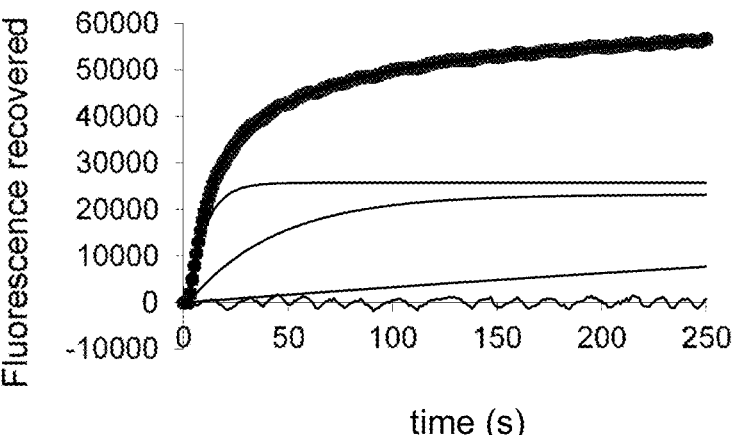
Figure 14C:
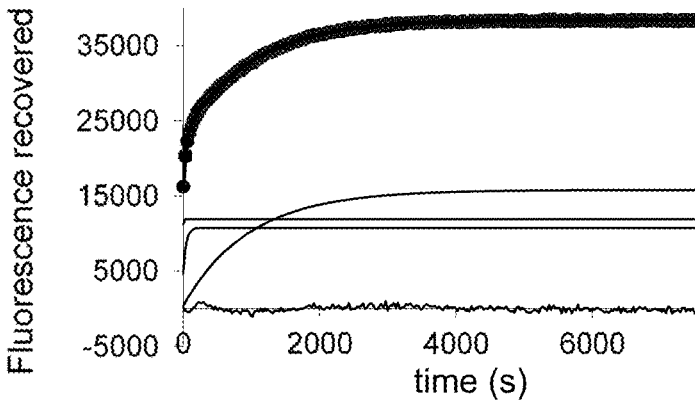
Figure 15A:
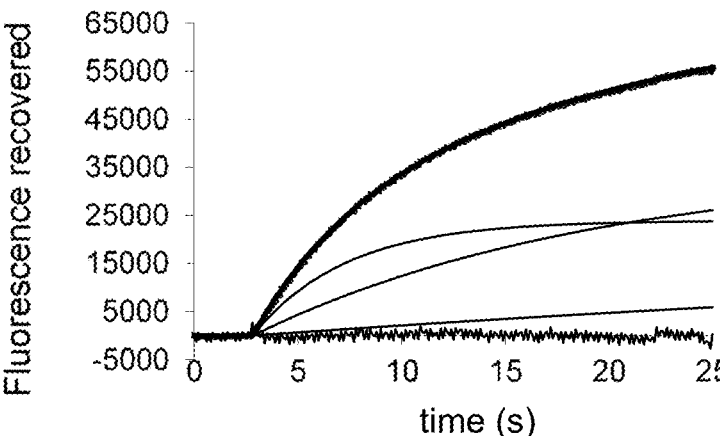
FIGS. 15A-15C are graphs showing ccGFP #5 refolding.
Figure 15B:
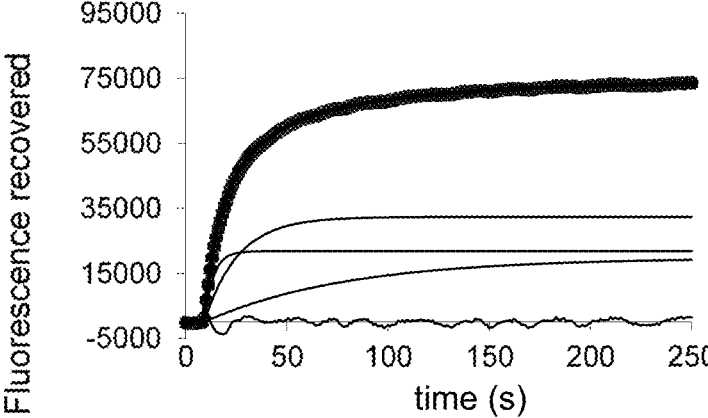
Figure 15C:
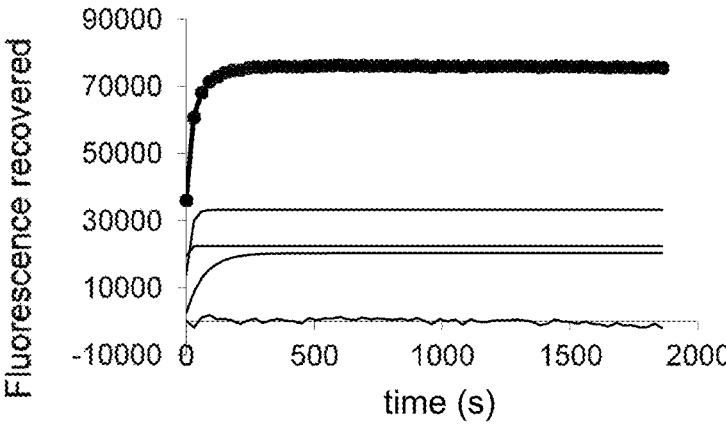

The tolerance of the various ccGFP and GFP constructs to guanidine denaturation was tested by equilibrium unfolding. Aliquots of the fluorescent protein variants were introduced in buffers containing varying concentrations of guanidine and incubated at 22° C. or 50° C., and the fraction of remaining fluorescence was determined at various times until no further decrease was observed (typically 2-½ weeks), at equilibrium. Equilibration of the fluorescence took substantially longer closer to the mid-point transition concentration ($C_{1/2}$. Table 2) as previously noted during the unfolding of GFPs. The fraction of fluorescence recovered at 2-½ weeks was plotted as a function of guanidine concentration in the buffer (FIG. 12A and FIG. 13A), and the mid-point concentration at which 50% of the fluorescence remained was determined by sigmoidal fits to the equilibrium denaturation plots using nonlinear least squares (Table 2). The stabilities of the fluorescent protein variants were estimated from the dependence of the free energy on guanidine concentration (Table 2, FIG. 12B, and FIG. 13B). All of the ccGFP-derived proteins with the exception of ccGFP #7 (derived from the ccGFP 1-10 v2 fragment containing mutations eliminating autofluorescence) were substantially more stable than the GFP proteins. Whereas all the ccGFP split-derived proteins (ccGFP #5, #7, #8, #9) had similar refolding kinetics, ccGFP #8 (containing six 1-10 mutations in addition to the three S11 mutations) was dramatically more stable than either ccGFP E6 or ccGFP #5. In fact, ccGFP #8 could not be fully unfolded at 22° C. even in 7.4 M guanidine (the maximum concentration where guanidine remained soluble) where it retained 70% of the initial fluorescence measured in the absence of denaturant. At 50° C. all of the proteins could be unfolded at or below 7.4 M guanidine and thermodynamic parameters derived (Table 2). The $\Delta G$ ($H_2O$) for ccGFP #8, the protein whose 1-10 fragment exhibited autofluorescence, was 12.0±0.5 kcal mol-1, at least 6 kcal mol$^{-1}$ more stable than ccGFP E6 or ccGFP E5. Notably, ccGFP #7 containing mutations D78Y, Q85R, and A109V that eliminate autofluorescence associated with its parent ccGFP #8, was far less stable with $\Delta G$ ($H_2O$)=2.99+0.03 kcal mol$^{-1}$, despite having similar forward refolding kinetics as ccGFP #8 (Table 2). On the other hand, the supercharged variant of ccGFP #8, that is ccGFP #9, was destabilized by ~1 kcal mol$^{-1}$ relative to ccGFP #8 at 50° C. and could even be fully unfolded at 22° C. (FIGS. 13A and 13B and Table 2).

Materials and Methods

Cloning and expression of full-length fluorescent proteins. ccGFPs, and GFP 1-10 OPT-S11M3 were constructed by PCR extension of the DNA for the S11 fragment from the 3' end of the DNA coding the corresponding 1-10 fragment. Templates for PCR were the pET plasmids carrying the DNA coding the corresponding 1-10 fragment. The same 5' primer was used to target the plasmid 50 bp upstream of all of the GFP 1-10 constructs. Up to 4 primers were used sequentially to extend the 3' end to add the corresponding S11, ending with a BamHI site. The resulting full-length amplicons were digested, resolved on 1.5% agarose, gel purified, and cloned into the NdeI/BamHI site of a fresh pET 28 vector (p15 ORI and KanR antibiotic selection marker) with a short-GGGS-linker and C-terminal 6His tag. Full-length fluorescent proteins were expressed from BL21 (DE3) at 37° C. and purified using Talon resin as previously described (Pedelacq et al., Nat Biotechnol 24, 79-88, 2006). Proteins were quantified using the bicinchoninic acid assay (Thermo Fisher Scientific) as previously described and stored at 5 mg/ml in 100 µl aliquots 100 mM TRIS pH 7.5, 150 mM NaCl, 10% v/v glycerol (TNG) buffer at −80° C.

Kinetic and Equilibrium Refolding Measurements.

Purified ccGFP and GFP variants bearing a C-terminal 6His tag at 10 mg/ml TNG buffer were diluted 400-fold in 8M guanidine HCl, 1 mM DTT and unfolded at 95° C. for 5 min. To measure refolding kinetics, 10-ml aliquots of the diluted, unfolded samples in a 96 well microplate (Nunc-Immuno plate, Nunc) were rapidly diluted with 200 ml of fresh TNG buffer and fluorescence was measured using a FL600 Microplate Fluorescence Reader (488-nm excitation, 530-nm emission, 10-nm band pass). A 1-mm diameter pinhole aperture was fitted to the excitation filter to reduce the intensity by approximately tenfold to minimize photobleaching of the fluorescent protein. For each of three separate experiments, 250 data points were collected for 25 s at 0.1 s intervals (short-term progress curve), 250 s at 1.0 s intervals (medium-term progress curve), or 7500 s at 30 s intervals (long-term progress curve). Data collection was initiated a few seconds before the injection of diluent to establish a baseline trace. Up to three exponential functions were fit simultaneously to short-, medium-, and long-term progress curves using the SOLVER function in EXCEL (Microsoft). Short-term fluorescence progress curves $F_{sj}$ for j=250 points were modeled using the equation $$F_{Sj}=A_S+\Sigma a_i e^{-bit(tj+CS)}$$

for i=1 to 3 where the exponential factors $a_i$ and $b_i$, the time offset $C_S$, and fluorescence offset As are adjustable parameters. Medium-term and long-term progress curve fluorescence data were modeled using the equations $$F_{Mj}=A_M+V_M\Sigma a_i e^{-bit(tj+CM)}$$

for i=1 to 3, and $$F_{Lj}=A_L+V_L\Sigma a_i e^{-bit(tj+CM)}$$

for i=1 to 3.

Additional adjustable scaling factors $V_M$ and $V_L$ compensated for small differences between sample volumes between experiments, and ranged from 0.96 to 1.05. The objective function minimized the square root of the sum of the squares of the difference between the measured fluorescence data (short-term, medium-term, and long-term progress curves) and the models, evaluated over the 250 data points. Two independent long-term experiments and four independent short-term and medium-term experiments were collected for each FP variant, and up to twelve combinations of data (short-, medium-, and long-term) were fitted simultaneously (250×3=1500 data points). Taken over the short-, medium-, and long-term progress curves together, three-exponential fits typically improved the goodness-of-fit (r.m.s.d.) more than two-fold (compare FIGS. 14 and 15) and typically three-fold (compare FIGS. 17 and 18) relative to two-exponential fits, whereas four-exponential fits failed to improve the goodness-of-fit substantially. Equivalent results were obtained whether the total fluorescence at infinite time was allowed to float, or was fixed at the fluorescence value measured at 15 h, indicating that the kinetic measurements were sampled for a sufficient time to constrain the kinetic parameters in the fits. Equilibrium fluorescence values were measured by diluting fluorescent proteins (see above) into TNG containing 5 mM DTT to various final urea concentrations between 0.63 and 7.4 M in increments of 0.1 M guanidine HCl, and allowing refolding to proceed up to 72 h at 22° C. or 50° C. Fluorescence values were measured using a FL600 Microplate Fluorescence Reader (488-nm excitation, 530-nm emission, 10-nm band pass) and scaled by dividing by the fluorescence levels of corresponding nondenatured samples diluted in parallel as a reference. Midpoint recovery concentrations of urea Cm (recovery of 50% of the initial fluorescence) were determined from sigmoidal fits using SOLVER in EXCEL, to the scaled fluorescence value F using the equation $$F_j=a+b/(1+(C_j/C_m)^h,$$

where a, b, $C_m$ and h are adjustable parameters, and $C_j$ is the molarity of the urea in the refolding experiment j.

The data were used to calculate the dependence of the standard free energy of denaturation, $\Delta G°=-RT \ln K$, on guanidine concentration, where R is the gas constant, T is the absolute temperature and K is the equilibrium constant, which can be calculated from the experimental data by using the standard equation $$K=[(y)N-(y)]/[(y)-(y)D],$$

where (y) is the observed value of the parameter used to follow unfolding, and (y) N and (y) D are the (y) values for the native state and the denatured state, respectively, under the same conditions under which (y) was measured. The conformational stability of the various GFP variants was subsequently estimated using the equation $$\Delta G°=\Delta G(H_2O)-m[\text{guanidine}]$$

where $\Delta G$ ($H_2O$) is an estimate of the conformational stability of a protein that assumes that the linear dependence continues to infinite dilution of the denaturant, and m is a measure of the dependence of $\Delta G$ on guanidine concentration.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

We claim:

1. An isolated polypeptide comprising a Split Fluorescent Protein (SFP) detector comprising:

(i) an amino acid sequence having at least 95% sequence identity to the amino acid sequence of SEQ ID NO: 1, wherein amino acid residue 11 is asparagine, amino acid residue 14 is threonine, amino acid residue 43 is serine, amino acid residue 100 is glutamic acid, amino acid residue 104 is threonine, and amino acid residue 152 is proline, and wherein the SFP detector complements with an SFP tag to form a functional SFP; or (ii) an amino acid sequence having at least 95% sequence identity to the amino acid sequence of SEQ ID NO: 3, wherein amino acid residue 4 is glutamic acid, amino acid residue 11 is asparagine, amino acid residue 14 is threonine, amino acid residue 23 is aspartic acid, amino acid residue 28 is glutamic acid, amino acid residue 41 is glutamic acid, amino acid residue 43 is glutamic acid, amino acid residue 100 is glutamic acid, amino acid residue 104 is threonine, amino acid residue 142 is aspartic acid, amino acid residue 152 is proline, amino acid residue 153 is glutamic acid, and amino acid residue 162 is glutamic acid, and wherein the SFP detector complements with an SFP tag to form a functional SFP.

2. The isolated polypeptide of claim 1, further comprising wherein amino acid residue 78 is tyrosine, amino acid residue 85 is arginine, and amino acid residue 109 is valine.

3. The isolated polypeptide of claim 1, comprising or consisting of the amino acid sequence of any one of SEQ ID NOs: 1-3.

4. An isolated polypeptide comprising a Split Fluorescent Protein (SFP) tag comprising an amino acid sequence having at least 95% sequence identity to the amino acid sequence of SEQ ID NO: 4, wherein amino acid residue 2 is glutamic acid, amino acid 4 is isoleucine, and amino acid 17 is glutamic acid, and wherein SFP tag complements with an SFP detector to form a functional SFP.

5. The isolated polypeptide of claim 4, comprising or consisting of the amino acid sequence of SEQ ID NO: 4.

6. An isolated polypeptide comprising a green fluorescent protein comprising:

(i) an amino acid sequence having at least 95% sequence identity to the amino acid sequence of SEQ ID NO: 8, wherein amino acid residue 206 is glutamic acid, amino acid residue 208 is isoleucine, and amino acid residue 221 is glutamic acid; or (ii) an amino acid sequence having at least 95% sequence identity to the amino acid sequence of SEQ ID NO: 7, wherein amino acid residue 4 is glutamic acid, amino acid residue 11 is asparagine, amino acid residue 14 is threonine, amino acid residue 23 is aspartic acid, amino acid residue 28 is glutamic acid, amino acid residue 41 is glutamic acid, amino acid residue 43 is glutamic acid, amino acid residue 100 is glutamic acid, amino acid residue 104 is threonine, amino acid residue 142 is aspartic acid, amino acid residue 152 is proline, amino acid residue 153 is glutamic acid, amino acid residue 162 is glutamic acid, amino acid residue 206 is glutamic acid, amino acid residue 208 is isoleucine, and amino acid residue 221 is glutamic acid.

7. The isolated polypeptide of claim 6, further comprising wherein amino acid residue 11 is asparagine, amino acid residue 14 is threonine, amino acid residue 43 is serine, amino acid residue 100 is glutamic acid, amino acid residue 104 is threonine, and amino acid residue 152 is proline.

8. The isolated polypeptide of claim 7, further comprising wherein amino acid residue 78 is tyrosine, amino acid residue 85 is arginine, and amino acid residue 109 is valine.

9. The isolated polypeptide of claim 6, comprising or consisting of the amino acid sequence of any one of SEQ ID NOs: 6-9.

10. A split-fluorescent protein system, comprising at least two polypeptide fragments of a fluorescent protein, comprising:

a first polypeptide comprising the isolated polypeptide of claim 1; and a second polypeptide comprising a Split Fluorescent Protein (SFP) tag comprising an amino acid sequence having at least 95% sequence identity to the amino acid sequence of SEQ ID NO: 4, wherein amino acid residue 2 is glutamic acid, amino acid 4 is isoleucine, and amino acid 17 is glutamic acid, and wherein the SFP tag complements with an SFP detector to form a functional SFP.

11. The split-fluorescent protein system of claim 10, wherein:

the at least two polypeptide fragments together contain the full complement of beta-strands in the fluorescent protein; and/or the at least two polypeptide fragments spontaneously self-complement to reconstitute the fluorescent protein and a fluorescent phenotype.

12. A method of detecting a protein of interest, comprising:

providing the SFP detector of claim 1 and a SFP tag linked to the protein of interest, wherein the SFP detector and SFP tag complement to form a fluorescent protein complex; and detecting fluorescence of the fluorescent protein complex, thereby detecting the protein of interest.

13. A method of detecting interaction between a first polypeptide and a second polypeptide, comprising:

providing the SFP detector of claim 1 linked to the first polypeptide and a SFP tag linked to the second polypeptide wherein the SFP detector and SFP tag complement to form a fluorescent protein complex on interaction between the first polypeptide and the second polypeptide; and detecting fluorescence of the fluorescent protein complex, thereby detecting the interaction between the first polypeptide and the second polypeptide.

<p align="center">*   *   *   *   *</p>